United States Patent [19]

Rosamond

[11] Patent Number: 5,086,042

[45] Date of Patent: Feb. 4, 1992

[54] PEPTIDES WITH SULFATE ESTER GROUPS

[75] Inventor: James D. Rosamond, Rochester, N.Y.

[73] Assignee: Fisons Corporation, Bedford, Mass.

[21] Appl. No.: 303,425

[22] Filed: Jan. 26, 1989

Related U.S. Application Data

[63] Continuation-in-part of Ser. No. 54,554, May 27, 1987, abandoned, which is a continuation-in-part of Ser. No. 932,119, Nov. 18, 1986, abandoned, which is a continuation-in-part of Ser. No. 810,948, Dec. 19, 1985, abandoned.

[51] Int. Cl.$^5$ .......................... A61K 37/02; C07K 7/06
[52] U.S. Cl. ........................................ 514/16; 514/15; 530/327; 530/328; 530/329
[58] Field of Search ...................... 530/327, 328, 329; 514/213, 16, 15

[56] References Cited

U.S. PATENT DOCUMENTS

| | | | |
|---|---|---|---|
| 3,705,140 | 12/1972 | Bernardi et al. | 260/112.5 |
| 3,839,315 | 10/1974 | Ondetti et al. | 260/112.5 |
| 3,892,726 | 7/1975 | Ondetti et al. | 530/328 |
| 4,351,829 | 9/1982 | Zetler et al. | 514/15 |
| 4,490,364 | 12/1984 | Rivier et al. | 424/177 |
| 4,517,180 | 5/1985 | Yanaihara et al. | 514/16 |
| 4,530,836 | 7/1985 | Yanaihara et al. | 514/16 |
| 4,769,445 | 9/1988 | Comstock et al. | 530/333 |
| 4,808,701 | 2/1990 | Danho et al. | 530/321 |

FOREIGN PATENT DOCUMENTS

| | | |
|---|---|---|
| 0107860 | 5/1984 | European Pat. Off. |
| 0161468 | 11/1985 | European Pat. Off. |
| 1584669 | 2/1981 | United Kingdom |

OTHER PUBLICATIONS

J. Med. Chem. 23, pp. 82–85 (1980).
Chemical Abstract 104:225218t (Jun. 23, 1986), abstracting Japanese patent appln. 60/194,000 (Oct. 2, 1985).
Chemical Abstract 102:160854j (May 13, 1985), abstracting Taylor et al., Am. J. Physiol. 248 (3, Pt. 1) (1985).
Chemical Abstract 97:139403e (Oct. 25, 1982), abstracting Stacher et al., Peptides 3 (4)607–12 (1982).
Chem. Abs. 104:184847b (May 26, 1986) abstracting Japanese Patent Application 60/197699 (Oct. 7, 1985).
Chem. Abs. 102:132473r (Apr. 15, 1985), abstracting European Patent Application 124,420 (Nov. 7, 1984).
Chem. Abs. 89:110419p (Sep. 25, 1978), abstracting German Offen. 2,751,016 (Jun. 1, 1978).
Chem. Abs. 97:216686d (Dec. 20, 1982), abstracting Bodanszky et al., Pept., Proc. Eur. Pept. Symp. 16th, 1980 (Pub. 1981) 93–8.
A. Anastasi, et al., "Synthetic Peptides Related to Caerulein, Note, 1", *Experientia*, 24, pp. 771–773 (1968).
M. A. Ondetti, et al., "CCK-PZ Recent Developments", *Digestive Diseases*, 15, pp. 149–156 (1970).
J. Pluscec, et al., "Synthesis of Analogs of the C-Terminal Octapeptide of CCK-PZ, Structure-Activity Relationship", *J. Med. Chem.* 13, pp. 349–352 (1970).
Gibbs, et al., "CCK Decreases Food Intake in Rats", *J. Comp. Physiol. Psychol.*, 84, 488–495 (1973).
Rubin, et al., "Some Biological Characteristics of CCK-PZ and Synthetic Analogs", *Nobel Symp.*, 18, (Front. Gastrointest. Horm. Res.), pp. 41–58 (Pub. 1973).
J. S. Morley, "Structure-Activity Relations in GI Hormones", Nobel Symp., 16, (Front. Gastrointest. Horm. Res.), pp. 143–149 (Pub. 1973).
L. Bernardi, et al., "Synthetic Peptides Related to Caerulein., Note 2", *Experientia*, 28, pp. 7–9 (1972).
L. Negri, et al., "Action of Caerulein and Caerulein-Like Peptides on 'Short-Circuit Current' and Acid Secretion in the Isolated Gastric Mucosa of Amphibians", *Naunyn-Schmiedeberg's Arch. Pharmacol.*, 277, pp. 401–412 (1973).
A. Agosti, et al., "Inhibitory Effects of a Caerulein-Like Peptide on Human Gastric Secretion", *European J. Pharmacol.*, 28, pp. 193–195 (1976).
M. Bodanszky, "CCK-PZ. 4, Synthesis and Properties of a Biologically Active Analog of the C-Terminal Heptapeptide with 2-Amino-6-hydroxyhexanoic Acid (HAhx) Sulfate Replacing Tyrosine Sulfatge", *J. Med. Chem.*, 21, pp. 1030–1035 (1978).
D. Gillessen, et al., "Synthesis and Biological Activity of Methoxinine-Analogs of the C-Terminal Octapeptide of CCK-PZ", *Int. J. Peptide Protein Res.*, 13, pp. 130–135 (1979).
R. D. Meyer, et al., "Biological Activity of the C-Terminal Octapeptide of CCK, of Three of Its Analogs and of Caerulein in the Dog", *Experientia*, 36, pp. 434–436 (1980).
M. Bodanszky, et al., "CCK-PZ. 5, Hormonally Active Desamino Derivative of TyrSE-Met-Gly-Trp-Met-Asp-Phe-NH$_2$,".
H. M. Rajh, et al., "Tryptophan Replacement in the C-Terminal Octapeptide of CCK-PZ", *Int. J. Peptide Protein Res.*, 15, pp. 200–210 (1980).
M. Bodanszky, et al., "CCK-PZ 6, Synthesis and Properties of the N-Acetyl-derivative of CCK 27–33", *Int. J. Peptide Protein Res.*, 16, pp. 402–411 (1980).
S. M. Anika, et al., "CCK and Satiety in Pigs", *Am. J. Physiol.* 240 (Regulatory Integrative Comp. Physiol. 9), pp. R310–R318 (1981).

(List continued on next page.)

Primary Examiner—Lester L. Lee
Assistant Examiner—Marshall S.
Attorney, Agent, or Firm—Seidel, Gonda, Lavorgna & Monaco

[57] ABSTRACT

Novel peptides having sulfate ester groups and containing 6 to 9 amino acids; possessing feeding inhibition properties and capable of stimulating the contraction of the gallbladder. Also methods of treating and preventing obesity in which these novel peptides or other specified peptides can be used.

74 Claims, No Drawings.

OTHER PUBLICATIONS

J. Martinez, et al., "Synthesis and Some Pharmacological Properties of Z-TyrSE-Met-Gly-Trp-Met-Asp(-Phe-NH$_2$)-OH, a 32-beta-Aspartyl Analog of CCK-PZ 27-33", *J. Med. Chem.*, 25, pp. 589-593 (1982).

G. Zetler, "Ceruletide, Ceruletide Analogs and CCK-8: Effects on Motor Behavior, Hexobarbital-Induced Sleep and Harman-Induced Confulsions", *Peptides*, 3, pp. 701-707 (1982).

B. Penke, et al., "Synthesis of Potent Heptapeptide Analogs of CCK", *J. Med. Chem.*, 27, pp. 845-849 (Jul. 1984).

G. Gacel, et al., "Investigation of Receptors Heterogeneity Using CCK-8 Analogs Designed from NMR Studies", In *Peptides (1985)*, pp. 383-385 (publication date, Jan. 30, 1985).

N. Yanaihara, et al., "Synthetic and Structure-function studies on C-terminal Segments of CCK and Gastrin", In *Peptides 1985*, pp. 373-378 (publicate date, Jan. 30, 1985).

C. Yanaihara, et al., "Dissociation of pancreczymin (PZ) activity from cholecystokinin (CCK) activity of N.alpha-carboxyacyl CCK-7 and CCK-8 analogs with a substituted glycine" *Biomed. Res.* 6(2), pp. 111-115 (Mar., 1985).

K. Treptow, et al., "Wirkung von Desaminoocta-Pankreczymin auf die lokomoterische Aktivitat von Ratten (The influence of desaminooctapancreczymin on the locomotor activity of rats)", *Biomed. Biochim. Acta.* 44(10), pp. 1541-1547, (Oct., 1985).

J. Gibbs, et al., "Cholecystokinin Elicits Satiety in Rats with Open Gastric Fistulas", *Nature*, 245, pp. 323-325 (1973).

Spatola et al., "Backbone Modified CCK Analogs and Their Behavior Toward Proteolytic Enzymes"(Poster), *Tenth American Peptide Symposium*, May 23-28, 1987, St. Louis, Mo.

J. Rosamond et al., "Structural Requirements for the Satiety Effect of CCK-8", in *Peptides; Chemistry and Biology, Proceedings of the Tenth American Peptide Symposium*, May 23-28, 1987, St. Louis, Mo., pp. 610-612 (1988).

J. Blosser et al., "Comparative Effects of CCK-8 and Analogs on Anorectic Activity and in vitro Gall Bladder Contractin," (Poster), *Society for Neuroscience*, Nov. 16-21, 1987, New Orleans, La.

Derwent Abstract 880294147/42, abstracting European Patent Appln. 285,061 (Oct. 5, 1988).

PEPTIDES WITH SULFATE ESTER GROUPS

This application is a continuation-in-part of application Ser. No. 054,554, filed May 27, 1987, now abandoned, which is a continuation-in-part of application Ser. No. 932,119, filed Nov. 18, 1986, now abandoned, which is a continuation-in-part of application Ser. No. 810,948, filed Dec. 19, 1985, now abandoned.

BACKGROUND OF THE INVENTION

This invention concerns sulfate ester containing peptides possessing feeding inhibition properties and capable of stimulating the contraction of the gallbladder. These peptides have 6 to 9 amino acids. They all differ structurally, however, from two similarly sized peptides known to have feeding inhibition properties: CCK-8, which has the structure, Asp-Tyr(SO$_3$H)-Met-Gly-Trp-Met-Asp-Phe-NH$_2$, and ceruletide, which has the structure, Glp-Gln-Asp-Tyr(SO$_3$H)-Thr-Gly-Trp-Met-Asp-Phe-NH$_2$. The peptides of this invention are not found in nature but, rather, must be synthesized.

SUMMARY OF THE INVENTION

The compounds of the invention are peptides of the formula (1)

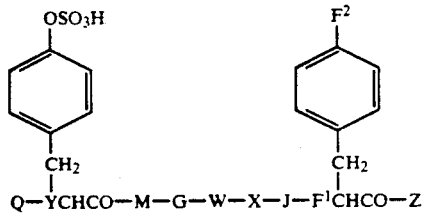

wherein

Q is H, H-Asp, H-βAsp, H-DAsp, H-MeAsp, For, Ac, Suc, desQ, or R$^1$R$^2$CHOCO,

Y is H, (S)-NH, (R)-R$^3$N, or (S)-R$^3$N,

M is Met, DMet, MeMet, MetO, Ahx, DAhx, MeAhx, Leu, MeLeu, Pro, Ile, MeIle, or Lys,

G is Gly, DAla, Pro or Sar,

W is Trp, MeTrp or Nal,

X is Met, MeMet, MetO, Ahx, MeAhx, Leu, MeLeu, Ile, MeIle, Pro, or Lys,

J is Asp, DAsp, MeAsp, or Asn,

F$^1$ is (S)-NH, (S)-R$^4$N, or (R)-R$^4$N,

F$^2$ is H, Cl, I, Br, F, NO$_2$, NH$_2$, R$^5$, or OR$^6$,

Z is NH$_2$, NHR$^7$ or NR$^7$R$^8$,

R$^1$ and R$^2$ are independently H or lower alkyl,

R$^3$, R$^4$, and R$^5$ are lower alkyl,

R$^6$ is H or lower alkyl, and

R$^7$ and R$^8$ are lower alkyl, and pharmaceutically acceptable salts thereof, provided that (1) Q is desQ when Y is H, (2) F$^2$ is not H if, in the same peptide, Q is H-Asp or Ac, Y is (S)-NH, M is either Met, MetO, Ahx or Leu, X is either Met, MetO, Ahx or Leu, G is Gly, DAla or Pro, W is Trp, J is Asp, F$^1$ is (S)-NH, and Z is NH$_2$, (3) F$^2$ is not H if, in the same peptide, Q is H, H-βAsp or For, Y is (S)-NH, M is Met, Ahx or Leu, G is Gly, W is Trp, X is Met, Ahx or Leu, J is Asp, F$^1$ is (S)-NH, and Z is NH$_2$, (4) F$^2$ is not H if, in the same peptide, Y is H, M is Met, X is Met, G is Gly, W is Trp, J is Asp, F$^1$ is (S)NH, and Z is NH$_2$, and (5) F$^2$ is not H if, in the same peptide, Q is Suc, Y is (S)-NH, M is Met, X is Met, G is Gly or DAla, W is Trp, J is Asp, F$^1$ is (S)-NH or (S)-R$^4$N, and Z is NH$_2$.

The invention is also a process of making the peptides of the invention.

The invention is also methods of treating obesity and preventing obesity, respectively; each such method comprising the administration, by either an intraperitoneal, intravenous, intramuscular, subcutaneous or intranasal route, to a mammal in need of such treatment, of a peptide of the formula (1)

wherein

Q is H, H-Asp, H-βAsp, H-DAsp, H-MeAsp, For, Ac, Suc, desQ, H-Arg-Asp, Glp-Asp, Glp-Glu, Glp-Gln, Suc-Asp, Glt-Asp, Pht-Asp, R$^9$CO-Asp, Boc-Asp, Cbz-Asp, H-Abu, H-Ala, Boc, Cbz, or R$^1$R$^2$CHOCO, Y is H, (S)-NH, (R)-R$^3$N, or (S)-R$^3$N, M is Met, DMet, MeMet, MetO, Ahx, DAhx, MeAhx, Leu, MeLeu, Pro, Ile, MeIle, Lys, Thr, Abu, Val, Mox, Gly, Phe, Tyr, or Trp, G is Gly, DAla, Sar, DTrp, Pro, or βAla, W is Trp, MeTrp, Nal, DTrp, Trp(Me), Trp(5-F), or Trp(6-F), X is Met, MeMet, MetO, Ahx, MeAhx, Leu, MeLeu, Ile, MeIle, Pro, Lys, DMet, Abu, or Mox, J is Asp, DAsp, MeAsp, βAsp, or Asn, F$^1$ is (S)-NH, (S)-R$^4$N, (R)-NH or (R)-R$^4$N, F$^1$ is H, Cl, I, Br, F, NO$_2$, NH$_2$, R$^5$, or OR$^6$, Z is NH$_2$, NHR$^7$ or NR$^7$R$^8$, R$^1$ and R$^2$ are independently H or lower alkyl, R$^3$, R$^4$, and R$^5$ are lower alkyl, R$^6$ is H or lower alkyl, and R$^7$, R$^8$ and R$^9$ are lower alkyl, and pharmaceutically acceptable salts thereof, provided that (1) Q is desQ when Y is H, and (2) F$^2$ is not H if, in the same peptide, Q is H-Asp, Y is (S)-NH, M is Met, X is Met, G is Gly or Pro, W is Trp, J is Asp, F$^1$ is (S)-NH, and Z is NH$_2$.

In its first subgeneric aspect, the invention is defined as compounds of the invention with the exception that it is further limited so that Q is H, H-Asp, H-βAsp, For, Ac, Suc, desQ, or R$^1$R$^2$CHOCO;

Y is H, (S)-NH, or (S)-R$^3$N

M is Met, MeMet, Ahx, MeAhx, Leu, MeLeu, Ile, MeIle, or Pro;

G is Gly or DAla;

W is Trp;

X is Met, MeMet, Ahx, MeAhx, Leu, MeLeu, Ile, MeIle, or Pro;

J is Asp;

F$^1$ is (S)-NH or (S)-R$^4$N;

F$^2$ is H, Cl, NO$_2$, NH$_2$, R$^5$ or OR$^6$; and

Z is NH$_2$.

In a second subgeneric aspect, the invention is defined as in its first subgeneric aspect with the exception that it is further limited so that M is neither MeMet, MeAhx, MeLeu nor MeIle, and X is neither MeMet, MeAhx, MeLeu, nor MeIle.

Compounds with increased feeding inhibition activity over a 3-hour feeding period as compared to CCK-8 are:

A peptide of the formula

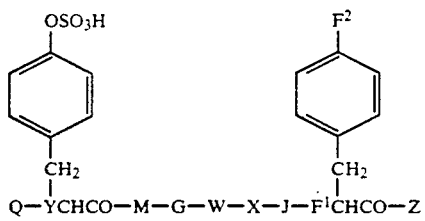

wherein
Q is H-βAsp, For, Suc, desQ, or $R^1R^2$CHOCO,
Y is H or (S)-NH,
M is Met, Ahx, Leu, or Ile,
G is Gly,
W is Trp,
X is Met, Ahx, Leu, or Ile,
J is Asp,
$F^1$ is (S)-NH or (S)-$R^4$N,
$F^2$ is H, $NO_2$, $R^5$, or $OR^6$,
Z is $NH_2$
$R^1$ and $R^2$ are independently H or lower alkyl,
$R^3$, $R^4$, $R^5$, and $R^6$ are lower alkyl, and pharmaceutically acceptable salts thereof, provided that
  (1) Q is desQ when Y is H,
  (2) $F^2$ is not H if, in the same peptide, Q is H-βAsp, or For, Y is (S)-NH, M is either Met, Ahx, or Leu, X is either Met, Ahx, or Leu, and $F^1$ is (S)-NH,
  (3) $F^2$ is not H if, in the same peptide, Y is H, M is Met, X is Met, and $F^1$ is (S)-NH,
  (4) $F^2$ is not H if, in the same peptide, Q is Suc, Y is (S)-NH, M is Met, X is Met, and $F^1$ is (S)-NH or (S)R $R^4$N.

In additional subgeneric aspects of the invention, the method of treating obesity or the method of preventing obesity is further limited to the administration of either the compounds of the invention or the compounds identified in the first or second generic aspects of the invention.

In a closely related invention, the compounds of the invention have Y as (R)-NH with the additional proviso that $F^2$ is not H if, in the same peptide, Q is H-Asp, M and X are Ile, G is Gly, W is Typ, J is Asp, $F^1$ is (S)-NH, and Z is $NH_2$ so that compounds of this related invention are peptides of the formula (1) wherein
Q is H, H-Asp, H-βAsp, H-DAsp, H-MeAsp, For, Ac, Suc, desQ, or $R^1R^2$CHOCO,
Y is (R)-NH,
M is Met, DMet, MeMet, MetO, Ahx, DAhx, MeAhx, Leu, MeLeu, Pro, Ile, MeIle, or Lys,
G is Gly, DAla, Pro or Sar,
W is Trp, MeTrp or Nal,
X is Met, MeMet, MetO, Ahx, MeAhx, Leu, MeLeu, Ile, MeIle, Pro, or Lys,
J is Asp, DAsp, MeAsp, or Asn,
$F^1$ is (S)-NH, (S)-$R^4$N, or (R)-$R^4$N,
$F^2$ is H, Cl, I, Br, F, $NO_2$, $NH_2$, $R^5$, or $OR^6$,
Z is $NH_2$, $NHR^7$ or $NR^7R^8$,
$R^1$ and $R^2$ are independently H or lower alkyl,
$R^3$, $R^4$, and $R^5$ are lower alkyl,
$R^6$ is H or lower alkyl, and
$R^7$ and $R^8$ are lower alkyl, and pharmaceutically acceptable salts thereof, provided that (1) $F^2$ is not H if, in the same peptide, Q is H-Asp, Asp, M and X are Ile, G is Gly, W is Trp, J is Asp, $F^1$ is (S)-NH and Z is $NH_2$.

DETAILED DESCRIPTION

Definitions

"lower alkyl" contains 1 to 6 carbon atoms.

(R) and (S) refer to the absolute configurations, about the adjacent methine carbon. When Y is (S)-NH, then

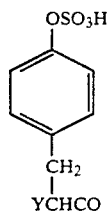

is of the L-configuration and when Y is (R)-NH, then

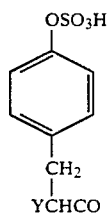

is of the D-configuration. Similarly, when $F^1$ is (S)-NH or (R)-NH, then

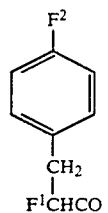

is of the L or D-configuration, respectively.

All optically active amino acids are of the L-configuration unless otherwise indicated.

The H in H-Asp, H-βAsp, H-DAsp, H-MeAsp, H-Arg, H-Abu, and H-Ala stands for hydrogen.

DesQ, which arises when Y is H, means that there is no Q.

$R^1R^2$CHOCO is the formula

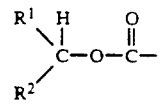

Hpp($SO_3H$) is the formula

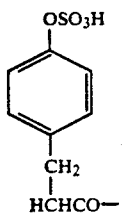

Each claim to a compound includes its pharmaceutically acceptable base addition salts. Base addition salts include those derived from both organic and inorganic bases, such as, for example, ammonia, sodium hydroxide, calcium hydroxide, barium hydroxide, tetraethylammonium hydroxide, ethylamine, diethylamine, triethylamine, and the like.

In an alternative representation to formula (1), used for purposes of brevity, peptides are also represented in accordance with conventional representation, for example, H-Asp-DTyr(SO$_3$H)-Met-Gly-Trp-Met-Asp-Phe-NH$_2$, which stands for the compound of formula (1) in which Q is H-Asp, Y is (R)-NH, M is Met, G is Gly, W is Trp, X is Met, J is Asp, F$^1$ is (S)-NH, F$^2$ is H, and Z is NH$_2$.

When amino acids, peptides, protecting groups, active groups, etc. are represented by symbols in this specification and appended claims, usual symbols as defined by IUPAC and IUB or as used in the art are employed. Examples of symbols are given below.

| | |
|---|---|
| Abu | 2-aminobutyric acid |
| Ac | acetyl |
| Ahx | 2-aminohexanoic acid |
| Aib | 2-aminoisobutyric acid |
| Ala | alanine |
| Arg | arginine |
| Asn | asparagine |
| Asp | aspartic acid |
| βAsp | beta-aspartic acid |
| Boc | tert-butyloxycarbonyl |
| BrCH$_2$—Pam | 4-(bromomethyl)phenylacetamidomethyl |
| Cbz | carbobenzoxy |
| Cys(Me) | S-methylcysteine |
| DAla | D-alanine |
| DAhx | D,2-aminohexanoic acid |
| DAsp | D-aspartic acid |
| DMet | D-methionine |
| DPhe | D-phenylalanine |
| DPhe—NH$_2$ | D-phenylalanine amide |
| DTrp | D-tryptophan |
| DTyr | D-tyrosine |
| EtOCO | ethyloxycarbonyl |
| EtPhe | N-ethylphenylalanine |
| EtPhe—NH$_2$ | N-ethylphenylalanine amide |
| Fmoc | 9-fluorenylmethyloxycarbonyl |
| For | formyl |
| Gln | glutamine |
| Glp | pyroglutamyl |
| Glu | glutamic acid |
| Glt | HOOC(CH$_2$)$_3$CO— |
| Gly | glycine |
| His | histidine |
| Hpp | 3-(4-hydroxyphenyl)propionyl |
| Hpp(SO$_3$H) | 3-(O-sulfo-4-oxyphenyl)propionyl |
| iBuOCO | isobutyloxycarbonyl |
| Ile | isoleucine |
| Leu | leucine |
| Lys | lysine |
| MeAhx | N-methyl-2-aminohexanoic acid |
| MeAsp | N-methylaspartic acid |
| MeLeu | N-methylleucine |
| MeIle | N-methylisoleucine |
| MeMet | N-methylmethionine |

| | -continued |
|---|---|
| MeOCO | methyloxycarbonyl |
| MePhe | N-methylphenylalanine |
| MePhe—NH$_2$ | N-methylphenylalanine amide |
| Met | methionine |
| MetO | methionine sulfoxide |
| MeTrp | N-α-methyltryptophan |
| MeTyr | N-methyltyrosine |
| MeTyr(Me) | N,O-dimethyltyrosine |
| MeTyr(Me)—NH$_2$ | N,O-dimethyltyrosine amide |
| Mox | methoxinine |
| Nal | 3-(2-naphthyl)alanine |
| OBt | 1-benzotriazolyl ester |
| OCH$_2$—Pam | 4-(oxymethylphenyl)acetamidomethyl |
| OSu | succinimidyloxy ester |
| OtBu | tert-butyl ester |
| Phe | phenylalanine |
| Phe—NH$_2$ | phenylalanine amide |
| Phe—NHEt | phenylalanine ethylamide |
| Phe—NHMe | phenylalanine methylamide |
| Phe—N(Et)$_2$ | phenylalanine diethylamide |
| Phe—N(Me)$_2$ | phenylalanine dimethylamide |
| Phe—OH | phenylalanine acid |
| Phe(4-Cl) | 3-(4-chlorophenyl)alanine |
| Phe(4-Cl)—NH$_2$ | 3-(4-chlorophenyl)alanine amide |
| Phe(4-Me) | 3-(4-methylphenyl)alanine |
| Phe(4-Me)—NH$_2$ | 3-(4-methylphenyl)alanine amide |
| Phe(4-NO$_2$) | 3-(4-nitrophenyl)alanine |
| Phe(4-NO$_2$)—NH$_2$ | 3-(4-nitrophenyl)alanine amide |
| Phe(4-NH$_2$) | 3-(4-aminophenyl)alanine |
| Phe(4-NH$_2$)—NH$_2$ | 3-(4-aminophenyl)alanine amide |
| Pht | 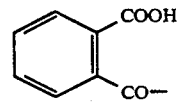 |
| Pro | proline |
| PrOCO | n-propyloxycarbonyl |
| resin | polystyrene |
| Sar | sarcosine |
| Ser | serine |
| Suc | HOOC(CH$_2$)$_2$CO— |
| tBu | tert-butyl |
| Thr | threonine |
| Trp | tryptophan |
| Trp(5-F) | 5-fluorotryptophan |
| Trp(6-F) | 6-fluorotryptophan |
| Trp(Me) | 1-methyltryptophan |
| Tyr | tyrosine |
| Tyr—NH$_2$ | tyrosine amide |
| Tyr(Me) | O-methyltyrosine |
| Tyr(Me)—NH$_2$ | O-methyltyrosine amide |
| Tyr(SO$_3$H) | O-sulfotyrosine |
| Tyr(SO$_3$H)—NH$_2$ | O-sulfotyrosine amide |
| Val | valine |

Preferred Compounds

The preferred compounds of the invention are those that during the 0.5 hour feeding period inhibited feeding by 48–100% when administered at 30 μg/kg in the test described under "Utility" below. (See Table 2 below.)

The most preferred compound, at the time of filing this continuation-in-part application, from the point of view of gallbladder contraction, is the compound Hpp(SO$_3$H)-Met-Gly-Trp-Met-Asp-MePhe-NH$_2$.

Particularly preferred compounds, at the time of filing this continuation-in-art application, from the point of feeding inhibition, were those that during the 0.5 hour feeding period inhibited feeding by 20–72% when administered at 0.3 μg/kg in the test described under "Utility" below. They are:

H-DAsp-Tyr(SO$_3$H)-Met-Gly-Trp-Met-Asp-Phe-NH$_2$
iBuOCO-Tyr(SO$_3$H)-Met-Gly-Trp-Met-Asp-Phe-NH$_2$
Suc-Tyr(SO$_3$H)-Ahx-Gly-Trp-Ahx-Asp-Phe-NH$_2$

H-βAsp-Tyr(SO₃H)-Met-Gly-Trp-Met-Asp-MePhe-NH₂
H-DAsp-Tyr(SO₃H)-Met-Gly-Trp-Met-Asp-MePhe-NH₂
For-Tyr(SO₃H)-Met-Gly-Trp-Met-Asp-MePhe-NH₂
iBuOCO-Tyr(SO₃H)-Met-Gly-Trp-Met-Asp-MePhe-NH₂
Hpp(SO₃H)-Met-Gly-Trp-Met-Asp-MePhe-NH₂
PrOCO-Tyr(SO₃H)-Met-Gly-Trp-Met-Asp-Phe-NH₂
EtOCO-Tyr(SO₃H)-Met-Gly-Trp-Met-Asp-Phe-NH₂
MeOCO-Tyr(SO₃H)-Met-Gly-Trp-Met-Asp-Phe-NH₂
H-βAsp-Tyr(SO₂H)-Met-Gly-Trp-Met-Asp-Phe-NH₂
Suc-Tyr(SO₃H)-Met-Gly-Trp-Met-Asp-Phe-NH₂
Hpp(SO₃H)-Met-Gly-Trp-Met-Asp-Phe-NH₂
H-Asp-Tyr(SO₃H)-Leu-Gly-Trp-Leu-Asp-Phe-NH₂
For-Tyr(SO₃H)-Met-Gly-Trp-Met-Asp-Phe-NH₂
Suc-Tyr(SO₃H)-Ahx-Gly-Trp-Ahx-Asp-MePhe-NH₂
iBuOCO-Tyr(SO₃H)-Ahx-Gly-Trp-Ahx-Asp-MePhe-NH₂
Hpp(SO₃H)-Ahx-Gly-Trp-Ahx-Asp-MePhe-NH₂
iBuOCO-Tyr(SO₃H)-Ahx-Gly-Trp-Ahx-Asp-Phe-NH₂
Hpp(SO₃H)-Ahx-Gly-Trp-Ahx-Asp-Phe-NH₂
Suc-Tyr(SO₃H)-Met-Gly-Trp-Met-Asp-MePhe-NH₂
H-DAsp-Tyr(SO₃H)-Ile-Gly-Trp-Ile-Asp-MePhe-NH₂
For-Tyr(SO₃H)-Ile-Gly-Trp-Ile-Asp-MePhe-NH₂
Suc-Tyr(SO₃H)-Ile-Gly-Trp-Ile-Asp-MePhe-NH₂
iBuOCO-Tyr(SO₃H)-Ile-Gly-Trp-Ile-Asp-MePhe-NH₂
Hpp(SO₃H)-Ile-Gly-Trp-Ile-Asp-MePhe-NH₂
Suc-Tyr(SO₃H)-Ile-Gly-Trp-Ahx-Asp-MePhe-NH₂
Hpp(SO₃H)-Ile-Gly-Trp-Ahx-Asp-MePhe-NH₂

The compound, EtOCO-Tyr(SOsH)-Met-Gly-Trp-Met-Asp-Phe-NH₂, was the one that inhibited feeding by 72% at 0.3 µg/kg.

The most preferred compounds, at the time of filing this continuation-in-part application, from the point of view of feeding inhibition, were those that during the 3 hour feed period inhibited feeding by 50-90% when administered at 3 µg/kg in the test described under "Utility" below. They are:
iBuOCO-Tyr(SO₃H)-Met-Gly-Trp-Met-Asp-Phe-NH₂
Suc-Tyr(SO₃H)-Ahx-Gly-Trp-Ahx-Asp-Phe-NH₂
For-Tyr(SO₃H)-Met-Gly-Trp-Met-Asp-MePhe-NH₂
iBuOCO-Tyr(SO₃H)-Met-Gly-Trp-Met-Asp-MePhe-NH₂
Hpp(SO₃H)-Met-Gly-Trp-Met-Asp-MePhe-NH₂
PrOCO-Tyr(SO₃H)-Met-Gly-Trp-Met-Asp-Phe-NH₂
Suc-Tyr(SO₃H)-Met-Gly-Trp-Met-Asp-Phe-NH₂
Suc-Tyr(SO₃H)-Ahx-Gly-Trp-Ahx-Asp-MePhe-NH₂
iBuOCO-Tyr(SO₃H)-Ahx-Gly-Trp-Ahx-Asp-MePhe-NH₂
Hpp(SO₃H)-Ahx-Gly-Trp-Ahx-Asp-MePhe-NH₂
iBuOCO-Tyr(SO₃H)-Ahx-Gly-Trp-Ahx-Asp-Phe-NH₂
Hpp(SO₃H)-Ahx-Gly-Trp-Ahx-Asp-Phe-NH₂
Suc-Tyr(SO₃H)-Met-Gly-Trp-Met-Asp-MePhe-NH₂
For-Tyr(SO₃H)-Ile-Gly-Trp-Ile-Asp-MePhe-NH₂
Suc-Tyr(SO₃H)-Ile-Gly-Trp-Ile-Asp-MePhe-NH₂
iBuOCO-Tyr(SO₃H)-Ile-Gly-Trp-Ile-Asp-MePhe-NH₂
Hpp(SO₃H)-Ile-Gly-Trp-Ile-Asp-MePhe-NH₂
Suc-Tyr(SO₃H)-Ile-Gly-Trp-Ahx-Asp-MePhe-NH₂
Hpp(SO₃H)-Ile-Gly-Trp-Ahx-Asp-MePhe-NH₂

The compound, Suc-Tyr(SO₃H)-Ile-Gly-Trp-Ahx-Asp-MePhe-NH₂, was the one that inhibited feeding by 90% at 3 µg/kg during the 3 hour feeding period.

Preparation of Peptides

The novel sulfate ester peptides of this invention and the novel intermediates thereof may be prepared by methods well known to the art, for example, they may be prepared by combining individual amino acids on a solid phase resin on a step-by-step basis, or alternatively, by combining groups of amino acids on a solid phase resin to yield the desired peptidyl-resin intermediate. Such additions, as is known, are accomplished by protecting the amino group of the amino acid or group of amino acids by converting it to, for example, its tert-butyloxycarbonyl (Boc) or 9-fluorenylmethyloxycarbonyl (Fmoc) derivative, and then activating the carboxylic group of such amino acid or group of amino acids by converting it, for example, to its 1-hydroxybenzotriazole (HOBt) or N-hydroxysuccinimide (HOSu) ester derivative. Such a protected-activated intermediate is then allowed to react with an amino acid-resin or peptidyl-resin with a free amino group, thus extending the peptide chain to provide the peptidyl-resin of formula 2, wherein Pg is a suitable protecting group, for example, Boc or Fmoc.

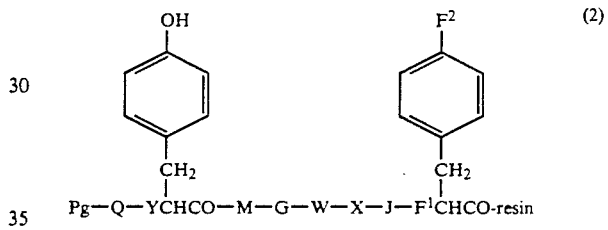

The phenolic OH group within formula (2) is converted to a sulfate ester by the use of a usual sulfating agent, such as sulfur trioxide pyridine complex. More specifically, the reaction is conducted, for example, by suspending a peptidyl-resin of formula 2 in dimethylformamide (DMF), pyridine or like solvent, and adding sulfur trioxide pyridine complex in about 10-40 molar excess to provide the sulfated peptidyl-resin of the formula 3.

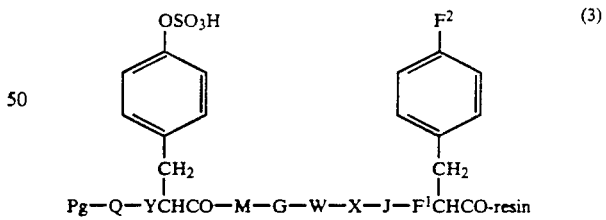

Since the sulfate ester containing peptide end-products of this invention are C-terminal amides, the chemical link which connects the peptide chain to the resin must be such that its cleavage with suitable reagents readily provides amides. Due to the lability of the sulfate ester group to strong acids (for example, liquid hydrogen fluoride), the peptidyl-resin linkage may be cleavable with either weaker acids (for example, brief treatment with trifluoroacetic acid, TFA) and/or nucleophiles (for example, ammonia, amines, hydroxide, and alkoxides). Among the suitable resin derivatives may be mentioned oxymethyl-polystyrene, 4-(oxymethylphenyl)-(CH₂)ₙCO-aminomethyl-polystyrene (n=0-3) and 4-(oxy-methylphenyl)oxymethyl-polystyrene. Similarly substituted polyacrylamide resins are equally well suited as the above polystyrene based resins. For the purposes of this invention the 4-(oxymethylphenyl)CHCO-aminomethyl-polystyrene [herein referred to as 4-(oxymethylphenyl)acetamidomethylpolystyrene or OCH$_2$-Pam-resin] is best suited for the generation of peptide amides. Thus, this invention describes a process for the synthesis of sulfated peptidyl-OCH$_2$-Pam-resins of formula (4), wherein the resin is polystyrene (the term "polystyrene" includes copolymers with minor amounts, usually 1%, of unsaturated monomers such as divinylbenzene).

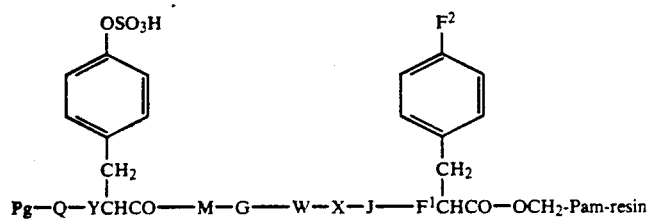

Pg—Q—YCHCO——M—G——W—X—J——F$^1$CHCO—OCH$_2$-Pam-resin

In forming peptide sequences of this invention, the amino functions may be protected by commonly used amino protecting groups such as Boc, Fmoc, (4-methoxybenzyl)oxycarbonyl, 2-nitrophenylsulfenyl, and so forth. The Boc and Fmoc protecting groups are preferred. The carboxyl and hydroxyl protecting group may be methyl, tert-butyl (tBu), benzyl, 4-methoxybenzyl and so forth. The tBu group is preferred.

The amino acid defined by the F$^1$ and F$^2$ groups of formula 4 may be attached to the OCH$_2$-Pam-resin in several ways. (a) For example, Boc-protected phenylalanine, wherein F$^1$ is (S)-NH and F$^2$ is H may be reacted with a suitable 4-(bromomethyl)phenylacetate ester (for example, phenacyl ester) and processed further to provide Boc-Phe(4-oxymethylphenyl)acetic acid which may be coupled to aminomethyl-polystyrene to provide Boc-Phe-(4-oxymethylphenyl)acetamidomethylpolystyrene (Boc-Phe-OCH$_2$-Pam-resin). (b) Alternatively, 4-(bromomethyl)phenylacetic acid may be coupled to aminomethylpolystyrene to provide 4-(bromomethyl)-phenylacetamidomethylpolystyrene (BrCH$_2$-Pam-resin) which may be reacted with the cesium salt of Boc-Phe-OH to provide Boc-Phe-OCH$_2$-Pam-resin.

Among the suitable activating groups may be mentioned any combination of groups which causes the acid function of the amino acid to become more reactive, such as acid chlorides, mixed and symmetrical anhydrides, reaction product with carbodiimide (for example, dicyclohexylcarbodiimide, DCC), and active esters (for example, esters derived from HOBt, HOSu, 2- or 4-nitrophenol, and 2,4,5-trichlorophenol). The use of DCC and esters of HOBt and HOSu is particularly preferred from the standpoint of yield, lack of by-products, and consequent ease of purification.

The protecting groups are removed by known reactions such as treatment with dilute TFA (50% in dichloromethane, DCM) for Boc and/or tBu removal and treatment with dilute piperidine (20% in DMF) for Fmoc removal, to name a few, to provide the sulfated peptidyl-resin of the formula (5).

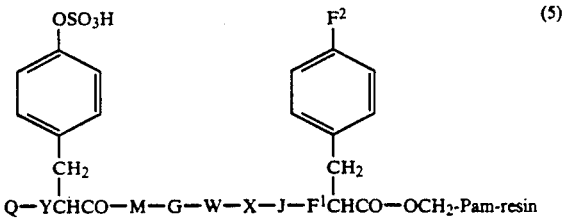

Q—YCHCO—M—G—W—X—J—F$^1$CHCO—OCH$_2$-Pam-resin

The sulfate ester containing peptides of formula 1 may be obtained by cleavage of the peptidyl-OCH$_2$-Pam-resin linkage of (5) with the appropriate reagent. The C-terminal sulfated peptide amides are derived, for example, by treatment of the sulfated peptidyl-resin of formula (5) with methanolic solutions of ammonia, alkylamines and dialkylamines.

An automatic peptide synthesizer was used for the solid phase synthesis of the sulfated peptide amides of this invention. The protocol of coupling onto aminomethyl-resin or peptidyl-OCH$_2$-Pam-resin (1 mmole of available nitrogen), deprotection, sulfation, cleavage, and product purification is set forth in Table 1.

Table 1. Protocol for solid phase synthesis of sulfated peptide amides (1 mmole scale). Each step volume is 50 ml unless otherwise indicated. All wash steps are repeated three times. Abbreviations: DCC, dicyclohexylcarbodiimide; DCM, dichloromethane; DIEA, N,N-diisopropylethylamine, DMF, dimethylformamide; HOBt, 1-hydroxybenzotriazole; TFA, trifluoroacetic acid.

TABLE 1

| Step | Reagent or Solvent | Purpose | Mix Time |
|---|---|---|---|
| 1 | DCM | Wash | 1 min |
| 2 | Go to Step 3, 5, or 8 | — | — |
| 3 | Add filtered, pre-activated (0° C., 1 hr) mixture of protected amino acid (or protected dipeptide, 3 mmole), HOBt (4.5 mmole), and DCC (3 mmole) in 1:4 DMF/DCM | Pre-activated DCC/HOBt coupling | 2-15 hr |
| 4 | Go to Step 10, 16, 21, or 26 | — | — |
| 5 | Add protected amino acid (or protected dipeptide, 3 mmole) and HOBt (4.5 mmole) in 30 ml 1:2 DMF/DCM then DCC (3 mmole) in 20 ml DCM | In situ activated DCC/HOBt coupling | 2-15 hr |
| 6 | 2-Propanol | Wash | 1 min |
| 7 | Go to Step 4 | — | — |
| 8 | Add active ester or anhydride (3 mmole) in DCM, DMF, or mixture thereof | Non DCC/HOBt activated coupling | 2-15 hr |
| 9 | Go to Step 4 | — | — |
| 10 | DCM | Wash | 1 min |
| 11 | Treat with 49:1:50 TFA/anisole/DCM | Boc and tBu removal | 30 min |

TABLE 1-continued

| Step | Reagent or Solvent | Purpose | Mix Time |
|---|---|---|---|
| 12 | DCM | Wash | 1 min |
| 13 | Treat with 1:19 DIEA/DCM | Neutralize | 1 min |
| 14 | DCM | Wash | 1 min |
| 15 | Go to Step 1, 16, 21, or 26 | — | — |
| 16 | DMF | Wash | 1 min |
| 17 | Treat with 1:4 piperidine/DMF | Fmoc removal | 3 min |
| 18 | Treat with 1:4 piperidine/DMF | Fmoc removal | 7 min |
| 19 | DMF | Wash | 1 min |
| 20 | Go to Step 15 | — | — |
| 21 | DMF | Wash | 1 min |
| 22 | 1:2 pyridine/DMF | Wash | 1 min |
| 23 | Add sulfur trioxide pyridine complex (40 mmole) in 60 ml 1:2 pyridine/DMF | Sulfation | 20–24 hr |
| 24 | DMF | Wash | 1 min |
| 25 | Go to Step 4 | — | — |
| 26 | Methanol | Wash | 1 min |
| 27 | Ammonia saturated (−20° C.) methanol or 20% methanolic amine (250 ml) | Resin cleavage | 2–5 day |
| 28 | Methanol | Wash | 1 min |
| 29 | Combine, concentrate filtrates from Steps 27-28 | Isolation | — |
| 30 | Chromatograph residue on column(s) of Amberlite XAD-2 (Rohm and Haas, 2.5 × 60 cm, methanol gradient 0.1 M in ammonia), Trisacryl M DEAE (LKB Inc., 2.5 × 47 cm, ammonium bicarbonate gradient), and/or P-40 ODS-3 (Whatman, 4.8 × 50 cm, methanol gradient 0.2% in ammonium acetate) | Purification | — |

The sulfate ester containing peptides of formula (1) thus prepared may be desalted and purified by the usual methods. For example, the product may be purified by ionexchange chromatography with use of Trisacryl M DEAE, DEAE-cellulose or the like, partition chromatography with use of Sephadex LH-20, Sephadex G-25 or the like, reverse phase chromatography with use of Amberlite XAD-2, ODS-silica gel or the like, normal phase chromatography with use of silica gel or the like, or high-performance liquid chromatography (HPLC).

Analogous procedures, wherein the reactions are carried out without the solid phase component (resin), are well known in the art and well suited to large scale production. [See e.g., U.S. Pat. No. 3,892,726].

Utility

The peptides of this invention have the ability to inhibit feeding activity in mammals. As a result they have utility in the prevention and treatment of obesity. Feeding inhibition activity can be demonstrated in rats as follows:

Male Sprague-Dawley rats (weighing 300–350 g) are individually caged and maintained on a 12 hr. light, dark cycle and trained for at least 14 days to feed during a three hr period of the dark cycle but not the 21 hours preceding that three hr period. The day of the study, rats are dosed intraperitoneally with saline (controls) or test compound (dissolved in saline; usually at a concentration of 0.3 to 300 micrograms of test compound per kg of rat weight). Food is introduced 10 minutes after administration of saline or test compound. Test compounds are deemed to be active if the test group consumes significantly less food than the saline controls during the feeding period, which ends either 0.5 or 3 hr after presentation of food. The % feeding inhibition for the ½ hr and 3 hr feeding periods obtained by administering a dose of 30 μg/kg of test compound is given in Table 2 for CCK-8 and various compounds of the invention. For example, the % feeding inhibition obtained with CCK-8 (first line of Table 2) was 70% for the ½ hr feeding period and 25% for the 3-hour period.

TABLE 2

| STRUCTURE | % FEEDING INHIBITION 0.5 hr–3 hr |
|---|---|
| H-Asp-Tyr(SO$_3$H)-Met-Gly-Trp-Met-Asp-Phe-NH$_2$ | 70–25 |
| H-DAsp-Tyr(SO$_3$H)-Met-Gly-Trp-Met-Asp-Phe-NH$_2$ | 99–40 |
| iBuOCO-Tyr(SO$_3$H)-Met-Gly-Trp-Met-Asp-Phe-NH$_2$ | 100–94 |
| H-Asp-DTyr(SO$_3$H)-Met-Gly-Trp-Met-Asp-Phe-NH$_2$ | 74–24 |
| H-Asp-Tyr(SO$_3$H)-DMet-Gly-Trp-Met-Asp-Phe-NH$_2$ | 17–IA |
| H-Asp-Tyr(SO$_3$H)-DAhx-Gly-Trp-Met-Asp-Phe-NH$_2$ | 14–17* |
| H-Asp-Tyr(SO$_3$H)-Met-Sar-Trp-Met-Asp-Phe-NH$_2$ | 55*–12* |
| H-Asp-Tyr(SO$_3$H)-Met-Gly-MeTrp-Met-Asp-Phe-NH$_2$ | 31–11 |
| H-Asp-Tyr(SO$_3$H)-Met-Gly-Nal-Met-Asp-Phe-NH$_2$ | 52*–20* |
| H-Asp-Tyr(SO$_3$H)-Met-Gly-Trp-Met-DAsp-Phe-NH$_2$ | 32–15* |
| H-Asp-Tyr(SO$_3$H)-Met-Gly-Trp-Met-Asn-Phe-NH$_2$ | 43*–17* |
| H-Asp-Tyr(SO$_3$H)-Met-Gly-Trp-Met-Asp-MePhe-NH$_2$ | 70–24 |
| H-Asp-Tyr(SO$_3$H)-Met-Gly-Trp-Met-Asp-MeTyr(Me)-NH$_2$ | 65–17 |
| H-Asp-Tyr(SO$_3$H)-Met-Gly-Trp-Met-Asp-Phe(4-NO$_2$)-NH$_2$ | 43–17 |
| H-Asp-Tyr(SO$_3$H)-Met-Gly-Trp-Met-Asp-Phe(4-Cl)-NH$_2$ | 54–28* |
| H-Asp-Tyr(SO$_3$H)-Met-Gly-Trp-Met-Asp-Phe(4-NH$_2$)-NH$_2$ | 27–IA |
| H-Asp-Tyr(SO$_3$H)-Met-Gly-Trp-Met-Asp-Tyr(Me)-NH$_2$ | 72*–10* |
| H-Asp-Tyr(SO$_3$H)-Met-Gly-Trp-Met-Asp-Phe-NHMe | 13*–IA |
| H-Asp-Tyr(SO$_3$H)-Met-Gly-Trp-Met-Asp-Phe-NHEt | 16–IA |
| H-Asp-Tyr(SO$_3$H)-Met-Gly-Trp-Met-Asp-Phe-N(Me)$_2$ | NT-NT |
| H-Asp-Tyr(SO$_3$H)-Met-Gly-Trp-Met-Asp-Phe-N(Et)$_2$ | NT-NT |
| H-βAsp-DTyr(SO$_3$H)-Met-Gly-Trp-Met-Asp-Phe-NH$_2$ | 47–33* |
| H-DAsp-DTyr(SO$_3$H)-Met-Gly-Trp-Met-Asp-Phe-NH$_2$ | 53–15 |
| Suc-DTyr(SO$_3$H)-Met-Gly-Trp-Met-Asp-Phe-NH$_2$ | 82–60 |
| H-Asp-Tyr(SO$_3$H)-Ile-Gly-Trp-Ile-Asp-Phe-NH$_2$ | 85–20 |
| H-Asp-Tyr(SO$_3$H)-Lys-Gly-Trp-Lys-Asp-Phe-NH$_2$ | 45*–IA |
| Hpp(SO$_3$H)-Met-DAla-Trp-Met-Asp-Phe-NH$_2$ | 59–16 |
| Suc-Tyr(SO$_3$H)-Ahx-Gly-Trp-Ahx-Asp-Phe-NH$_2$ | 100–97 |
| H-βAsp-Tyr(SO$_3$H)-Met-Gly-Trp-Met-Asp-MePhe-NH$_2$ | 100–78 |

TABLE 2-continued

| STRUCTURE | % FEEDING INHIBITION 0.5 hr–3 hr |
|---|---|
| H-DAsp-Tyr($SO_3H$)-Met-Gly-Trp-Met-Asp-MePhe-$NH_2$ | 100–72 |
| For-Tyr($SO_3H$)-Met-Gly-Trp-Met-Asp-MePhe-$NH_2$ | 100–96 |
| iBuOCO-Tyr($SO_3H$)-Met-Gly-Trp-Met-Asp-MePhe-$NH_2$ | 100–99 |
| H-Asp-DTyr($SO_3H$)-Met-Gly-Trp-Met-Asp-MePhe-$NH_2$ | 85–35 |
| Hpp($SO_3H$)-Met-Gly-Trp-Met-Asp-MePhe-$NH_2$ | 100–100 |
| Hpp($SO_3H$)-Met-DAla-Trp-Met-Asp-MePhe-$NH_2$ | 69–27 |
| PrOCO-Tyr($SO_3H$)-Met-Gly-Trp-Met-Asp-Phe-$NH_2$ | 90–74 |
| EtOCO-Tyr($SO_3H$)-Met-Gly-Trp-Met-Asp-Phe-$NH_2$ | 89–63 |
| MeOCO-Tyr($SO_3H$)-Met-Gly-Trp-Met-Asp-Phe-$NH_2$ | 100–91 |
| H-βAsp-Tyr($SO_3H$)-Met-Gly-Trp-Met-Asp-Phe-$NH_2$ | 91–21 |
| H-Try($SO_3H$)-Met-Gly-Trp-Met-Asp-Phe-$NH_2$ | 50–30* |
| Suc-Tyr($SO_3H$)-Met-Gly-Trp-Met-Asp-Phe-$NH_2$ | 75–55 |
| Hpp($SO_3H$)-Met-Gly-Trp-Met-Asp-Phe-$NH_2$ | 99–75 |
| H-Asp-Tyr($SO_3H$)-Ahx-Gly-Trp-Met-Asp-Phe-$NH_2$ | NT–NT |
| H-Asp-Tyr($SO_3H$)-Met-Gly-DTrp-Met-Asp-Phe-$NH_2$ | 42*–IA |
| H-Asp-Tyr($SO_3H$)-Met-Gly-Trp-Ahx-Asp-Phe-$NH_2$ | 82–23 |
| H-Asp-Tyr($SO_3H$)-Met-Gly-Trp-Met-Asp-DPhe-$NH_2$ | 46–14* |
| H-Asp-Tyr($SO_3H$)-MetO-Gly-Trp-MetO-Asp-Phe-$NH_2$ | 15–IA |
| H-Asp-Tyr($SO_3H$)-Ahx-Gly-Trp-Ahx-Asp-Phe-$NH_2$ | 82–27 |
| H-Asp-Tyr($SO_3H$)-Leu-Gly-Trp-Leu-Asp-Phe-$NH_2$ | 89–24 |
| For-Tyr($SO_3H$)-Met-Gly-Trp-Met-Asp-Phe-$NH_2$ | 100–66 |
| H-Asp-Tyr($SO_3H$)-MetO-Gly-Trp-Met-Asp-Phe-$NH_2$ | 89–25 |
| H-Asp-Tyr($SO_3H$)-Met-DAla-Trp-Met-Asp-Phe-$NH_2$ | 16–18* |
| H-Asp-Tyr($SO_3H$)-Met-Gly-Trp-DMet-Asp-Phe-$NH_2$ | 30*–IA |
| H-Asp-Tyr($SO_3H$)-Met-Gly-Trp-MetO-Asp-Phe-$NH_2$ | 45–21* |
| H-Asp-Tyr($SO_3H$)-Met-Gly-Trp-Met-Asp-Phe(4-Me)-$NH_2$ | 57–18 |
| H-Asp-Tyr($SO_3H$)-Met-Gly-Trp-DMet-Asp-Tyr-$NH_2$ | 23*–IA |
| Hpp($SO_3H$)-Met-Gly-Trp-Pro-Asp-Phe-$NH_2$ | 48–IA |
| Hpp($SO_3H$)-Pro-Gly-Trp-Pro-Asp-Phe-$NH_2$ | 25–IA |
| Suc-Tyr($SO_3H$)-Ahx-Gly-Trp-Ahx-Asp-MePhe-$NH_2$ | 100–98 |
| iBuOCO-Tyr($SO_3H$)-Ahx-Gly-Trp-Ahx-Asp-MePhe-$NH_2$ | 100–100 |
| Hpp($SO_3H$)-Ahx-Gly-Trp-Ahx-Asp-MePhe-$NH_2$ | 94–96 |
| iBuOCO-Tyr($SO_3H$)-Ahx-Gly-Trp-Ahx-Asp-Phe-$NH_2$ | 100–100 |
| Hpp($SO_3H$)-Ahx-Gly-Trp-Ahx-Asp-Phe-$NH_2$ | 100–99 |
| Suc-Tyr($SO_3H$)-Met-DAla-Trp-Met-Asp-Phe-$NH_2$ | 75–30 |
| For-Tyr($SO_3H$)-Ile-Gly-Trp-Ile-Asp-Phe-$NH_2$ | NT–NT |
| Suc-Tyr($SO_3H$)-Ile-Gly-Trp-Ile-Asp-Phe-$NH_2$ | 73–54 |
| iBuOCO-Tyr($SO_3H$)-Ile-Gly-Trp-Ile-Asp-Phe-$NH_2$ | 62–58 |
| Hpp($SO_3H$)-Ile-Gly-Trp-Ile-Asp-Phe-$NH_2$ | 87–85 |
| Suc-Tyr($SO_3H$)-Met-Gly-Trp-Met-Asp-MePhe-$NH_2$ | 100–95 |
| H-DAsp-Tyr($SO_3H$)-Ile-Gly-Trp-Ile-Asp-MePhe-$NH_2$ | 95–70 |
| For-Tyr($SO_3H$)-Ile-Gly-Trp-Ile-Asp-MePhe-$NH_2$ | 100–85 |
| Suc-Tyr($SO_3H$)-Ile-Gly-Trp-Ile-Asp-MePhe-$NH_2$ | 100–100 |
| iBuOCO-Tyr($SO_3H$)-Ile-Gly-Trp-Ile-Asp-MePhe-$NH_2$ | 96–92 |
| H-Asp-DTyr($SO_3H$)-Ile-Gly-Trp-Ile-Asp-MePhe-$NH_2$ | 40–IA |
| Hpp($SO_3H$)-Ile-Gly-Trp-Ile-Asp-MePhe-$NH_2$ | 100–97 |
| H-DAsp-Tyr($SO_3H$)-Ile-Gly-Trp-Ile-Asp-Phe-$NH_2$ | NT–NT |
| H-Asp-Tyr($SO_3H$)-Met-Pro-Trp-Met-Asp-MePhe-$NH_2$ | 24*–10* |
| iBuOCO-Tyr($SO_3H$)-Met-DAla-Trp-Met-Asp-MePhe-$NH_2$ | NT–NT |
| H-βAsp-Tyr($SO_3H$)-Ile-Gly-Trp-Ile-Asp-MePhe-$NH_2$ | NT–NT |
| For-Tyr($SO_3H$)-Ile-Gly-Trp-Ahx-Asp-MePhe-$NH_2$ | NT–NT |
| Suc-Tyr($SO_3H$)-Ile-Gly-Trp-Ahx-Asp-MePhe-$NH_2$ | 100–100 |
| iBuOCO-Tyr($SO_3H$)-Ile-Gly-Trp-Ahx-Asp-MePhe-$NH_2$ | NT–NT |
| Hpp($SO_3H$)-Ile-Gly-Trp-Ahx-Asp-MePhe-$NH_2$ | 98–100 |

IA means "inactive".
* <10% inhibition at 30 μg/kg; number shown represents % inhibition at dose of 300 μg/kg.
NT means "not tested"

An appropriate procedure for administering a peptide designated here as suitable for intraperitoneal, intravenous, intramuscular, subcutaneous, or intranasal administration, to a mammal in need of either treatment for obesity or prevention of obesity, is at a dose of about 0.03 micrograms (μg) to 3 mg per kg of body weight per day, either as single dose or divided among two to four doses. The dosage may be varied, depending upon the requirements of the patient and the compound being employed.

The peptides of this invention have the ability to stimulate gallbladder contraction in mammals. Thus, they also find utility as diagnostic aids in X-ray examination of the gallbladder. The use of gallbladder contracting agents as diagnostic aids is a well established medical procedure.

EXAMPLES

The invention may be further illustrated by the following examples. Examples 1–18 illustrate the synthesis of intermediates. Examples 19–100 illustrate the synthesis of compounds that have been designated above as either a compound of the invention or a compound useful in the treatment and prevention of obesity. The examples are intended to illustrate the invention, not to limit it in any manner.

Peptide syntheses, unless otherwise stated, were initiated with 1 milliequivalent of aminomethyl resin, where the resin was 99:1 by weight styrene:divinylbenzene copolymer. Reactions were performed at room temperature unless otherwise stated. Washing steps were performed three times with 50 ml of the specified solvent unless otherwise stated.

EXAMPLE 1

Isobutyl Succinimidyl Carbonate (iBuOCO-OSu)

To a solution of isobutyl chloroformate (26 ml, 200 mmole) in 600 ml of chloroform was added in portions the dicyclohexylamine (DCHA) salt of N-hydroxysuccinimide (HOSu, 49.28 g, 200 mmole). After stirring the resulting suspension overnight, the precipitated DCHA hydrochloride was filtered off and washed with chloroform. The concentrated filtrate (ca. 50 ml) and washings were diluted with 400 ml of ethyl acetate (EtOAc) and washed with 10% citric acid (4×100 ml), brine (2×100 ml), 10% sodium bicarbonate (3×100 ml), and brine (4×100 ml) and then dried (magnesium sulfate), filtered, and concentrated to ca. 100 ml. On diluting with ether and precipitating with hexane, 26.6 g (62% yield) of iBuOCO-OSu was obtained, mp 33°–35° C.

EXAMPLE 2

Fmoc-DTyr-OH

D-Tyrosine (1.81 g) was dissolved in 20 ml of water and 30 ml of tetrahydrofuran (THF) with 10 ml of sodium hydroxide. Solid 9-fluroenylmethyl succinimidyl carbonate (Fmoc-OSu, 3.37 g) was added with rapid stirring. The suspension was adjusted to pH 7 with N sodium hydroxide and stirred overnight. Solid citric acid (3 g) was added followed by 60 ml of EtOAc. The EtOAc layer was collected, washed with 10% citric acid, brine, and dried (magnesium sulfate). Evaporation of the EtOAc solution gave a light tan syrup which was crystallized from dichloromethane (DCM) to give 3.9 g of Fmoc-DTyr-OH, mp 178°–181° C.

EXAMPLE 3

Fmoc-Tyr-OH

Following the procedure of Example 2 but substituting L-tyrosine (9.06 g) for D-tyrosine, 18.4 g of Fmoc-Tyr-OH was obtained, mp 172°–177° C.

EXAMPLE 4

Fmoc-MeTyr-OH

Following the procedure of Example 2 but substituting N-methyltyrosine (1.95 g) for D-tyrosine, 1.22 g of Fmoc-MeTyr-OH was obtained, mp 152°–158° C.

EXAMPLE 5

Boc-MePhe-(4-oxymethylphenyl)acetic Acid

To a solution of Boc-MePhe-OH (27.93 g) and 4-(bromomethyl) phenylacetic acid phenacyl ester (33.32 g) in 1000 ml of acetonitrile was added potassium fluoride dihydrate (18.28 g). The suspension was stirred overnight, filtered and the filtrate evaporated to dryness. The residue, Boc-MePhe-(4-oxymethylphenyl)acetic acid phenacyl ester, was dissolved in 85% acetic acid (1200 ml), treated with zinc dust (128 g), and stirred for 2-hrs. Concentration of the filtered reaction mixture to ca. 400 ml and dilution with ca. 3200 ml of water gave an oil which was dissolved in EtOAc and treated with DCHA to give 41.31 g of the DCHA salt of title compound, mp 120°–122° C.

EXAMPLE 6

Boc-EtPhe-(4-oxymethylphenyl)acetic Acid

Following the procedure of Example 5 but substituting Boc-EtPhe-OH (7.33 g) for Boc-MePhe-OH, 5.69 g of the DCHA salt of Boc-EtPhe-(4-oxymethylphenyl)acetic acid was obtained, mp 137°–141° C.

EXAMPLE 7

Boc-Phe(4-Cl)-(4-oxymethylphenyl)acetic Acid

Following the procedure of Example 5 but substituting Boc-Phe(4-Cl)-OH (2.5 g) for Boc-MePhe-OH, 3.44 g of the free base of Boc-Phe(4-Cl)-(4-oxymethylphenyl)acetic acid was obtained.

EXAMPLE 8

Boc-Tyr(Me)-(4-oxymethylphenyl)acetic Acid

Following the procedure of Example 5 but substituting Boc-Tyr(Me)-OH (2.5 g) for Boc-MePhe-OH, 1.83 g of the free base of Boc-Tyr(Me)-(4-oxymethylphenyl)acetic acid was obtained, mp 64°–67° C.

EXAMPLE 9

Fmoc-Tyr(tBu)-(4-oxymethylphenyl)acetic Acid

Following the procedure of Example 5 but substituting Fmoc-Tyr(tBu)-OH (6.86 g) for Boc-MePhe-OH, 4.88 g of the free base of Fmoc-Tyr(tBu)-(4-oxymethylphenyl)acetic acid was obtained, mp 192°–195° C.

EXAMPLE 10

Fmoc-Met-Asp(OtBu)-OH

Fmoc-Met-OSu was prepared, in situ, by the reaction of Fmoc-Met-OH (14.87 g) HOSu (5.52 g), and dicyclohexylcarbodiimide (DCC, 8.26 g) in THF (200 ml) at 0° C. for 3.5 hrs. Precipitated dicyclohexylurea (DCU) was removed by filtration and the THF filtrate was added to a cold solution of H-Asp (OtBu)-OH in 220 ml of 10:1 water/THF to which had been added 40 ml of N sodium hydroxide. After stirring the reaction mixture at room temperature overnight, solid citric acid (20 g) was added along with EtOAc (600 ml). The EtOAc layer was separated, washed with 10% citric acid and brine, and dried (magnesium sulfate). Evaporation of the EtOAc solution gave a residue which was dissolved in 200 ml of EtOAc and treated with DCHA (7.84 ml) to precipitate 17.93 g of the DCHA salt of the desired product, mp 159°–162° C.

EXAMPLE 11

H-Phe-OCH$_2$-Pam-resin

Boc-Phe-(4-oxymethylphenyl)acetic acid (0.83 g, 2 mmole), 1-hydroxybenzotriazole (HOBt, 0.46 g, 3 mmole) and DCC (0.41 g, 2 mmole) were dissolved in 50 ml of 4:1 DCM/DMF and stirred at 0° C. for 1 hr. Aminomethyl-resin (1.34 g, 1 mmole available nitrogen (was suspended in the filtered reaction mixture (precipitated DCU removed) and shaken for 2 to 15 hours. The product, Boc-Phe-OCH*-Pam-resin, was isolated by filtration and treated according to Table 1 (Steps 10–14) to give the desired free base, H-Phe-OCH$_2$-Pam-resin.

EXAMPLE 12

M-MePhe-OCH$_2$-Pam-resin

Boc-MePhe-(4-oxymethylphenyl)acetic acid (from 1.82 g, 3 mmole, of its DCHA salt, Example 5) and HOBt (0.69 g, 4.5 mmole) in 40 ml of 1:3 DMF/DCM followed by DCC (0.62 g, 3 mmole) in 20 ml of DCM were added to aminomethyl-resin (1.34 g, 1 mmole available nitrogen) to give a suspension which was shaken for 2 to 15 hours. The desired product, Boc-MePhe-OCH$_2$-Pam-resin, was isolated by filtration, washed with 2-propanol and DCM, and treated according to Table 1 (Steps 10–14) to give the desired free base, H-MePhe-OCH$_2$-Pam-resin.

EXAMPLE 13

H-EtPhe-OCH$_2$-Pam-resin

Following the procedure of Example 12 but substituting Boc-EtPhe-(4-oxymethylpheny)acetic acid (from 1.87 g, 3 mmole, of its DCHA salt, Example 6) for Boc-MePhe-(4-oxymethylphenyl)acetic acid, H-EtPhe-OCH$_2$-Pam-resin was obtained.

EXAMPLE 14

H-Phe(4-Cl)-OCH$_2$-Pam-resin

Following the procedure of Example 11 but substituting Boc-Phe(4-Cl)-(4-oxymethylphenyl)acetic acid (0.90 g, 2 mmole, Example 7) for Boc-Phe-(4-oxymethylphenyl)acetic acid, H-Phe(4-Cl)-OCH$_2$-Pam-resin was obtained.

EXAMPLE 15

H-Phe(4-NO$_2$)-OCH$_2$-Pam-resin

Boc-Phe(4-NO$_2$)-OH (1.39 g) was dissolved in 100 ml of 70% methanol (MeOH) and adjusted to pH 7 with the addition of N cesium bicarbonate. The solution was evaporated to dryness with the residue being evaporated three more times with added DMF. The resultant dried cesium salt of Boc-Phe(4-NO$_2$)-OH was dissolved in 60 ml of DMF and shaken with BrCH$_2$-Pam-resin (1 meq of Br) overnight. The desired product, Boc-Phe(4-NO$_2$)-OCH$_2$-Pam-resin, was isolated by filtration, washed with DCM, and treated according to Table 1 (Steps 10–14) to give the desired free base, H-Phe(4-NO$_2$)-OCH$_2$-Pam-resin.

EXAMPLE 16

H-Tyr(Me)-OCH$_2$-Pam-resin

Following the procedures of Example 11 but substituting Boc-Tyr(Me)-(4-oxymethylphenyl)acetic acid (0.87 g, 2 mmole, Example 8) for Boc-Phe-(4-oxymethylphenyl)acetic acid H-Tyr(Me)-OCH$_2$-Pam-resin was obtained.

EXAMPLE 17

H-Tyr(tBu)-OCH$_2$-Pam-resin

Fmoc-Tyr(tBu)-(4-oxymethylphenyl)acetic acid (1.82 g, 3 mmole, Example 9), 1-hydroxybenzotriazole (HOBt, 0.69 g, 4.5 mmole), and DCC (0.62 g, 3 mmole) were dissolved in 50 ml of 4:1 DCM/DMF and stirred at 0° C for 1 hr. Aminomethlyresin (1.34 g, 1 mmole available nitrogen) was suspended in the filtered reaction mixture (precipitated DCU removed) and shaken for 2 to 15 hours. The product, Fmoc-Tyr(tBu)-OCH$_2$-Pam-resin, was isolated by filtration and treated according to Table 1 (Steps 16–20) to give the desired free base, H-Tyr(tBu)-OCH$_2$-Pam-resin.

EXAMPLE 18

H-MeTyr(Me)-OCH$_2$-Pam-resin

Following the procedure of Example 15 but substituting Boc-MeTyr(Me)-OH (from 1.47 g of its DCHA salt) for Boc-Phe(Ho$_2$)-OH, MeTyr(Me)OCH$_2$-Pam-resin was obtained

EXAMPLE 19

H-DAsp-Tyr(SO$_3$H)-Met-Gly-Trp-Met-Asp-Phe-NH$_2$

H-Phe-OCH$_2$-Pam-resin (Example 11) was sequentially coupled with Fmoc-Asp(OtBu)-OH, Fmoc-Met-OH, Fmoc-Trp-OH, Fmoc-Gly-OH, Fmoc-Met-OH, Fmoc-Tyr-OH (Example 3), and Fmoc-DAsp(To-Bu)-OH according to Table 1 (coupling Steps 3–4 followed by Fmoc removal Steps 16–20) to provide Fmoc-DAsp-(OtBu)-Tyr-Met-Gly-Trp-Met-Asp-(OtBu)-Phe-OCH$_2$-Pam-resin which was sulfated, deprotected, and cleaved from the resin according to Table 1 (Steps 21–25, Steps 10–20, and then Steps 26–29 with ammonia) to give the title compound which was chromatographically purified on Trisacryl M DEAE according to Table 1 (Step 30) to give 198 mg of the ammonium salt of the title compound. Amino acid analysis following acid decomposition gave Asp 2.11 (2), Tyr 1.04 (1), Met 2.07 (2), Gly 1.08 (1), and Phe 1.04 (1). Infrared absorption spectrum showed a strong peak typical of a sulfuric acid ester at 1050 cm$^{-1}$. TLC R$_f$ 0.35 (TLC herein refers to chromatography of the title compound of Merck silica gel thin layer plates in the solvent system chloroform-methanol-acetic acid-water, 6:3:1:1.

EXAMPLE 20 iBuOCO-Tyr(SO$_3$H)-Met-Gly-Trp-Met-Asp-Phe-NH$_2$

H-Phe-OCH$_2$-Pam-resin (Example 11) was sequentially coupled with Fmoc-Asp(OtBu)-OH, Fmoc-Met-OH, Fmoc-Trp-OH, Fmoc-Gly-OH, Fmoc-Met-OH, and Fmoc-Tyr(tBu)-OH according to Table 1 (coupling Steps 5–7 followed by Fmoc removal Steps 16–20) to give H-Tyr(tBu)-Met-Gly-Trp-Met-Asp(OtBu)-Phe-OCH$_2$-Pam-resin which was coupled with iBuOCO-OSu (Example 1) according to Table 1 (Steps 8–9) to give iBuOCO-Tyr(tBu)-Met-Gly-Trp-Met-Asp(OtBu)-Phe-OCH$_2$-Pam-resin which was deprotected, sulfated, and cleaved from the resin according to Table 1 (Steps 10–15, Steps 21–25, and then Steps 26–29 with ammonia) to give the title compound which was chromatographically purified on Amberlite XAD-2, Trisacryl M DEAE, and P-40 ODS-3, sequentially, according to Table 1 (Step 30) to give 206 mg of the ammonium salt of the title compound. Amino acid analysis following acid decomposition gave Asp 1.06 (1), Tyr 1.04 (1), Met 2.04 (2), Gly 1.06 (1), and Phe 1.04 (1). Infrared absorption spectrum showed a strong peak typical of a sulfuric acid ester at 1050 cm$^{-1}$. TLC R$_f$ 0.56.

EXAMPLE 21

H-Asp-DTyr(SO$_3$H)-Met-Gly-Trp-Met-Asp-Phe-NH$_2$

H-Phe-OCH$_2$-Pam-resin (Example 11) was sequentially coupled with Fmoc-Asp(OtBu)-OH, Fmoc-Met-OH, Fmoc-Trp-OH, Fmoc-Gly-OH, Fmoc-Met-OH, Fmoc-DTyr-OH (Example 2), and Boc-Asp-(OtBu)-OH according to Table 1 (coupling Steps 3–4 followed by Fmoc removal Steps 16–20) to give Boc-Asp(OtBu)-DTyr-Met-Gly-Trp-Met-Asp(OtBu)-Phe-OCH$_2$-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE according to Table 1 (Step 30) to give 241 mg of the ammonium salt of the title compound. Amino acid analysis following acid decomposition gave Asp 2.14 (2), Tyr 1.06 (1), Met 2.12 (2), Gly 0.95 (1), Phe 0.98 (1), and $NH_3$ 1.30 (2). Infra-red absorption spectrum showed a strong peak typical of a sulfuric acid ester at 1050 cm$^{-1}$. TLC $R_f$ 0.32.

EXAMPLE 22

H-Asp-Tyr(SO₃H)-DMet-Gly-Trp-Met-Asp-Phe-NH₃

H-Phe-OCH₂-Pam-resin (Example 11) was sequentially coupled with Fmoc-Asp(OtBu)-OH, Fmoc-Met-OH, Fmoc-Trp-OH, Fmoc-Gly-OH, Fmoc-DMet-OH, Fmoc-Tyr-OH (Example 3), and Boc-Asp(Ot-Bu)-OH according to Table 1 (coupling Steps 3–4 followed by Fmoc removal Steps 16–20) to provide Boc-Asp(Ot-Bu)-Tyr-DMet-Gly-Trp-Met-Asp(OtBu)-Phe-OCH₂-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE according to Table 1 (Step 30) to give 219 mg of the ammonium salt of the title compound. Amino acid analysis following acid decomposition gave Asp 2.07 (2), Tyr 1.02 (1), Met 2.11 (2), Gly 0.95 (1), Phe 1.11 (1), and $NH_3$ 1.31 (2). Infrared absorption spectrum showed a strong peak typical of a sulfuric acid ester at 1050 cm$^{-1}$. TLC $R_f$ 0.37.

EXAMPLE 23

H-Asp-Tyr(SO₃H)-DAhx-Gly-Trp-Met-Asp-Phe-NH₂

H-Phe-OCH₂-Pam-resin (Example 11) was sequentially coupled with Fmoc-Asp(OtBu)-OH, Fmoc-Met-OH, Fmoc-Trp-OH, Fmoc-GlyOH, Fmoc-DAhx-OH, Fmoc-Tyr-OH (Example 3), and Boc-Asp-(OtBu)-OH according to Table 1 (coupling Steps 3–4 followed by Fmoc removal Steps 16–20) to provide Boc-Asp(Ot-Bu)-Tyr-DAhx-Gly-Trp-Met-Asp(OtBu)-Phe-OCH₂-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE according to Table 1 (Step 30) to give 248 mg of the ammonium salt of the title compound. Amino acid analysis following acid decomposition gave Asp 2.11 (2), Tyr 1.03 (1), Ahx 0.97 (1), Gly 0.99 (1), Met 1.07 (1), and Phe 1.07 (1). Infra-red absorption spectrum showed a strong peak typical of a sulfuric acid ester at 1050 cm$^{-1}$. TLC $R_f$ 0.34.

EXAMPLE 24

H-Asp-Tyr(SO₃H)-Met-Sar-Trp-Met-Asp-Phe-NH₂

H-Phe-OCH₂-Pam-resin (Example 11) was sequentially coupled with Fmoc-Asp(OtBu)-OH, Fmoc-Met-OH, Fmoc-Trp-OH, Fmoc-Sar-OH, Fmoc-Met-OH, Fmoc-Tyr-OH (Example 3), and Boc-Asp(To-Bu)-OH according to Table 1 (coupling Steps 3–4 followed by Fmoc removal Steps 16–20) to provide Boc-Asp(Ot-Bu)-Tyr-Met-Sar-Trp-Met-Asp(OtBu)-Phe-OCH₂-Pam-resin which was sulfated, deprotected and cleaved from the resin according to Table 1 (Steps 21–25, Steps 10–15, and then Steps 26–29 with ammonia) to give the title compound which was chromatographically purified on Trisacryl M DEAE according to Table 1 (Step 30) to give 240 mg of the ammonium salt of the title compound. Amino acid analysis following acid decomposition gave Asp 1.93 (2), Tyr 0.97 (1), Met 2.00 (2), Sar 1.03 (1), Phe 1.02 (1), and $NH_3$ 1.54 (2). Infrared absorption spectrum showed a strong peak typical of a sulfuric acid ester at 1050 cm$^{-1}$. TLC $R_f$ 0.32.

EXAMPLE 25

H-Asp-Tyr(SO₃H)-Met-Gly-MeTrp-Met-Asp-Phe-NH₂

H-Phe-OCH₂-Pam-resin (Example 11) was sequentially coupled with Fmoc-Asp(OtBu)-OH, Fmoc-Met-OH, Fmoc-MeTrp-OH, Fmoc-Gly-OH, Fmoc-Met-OH, Fmoc-Tyr(tBu)-OH, and Fmoc-Asp(OtBu)-OH according to Table 1 (coupling Steps 3–4 followed by Fmoc removal Steps 16–20) to provide Fmoc-Asp(Ot-Bu)-Tyr-(tBu)-Met-Gly-MeTrp-Met-Asp(OtBu)-Phe-OCH₂-Pam-resin which was deprotected, sulfated, deprotected, and cleaved from the resin according to Table 1 (Steps 10–15, Steps 21–25, Steps 16–20, and then Steps 26–29 with ammonia) to give the title compound which was chromatographically purified on Trisacryl M DEAE according to Table 1 (Step 30) to give 310 mg of the ammonium salt of the title compound. Amino acid analysis following acid decomposition gave Asp 2.03 (2), Tyr 1.02 (1), Met 1.95 (2), Gly 0.93 (1), and Phe 1.01 (1). Infrared absorption spectrum showed a strong peak typical of a sulfuric acid ester at 1050 cm$^{-1}$. TLC $R_f$ 0.35.

EXAMPLE 26

H-Asp-Tyr(SO₃)-Met-Gly-Nal-Met-Asp-Phe-NH₂

H-Phe-OCH₂-Pam-resin (Example 11) was sequentially coupled with Fmoc-Asp(OtBu)-OH, Fmoc-Met-OH, Fmoc-Nal-OH Fmoc-Gly-OH, Fmoc-Met-OH, Fmoc-Tyr-OH (Example 3), and Boc-Asp-(OtBu)-OH according to Table 1 (coupling Steps 3–4 followed Fmoc removal Steps 16–20 ) to provide Boc-Asp(Ot-Bu)-Tyr-Met-Gly-Nal-Met-Asp(OtBu)-Phe-OCH₂-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE according to Table 1 (Step 30) to give 260 mg of the ammonium salt of the title compound. Amino acid analysis following acid decomposition gave Asp 1.97 (2), Tyr 0.91 (1), Met 2.13 (2), Gly 1.09 (1), Nal 0.76 (1), and Phe 1.14 (1). Infrared absorption spectrum showed a strong peak typical of a sulfuric acid ester at 1050 cm$^{-1}$. TLC $R_f$ 0.38.

EXAMPLE 27

H-Asp-Tyr(SO₃H)-Met-Gly-Trp-Met-DAsp-Phe-NH₂

H-Phe-OCH₂-Pam-resin (Example 11) was sequentially coupled with Fmoc-DAsp(OtBu)-OH, Fmoc-Met-OH, Fmoc-Trp-OH, Fmoc-Gly-OH, Fmoc-Met-OH, Fmoc-Tyr-OH (Example 3), and Boc-Asp(OtBu)-OH according to Table 1 (coupling Steps 3–4 followed by Fmoc removal Steps 16–20) to provide Boc-Asp(Ot-Bu)-Tyr-Met-Gly-Trp-Met-DAsp(OtBu)-Phe-OCH₂-Pam-resin which was sulfated, deprotected, and cleaved from the resin according to Table 1 (Steps 21–25 Steps 10–15, and then Steps 26–29 with ammonia) to give the title compound which was chromatographically purified on Trisacryl M DEAE according to Table 1 (Step 30) to give 121 mg of the ammonium salt of the title compound. Amino acid analysis following acid decomposition gave Asp 2.03 (2), Tyr 0.98 (1), Met 2.05 (2), Gly 1.07 (1), and Phe 1.08 (1). Infrared absorption spectrum showed a strong peak typical of a sulfuric acid ester at 1050 cm$^{-1}$. TLC R$_f$ 0.43.

EXAMPLE 28

H-Asp-Tyr(SO$_3$H)-Met-Gly-Trp-Met-Asn-Phe-NH$_2$

H-Phe-OCH$_2$-Pam-resin (Example 11) was sequentially coupled with Fmoc-Asn-OH, Fmoc-Met-OH, Fmoc-Trp-OH, Fmoc-Gly-OH, Fmoc-Met-OH, Fmoc-Tyr(tBu)-OH, and Fmoc-Asp(OtBu)-OH according to Table 1 (coupling Steps 3–4 followed by Fmoc removal Steps 16–20 ) to provide Fmoc-Asp(OtBu)-Tyr(tBu)-Met-Gly-Trp-Met-Asn-Phe-OCH$_2$-Pam-resin which was deprotected, sulfated, deprotected, and cleaved from the resin according to Table 1 (Steps 10–15, Steps 21–25, Steps 16–20, and then Steps 26–29 with ammonia) to give the title compound which was chromatographically purified on Trisacryl M DEAE and P-40 ODS-3, sequentially, according to Table 1 (Step 30) to give 30 mg of the ammonium salt of the title compound. Amino acid analysis following acid decomposition gave Asp 2.02 (2), Tyr 1.03 (1), Met 1.93 (2), Gly 1.01 (1), and Phe 1.01 (1). Infrared absorption spectrum showed a strong peak typical of a sulfuric acid ester at 1050 cm$^{-1}$. TLC R$_f$ 0.43.

EXAMPLE 29

H-Asp-Tyr(SO$_3$H)-Met-Gly-Trp-Met-Asp-MePhe-NH$_2$

H-MePhe-OCH$_2$-Pam-resin (Example 12) was sequentially coupled with Fmoc-Met-Asp(OtBu)-OH (free base of Example 10), Fmoc-Trp-OH, Fmoc-Gly-OH, Fmoc-Met-OH, Fmoc-Tyr(tBu)-OH, and Fmoc-Asp(OtBu)-OH according to Table 1 (coupling Steps 3–4 followed by Fmoc removal Steps 16–20) to provide Fmoc-Asp(OtBu)-Tyr(tBu)-Met-Gly-Trp-Met-Asp(OtBu)-MePhe-OCH$_2$-Pam-resin which was deprotected, sulfated, deprotected, and cleaved from the resin according to Table 1 (Steps 10–15, Steps 21–25, Steps 16–20, and then Steps 26–29 with ammonia) to give the title compound which was chromatographically purified on Trisacryl M DEAE and P-40 ODS-3, sequentially, according to Table 1 (Step 30) to give 243 mg of the ammonium salt of the title compound. Amino acid analysis following acid decomposition gave Asp 2.14 (2), Tyr 1.02 (1), Met 2.04 (2), Gly 1.07 (1), and NH$_3$ 1.87 (2). Infrared absorption spectrum showed a strong peak typical of a sulfuric acid ester at 1050 cm$^{-1}$. TLC R$_f$ 0.37.

EXAMPLE 30

H-Asp-Tyr(SO$_3$H)-Met-Gly-Trp-Met-Asp-MeTyr(-Me)-NH$_2$

H-MeTyr(Me)-OCH$_2$-Pam-resin (Example 18) was sequentially coupled with Fmoc-Met-Asp(OtBu)-OH (free base of Example 10), Fmoc-Trp-OH, Fmoc-Gly-OH, Fmoc-Met-OH, Fmoc-Tyr(tBu)-OH, and Fmoc-Asp(OtBu)-OH according to Table 1 (coupling Steps 5–7 followed by Fmoc removal Steps 16–20) to provide Fmoc-Asp(OtBu)-Tyr(tBu)-Met-Gly-Trp-Met-Asp(OtBu)-MeTyr-(Me)-OCH$_2$-Pam-resin which was deprotected, sulfated, deprotected, and cleaved from the resin according to Table 1 (Steps 10–15, Steps 21–25, Steps 16–20, and then Steps 26–29 with ammonia) to give the title compound which was chromatographically purified on Trisacryl M DEAE and P-40 ODS-3, sequentially, according to Table 1 (Step 30) to give 100 mg of the ammonium salt of the title compound. Amino acid analysis following acid decomposition gave Asp 2.06 (2), Tyr 1.06 (1), Met 1.98 (2), and Gly 1.05 (1). Infrared absorption spectrum showed a strong peak typical of a sulfuric acid ester at 1050 cm$^{-1}$. TLC R$_f$ 0.45.

EXAMPLE 31

H-Asp-Tyr(SO$_3$H)-Met-Gly-Trp-Met-Asp-Phe(4-NO$_2$)-NH$_2$

H-Phe(4-NO$_2$)-OCH$_2$-Pam-resin (Example 15) was sequentially coupled with Fmoc-Asp(OtBu)-OH, Fmoc-Met-OH, Fmoc-Trp-OH, Fmoc-Gly-OH, Fmoc-Met-OH, Fmoc-Tyr(tBu)-OH, and Fmoc-Asp(OtBu)-OH according to Table 1 (coupling Steps 3–4 followed by Fmoc removal Steps 16–20) to provide Fmoc-Asp(OtBu)-Tyr(tBu)-Met-Gly-Trp-Met-Asp(OtBu)-Phe-(4-NO$_2$)-OCH$_2$-Pam-resin which was deprotected, sulfated, deprotected, and cleaved from the resin according to Table 1 (Steps 10–15, Steps 21–25, Steps 16–20 and then Steps 26–29 with ammonia) to give the title compound which was chromatographically purified on Trisacryl M DEAE and P-40 ODS-3, sequentially, according to Table 1 (Step 30) to give 128 mg of the ammonium salt of the title compound. Amino acid analysis following acid decomposition gave Asp 1.98 (2), Tyr 1.05 (1), Met 1.92 (2), and Gly 1.05 (1). Infrared absorption spectrum showed a strong peak typical of a sulfuric acid ester at 1050 cm$^{-1}$. TLC R$_f$ 0.37.

EXAMPLE 32

H-As-Tyr(SO$_3$H)-Met-Gly-Trp-Met-Asp-Phe(4-Cl)-NH$_2$

H-Phe(4-Cl)-OCH$_2$-Pam-resin (Example 14) was sequentially coupled with Fmoc-Asp(OtBu)-OH, Fmoc-Met-OH, Fmoc-Trp-OH, Fmoc-Gly-OH, Fmoc-Met-OH, Fmoc-Tyr(tBu)-OH, and Fmoc-Asp(OtBu)-OH according to Table 1 (coupling Steps 3–4 followed by Fmoc removal Steps 16–20) to provide Fmoc-Asp(OtBu)-Tyr(tBu)-Met-Gly-Trp-Met-Asp(OtBu)-Phe-(4-Cl)-OCH$_2$-Pam-resin which was deprotected, sulfated, deprotected, and cleaved from the resin according to Table 1 (Steps 10–15, Steps 21–25, Steps 16–20, and then Steps 26–29 with ammonia) to give the title compound which was chromatographically purified on Trisacryl M DEAE and P-40 ODS-3, sequentially, according to Table 1 (Step 30) to give 299 mg of the ammonium salt of the title compound. Amino acid analysis following acid decomposition gave Asp 1.85 (2), Tyr 1.02 (1), Met 1.78 (2), and Gly 0.92 (1). Infrared absorption spectrum showed a strong peak typical of a sulfuric acid ester at 1050 cm$^{-1}$. TLC R$_f$ 0.36.

EXAMPLE 33

H-Asp-Tyr(SO$_3$H)-Met-Gly-Trp-Met-Asp-Phe(4-NH$_2$)-NH$_2$

H-Asp-Tyr-(SO$_3$H)-Met-Gly-Trp-Met-Asp-Phe(4-NO$_2$)-NH$_2$ (64 mg, Example 31) was dissolved in 85% acetic acid (20 ml) and treated with zinc dust (69 mg) with stirring. After 30 min, the filtered reaction mixture was evaporated to dryness and the residue was chromatographically purified on P-40 ODS-3 according to Table 1 (Step 30) to give 30 mg of the ammonium salt of the title compound. Amino acid analysis following acid decomposition gave Asp 1.92 (2), Tyr 0.98 (1), Met 1.87 (2), and Gly 1.00 (1). Infrared absorption spectrum showed a strong peak typical of a sulfuric acid ester at 1050 cm$^{-1}$. TLC R$_f$ 0.35.

EXAMPLE 34

H-Asp-Tyr(SO$_3$H)-Met-Gly-Trp-Met-Asp-Tyr(Me)-NH$_2$

H-Tyr(Me)-OCH$_2$-Pam-resin (Example 16) was sequentially coupled with Fmoc-Asp(OtBu)-OH, Fmoc-Met-OH, Fmoc-Trp-OH, Fmoc-Gly-OH, Fmoc-Met-OH, Fmoc-Tyr(tBu)-OH, and Fmoc-Asp(OtBu)-OH according to Table 1 (coupling Steps 3–4 followed by Fmoc removal Steps 16–20) to provide Fmoc-Asp(OtBu)-Tyr(tBu)-Met-Gly-Trp-Met-Asp(OtBu)-Tyr(Me)-OCH$_2$-Pam-resin which was deprotected, sulfated, deprotected, and cleaved from the resin according to Table 1 (Steps 10–15, Steps 21–25, Steps 16–20, and then Steps 26–29 with ammonia) to give the title compound which was chromatographically purified on Trisacryl M DEAE and P-40 ODS-3, sequentially, according to Table 1 (Step 30) to give 313 mg of the ammonium salt of the title compound. Amino acid analysis following acid decomposition gave Asp 2.05 (2), Tyr 1.98 (1), Met 1.88 (2), and Gly 1.09 (1). Infrared absorption spectrum showed a strong peak typical of a sulfuric acid ester at 1050 cm$^{-1}$. TLC R$_f$ 0.38.

EXAMPLE 35

H-Asp-Tyr(SO$_3$H)-Met-Gly-Trp-Met-Asp-Phe-NHMe

H-Phe-OCH$_2$-Pam-resin (Example 11) was sequentially coupled with Fmoc-Asp(OtBu)-OH, Fmoc-Met-OH, Fmoc-Trp-OH, Fmoc-Gly-OH, Fmoc-Met-OH, Fmoc-Tyr(tBu)-OH, and Fmoc-Asp(OtBu)-OH according to Table 1 (coupling Steps 3–4 followed by Fmoc removal Steps 16–20) to provide Fmoc-Asp(OtBu)-Tyr(tBu)-Met-Gly-Trp-Met-Asp(OtBu)-Phe-OCH$_2$-Pam-resin which was deprotected, sulfated, deprotected, and cleaved from the resin according to Table 1 (Steps 10–15, Steps 21–25, Steps 16–20, and then Steps 26–29 with methylamine) to give the title compound which was chromatographically purified on Trisacryl M DEAE and P-40 ODS-3, sequentially, according to Table 1 (Step 30) to give 196 mg of the ammonium salt of the title compound. Amino acid analysis following acid decomposition gave Asp 1.99 (2), Tyr 1.00 (1), Met 1.98 (2), Gly 1.00 (1), and Phe 1.01 (1). Infrared absorption spectrum showed a strong peak typical of a sulfuric acid ester at 1050 cm$^{-1}$. TLC R$_f$ 0.47.

EXAMPLE 36

H-Asp-Tyr(SO$_3$H)-Met-Gly-Trp-Met-Asp-Phe-NHEt

H-Phe-OCH$_2$Pam-resin (Example 11) was sequentially coupled with Fmoc-Asp(OtBu)-OH, Fmoc-Met-OH, Fmoc-Trp-OH, Fmoc-GlyOH, Fmoc-Met-OH, Fmoc-Tyr-OH (Example 3), and Boc-Asp-(OtBu)-OH according to Table 1 (coupling Steps 3–4 followed by Fmoc removal Steps 16–20) to provide Boc-Asp(OtBu)-Tyr-Met-Gly-Trp-Met-Asp(OtBu)-Phe-OCH$_2$-Pam-resin which was sulfated, deprotected, and cleaved from the resin according to Table 1 (Steps 21–25, Steps 10–15, and then Steps 26–29 with ethylamine) to give the title compound which was chromatographically purified on Trisacryl M DEAE and P-40 ODS-3, sequentially, according to Table 1 (Step 30) to give 180 mg of the ammonium salt of the title compound. Amino acid analysis following acid decomposition gave Asp 1.99 (2), Tyr 0.84 (1), Met 2.03 (2), Gly 1.01 (1), Phe 0.97 (1), and NH$_3$ 1.14 (1). Infrared absorption spectrum showed a strong peak typical of a sulfuric acid ester at 1050 cm$^{-1}$. TLC R$_f$ 0.49.

EXAMPLE 37

H-Asp-Tyr(SO$_3$)-Met-Gly-Trp-Met-Asp-Phe-N(Me)$_2$

H-Phe-OCH$_2$-Pam-resin (Example 11) is sequentially coupled with Fmoc-Asp(OtBu)-OH, Fmoc-Met-OH, Fmoc-Trp-OH, Fmoc-Gly-OH, Fmoc-Met-OH, Fmoc-Tyr(tBu)-OH, and Fmoc-Asp(OtBu)-OH according to Table 1 (coupling Steps 3–4 followed by Fmoc removal Steps 16–20) to provide Fmoc-Asp(OtBu)-Tyr(tBu)-Met-Gly-Trp-Met-Asp(OtBu)-Phe-OCH$_2$-Pam-resin which is deprotected, sulfated, deprotected, and cleaved from the resin according to Table 1 (Steps 10–15, Steps 21–25, Steps 16–20, and then Steps 26–29 with dimethylamine) to give the title compound which is chromatographically purified on Trisacryl M DEAE and P-40 ODS-3, sequentially, according to Table 1 (Step 30) to give the ammonium salt of the title compound.

EXAMPLE 38

H-Asp-Tyr(SO$_3$H)-Met-Gly-Trp-Met-Asp-Phe-N(Et)$_2$

H-Phe-OCH$_2$-Pam-resin (Example 11) is sequentially coupled with Fmoc-Asp(OtBu)-OH, Fmoc-Met-OH, Fmoc-Trp-OH, Fmoc-Gly-OH, Fmoc-Met-OH, Fmoc-Tyr(tBu)-OH, and Fmoc-Asp(OtBu)-OH according to Table 1 (coupling Steps 3–4 followed by Fmoc removal Steps 16–20) to provide Fmoc-Asp(OtBu)-Tyr(tBu)-Met-Gly-Trp-Met-Asp(OtBu)-Phe-OCH$_2$-Pam-resin which is deprotected, sulfated, deprotected, and cleaved from the resin according to Table 1 (Steps 10–15, Steps 21–25, Steps 16–20, and then Steps 26–29 with diethylamine) to give the title compound which is chromatographically purified on Trisacryl M DEAE and P-40 ODS-3, sequentially, according to Table 1 (Step 30) to give the ammonium salt of the title compound.

EXAMPLE 39

H-$\beta$Asp-DTyr(SO$_3$H)-Met-Gly-Trp-Met-Asp-Phe-NH$_2$

H-Phe-OCH$_2$-Pam-resin (Example 11) was sequentially coupled with Fmoc-Asp(OtBu)-OH, Fmoc-Met-OH, Fmoc-Trp-OH, Fmoc-Gly-OH, Fmoc-Met-OH, Fmoc-DTyr-OH (Example 2), and Boc-$\beta$Asp-(OtBu)-OH according to Table 1 (coupling Steps 3–4 followed by Fmoc removal Steps 16–20) to give Boc-$\beta$Asp(OtBu)-DTyr-Met-Gly-Trp Met-Asp(OtBu)-Phe-OCH$_2$-Pam-resin which was deprotected according to Table 1 (Steps 10–15) and coupled with Fmoc-OSu (1.1 g) according to Table 1 (Steps 8–9) to give Fmoc-$\beta$Asp-DTyr-Met-Gly-Trp-Met-Asp-Phe-OCH$_2$-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE and P-40 ODS-3, sequentially, according to Table 1 (Step 30) to give 121 mg of the ammonium salt of the title compound. Amino acid analysis following acid decomposition gave Asp 1.94 (2), Tyr

EXAMPLE 40

H-DAsp-DTyr(SO₃H)-Met-Gly-Trp-Met-Asp-Phe-NH₂

H-Phe-OCH₂-Pam-resin (Example 11) was sequentially coupled with Fmoc-Asp(OtBu)-OH, Fmoc-Met-OH, Fmoc-Trp-OH, Fmoc-Gly-OH, Fmoc-Met-OH, Fmoc-DTyr-OH (Example 2), and Fmoc-DAsp-(Ot-Bu)-OH according to Table 1 (coupling Steps 3–4 followed by Fmoc removal Steps 16–20) to give Fmoc-DAsp(OtBu)-DTyr-Met-Gly-Trp-Met-Asp(OtBu)-Phe-OCH₂-Pam-resin which was deprotected, sulfated, deprotected, and cleaved from the resin according to Table 1 (Steps 10–15, Steps 21–25, Steps 16–20, and then Steps 26–29 with ammonia) to give the title compound which was chromatographically purified on Trisacryl M DEAE and P-40 ODS-3, sequentially, according to Table 1 (Step 30) to give 100 mg of the ammonium salt of the title compound. Amino acid analysis following acid decomposition gave Asp 2.08 (2), Tyr 1.06 (1), Met 1.83 (2), Gly 1.05 (1), and Phe 1.04 (1). Infrared absorption spectrum showed a strong peak typical of a sulfuric acid ester at 1050 cm$^{-1}$. TLC R$_f$ 0.24.

EXAMPLE 41

Suc-DTyr(SO₃H)-Met-Gly-Trp-Met-Asp-Phe-NH₂

H-Phe-OCH₂-Pam-resin (Example 11) was sequentially coupled with Fmoc-Asp(OtBu)-OH, Fmoc-Met-OH, Fmoc-Trp-OH, Fmoc-Gly-OH, Fmoc-Met-OH, Fmoc-DTyr-OH (Example 2) according to Table 1 (coupling Steps 3–4 followed by Fmoc removal Steps 16–20) to give H-DTyr-Met-Gly-Trp-Met-Asp(OtBu)-Phe-OCH₂-Pam-resin which was coupled with succinic anhydride (0.6 g, 6 mmole, in DMF) according to Table 1 (Steps 8–9) to give Suc-DTyr-Met-Gly-Trp-Met-Asp(OtBu)-Phe-OCH₂-Pam-resin which was deprotected, sulfated, and cleaved from the resin according to Table 1 (Steps 10–15, Steps 21–25, and then Steps 26–29 with ammonia) to give the title compound which was chromatographically purified on Trisacryl M DEAE and P40 ODS-3, sequentially, according to Table 1 (Step 30) to give 290 mg of the ammonium salt of the title compound.

Amino acid analysis following acid decomposition gave Asp 1.08 (1), Tyr 1.04 (1), Met 1.70 (2), Gly 1.14 (1), and Phe 1.03 (1). Infrared absorption spectrum showed a strong peak typical of a sulfuric acid ester at 1050 cm$^{-1}$. TLC R$_f$ 0.51.

EXAMPLE 42

H-Asp-Tyr(SO₃H)-Ile-Gly-Trp-Ile-Asp-Phe-NH₂

H-Phe-OCH₂-Pam-resin (Example 11) was sequentially coupled with Fmoc-Asp(OTBu)-OH, Fmoc-Ile-OH, Fmoc-Trp-OH, Fmoc-Gly-OH, Fmoc-Ile-OH, Fmoc-Tyr(tBu)-OH, and Fmoc-Asp(OtBu)-OH according to Table 1 (coupling Steps 3–4 followed by Fmoc removal Steps 16–20) to give Fmoc-Asp(OtBu)-Tyr(tBu)-Ile-Gly-Trp-Ile-Asp(OtBu)-Phe-OCH₂-Pam-resin which was deprotected, sulfated, deprotected, and cleaved from the resin according to Table 1 (Steps 10–15, Steps 21–25, Steps 16–20, and then Steps 26–29 with ammonia) to give the title compound which was chromatographically purified on Amberlite XAD-2, Trisacryl M DEAE, and P-40 ODS-3, sequentially, according to Table 1 (Step 30) to give 370 mg of the ammonium salt of the title compound. Amino acid analysis following acid decomposition gave Asp 2.05 (2), Tyr 1.00 (1), Ile 1.95 (2), Gly 1.00 (1), and Phe 1.00 (1). Infrared absorption spectrum showed a strong peak typical of a sulfuric acid ester at 1050 cm$^{-1}$. TLC R$_f$ 0.33.

EXAMPLE 43

H-Asp-Tyr(SO₃H)-Lys-Gly-Trp-Lys-Asp-Phe-NH₂

H-Phe-OCH₂-Pam-resin (Example 11) was sequentially coupled with Fmoc-Asp(OtBu)-OH, Fmoc-Lys(Boc)-OH, Fmoc-Trp-OH, Fmoc-Gly-OH, Fmoc-Lys(Boc)-OH, Fmoc-Tyr(tBu)-OH, and Fmoc-Asp(OtBu)-OH according to Table 1 (coupling Steps 3–4 followed by Fmoc removal Steps 16–20) to give Fmoc-Asp-(OtBu)-Tyr(tBu)-Lys(Boc)-Gly-Trp-Lys(Boc)-Asp(OtBu)-Phe-OCH₂-Pam-resin which was deprotected, sulfated, deprotected, and cleaved from the resin according to Table 1 (Steps 10–15, Steps 21–25, Steps 16–20, and then Steps 26–29 with ammonia) to give the title compound which was chromatographically purified on Amberlite XAD-2, Trisacryl M DEAE, and P-40 ODS-3, sequentially, according to Table 1 (Step 30) to give 61 mg of the ammonium salt of the title compound. Amino acid analysis following acid decomposition gave Asp 1.98 (2), Tyr 1.01 (1), Lys 2.00 (2), Gly 0.99 (1), and Phe 1.02 (1). Infrared absorption spectrum showed a strong peak typical of a sulfuric acid ester at 1050 cm$^{-1}$. TLC R$_f$ 0.10.

EXAMPLE 44

Hpp(SO₃H)-Met-DAla-Trp-Met-Asp-Phe-NH₂

H-Phe-OCH₂-Pam-resin (Example 11) was sequentially coupled with Fmoc-Asp(OtBu)-OH, Fmoc-Met-OH, Fmoc-Trp-OH, Fmoc-DAla-OH, and Fmoc-Met-OH according to Table 1 (coupling Steps 5–7 followed by Fmoc removal Steps 16–20) to give H-Met-DAla-Trp-Met-Asp(OtBu)-Phe-OCH₂-Pam-resin which was coupled with Hpp-OSu according to Table 1 (Steps 8–9) to give Hpp-Met-DAla-Trp-Met-Asp(OtBu)-Phe-OCH₂-Pam-resin which was deprotected, sulfated, and cleaved from the resin according to Table 1 (Steps 10–15, Steps 21–25, and then Steps 26–29 with ammonia) to give the title compound which was chromatographically purified on Trisacryl M DEAE, and P-40 ODS-3, sequentially, according to Table 1 (Step 30) to give 140 mg of the ammonium salt of the title compound. Amino acid analysis following acid decomposition gave Asp 1.02 (1), Met 1.97 (2), Ala 0.98 (1), and Phe 1.03 (1).

Infrared absorption spectrum showed a strong peak typical of a sulfuric acid ester at 1050 cm$^{-1}$. TLC R$_f$ 0.52.

EXAMPLE 45

Suc-Tyr(SO₃H)-Ahx-Gly-Trp-Ahx-Asp-Phe-NH₂

H-Phe-OCH₂-Pam-resin (Example 11) was sequentially coupled with Fmoc-Asp(OtBu)-OH, Fmoc-Ahx-OH, Fmoc-Trp-OH, Fmoc-Gly-OH, Fmoc-Ahx-OH, and Fmoc-Tyr(tBu)-OH according to Table 1 (coupling Steps 5–7 followed by Fmoc removal Steps 16–20) to give H-Tyr(tBu)-Ahx-Gly-Trp-Ahx-Asp(OtBu)-Phe-OCH₂-Pam-resin which was coupled with succinic anhydride (0.6 g, 6 mmole, in DMF) according to Table 1 (Steps 8-9) to give Suc-Tyr(tBu)-Ahx-Gly-Trp-Ahx-Asp(OtBu)-Phe-OCH$_2$-Pam-resin which was deprotected, sulfated, and cleaved from the resin according to Table 1 (Steps 10-15, Steps 21-25, and then Steps 26-29 with ammonia) to give the title compound which was chromatographically purified on Amberlite XAD-2, Trisacryl M DEAE, and P-40 ODS-3, sequentially, according to Table 1 (Step 30) to give 240 mg of the ammonium salt of the title compound. Amino acid analysis following acid decomposition gave Asp 1.01 (1), Tyr 0.95 (1), Ahx 2.10 (2), Gly 1.06 (1), and Phe 0.88 (1). Infrared absorption spectrum showed a strong peak typical of a sulfuric acid ester at 1050 cm$^{-1}$. TLC R$_f$ 0.36.

EXAMPLE 46

H-$\beta$Asp-Tyr(SO$_3$H)-Met-Gly-Trp-Met-Asp-MePhe-NH$_2$

H-MePhe-OCH$_2$-Pam-resin (Example 12) was sequentially coupled with Fmoc-Met-Asp(OtBu)-OH (Example 10), Fmoc-Trp-OH, Fmoc-Gly-OH, Fmoc-Met-OH, Fmoc-Tyr(tBu)-OH, and Boc-$\beta$Asp(OtBu)-OH according to Table 1 (coupling Steps 5-7 followed by Fmoc removal Steps 16-20) to give Boc-$\beta$Asp-(OtBu)-Tyr(tBu)-Met-Gly-Trp-Met-Asp(OtBu)-MePhe-OCH$_2$-Pam-resin which was deprotected according to Table 1 (Steps 10-15) and coupled with Fmoc-OSu (1.1 g) according to Table 1 (8-9) to give Fmoc-$\beta$Asp-Tyr-Met-Gly-Trp-Met-Asp-MePhe-OCH$_2$-Pam-resin which was sulfated, deprotected, and cleaved from the resin according to Table 1 (Steps 21-25, Steps 16-20, and then Steps 26-29 with ammonia) to give the title compound which was chromatographically purified on Amberlite XAD-2, Trisacryl M DEAE, and P-40 ODS-3, sequentially, according to Table 1 (Step 30) to give 72 mg of the ammonium salt of the title compound. Amino acid analysis following acid decomposition gave Asp 2.03 (2), Tyr 1.05 (1), Met 1.85 (2), and Gly 1.10 (1). Infrared absorption spectrum showed a strong peak typical of a sulfuric acid ester at 1050 cm$^{-1}$. TLC R$_f$ 0.33.

EXAMPLE 47

H-DAsp-Tyr(SO$_3$H)-Met-Gly-Trp-Met-Asp-MePhe-NH$_2$

H-MePhe-OCH$_2$-Pam-resin (Example 12) was sequentially coupled with Fmoc-Met-Asp(OtBu)-OH (Example 10), Fmoc-Trp-OH, Fmoc-Gly-OH, Fmoc-Met-OH, Fmoc-Tyr(tBu)-OH, and Fmoc-DAsp(OtBu)-OH according to Table 1 (coupling Steps 3-4 followed by Fmoc removal Steps 16-20) to give Fmoc-DAsp-(OtBu)-Tyr(tBu)-Met-Gly-Trp-Met-Asp(OtBu)-MePhe-OCH$_2$-Pam-resin which was deprotected, sulfated, deprotected, and cleaved from the resin according to Table 1 (Steps 10-15, Steps 21-25, Steps 16-20, and then Steps 26-29 with ammonia) to give the title compound which was chromatographically purified on Trisacryl M DEAE, and P-40 ODS-3, sequentially, according to Table 1 (Step 30) to give 110 mg of the ammonium salt of the title compound. Amino acid analysis following acid decomposition gave Asp 2.01 (2), Tyr 1.01 (1), Met 1.91 (2), and Gly 1.07 (1). Infrared absorption spectrum showed a strong peak typical of a sulfuric acid ester at 1050 cm$^{-1}$. TLC R$_f$ 0.35.

EXAMPLE 48

For-Tyr(SO$_3$H)-Met-Gly-Trp-Met-Asp-MePhe-NH$_2$

H-MePhe-OCH$_2$-Pam-resin (Example 12) was sequentially coupled with Fmoc-Met-Asp(OtBu)-OH (Example 10), Fmoc-Trp-OH, Fmoc-Gly-OH, and Fmoc-Met-OH according to Table 1 (coupling Steps 5-7 followed by Fmoc removal Steps 16-20) to give Fmoc-Met-Gly-Trp-Met-Asp(OtBu)-MePhe-OCH$_2$-Pam-resin which was deprotected according to Table 1 (Steps 10-20) and coupled with For-Tyr-OH according to Table 1 (Steps 5-7) to give For-Tyr-Met-Gly-Trp-Met-Asp-MePhe-OCH$_2$-Pam-resin which was sulfated and cleaved from the resin according to Table 1 (Steps 21-25 and then Steps 26-29 with ammonia) to give the title compound which was chromatographically purified on Amberlite XAD-2, Trisacryl M DEAE, and P-40 ODS-3, sequentially, according to Table 1 (Step 30) to give 78 mg of the ammonium salt of the title compound. Amino acid analysis following acid decomposition gave Asp 1.02 (1), Tyr 1.01 (1), Met 1.95 (2), and Gly 1.02 (I). Infrared absorption spectrum showed a strong peak typical of a sulfuric acid ester at 1050 cm$^{-1}$. TLC R$_f$ 0.45.

EXAMPLE 49 iBuOCO-Tyr(SO$_3$H)-Met-Gly-Trp-Met-Asp-MePhe-NH$_2$

H-MePhe-OCH$_2$-Pam-resin (Example 12) was sequentially coupled with Fmoc-Met-Asp(OtBu)-OH (Example 10), Fmoc-Trp-OH, Fmoc-Gly-OH, Fmoc-Met-OH, and Fmoc-Tyr(tBu)-OH according to Table 1 (coupling Steps 5-7 followed by Fmoc removal Steps 16-20) to give H-Tyr(tBu)-Met-Gly-Trp-Met-Asp(OtBu)-MePhe-OCH$_2$-Pam-resin which was coupled with iBuOCO-OSu (Example 1) according to Table 1 (Steps 8-9) to give iBuOCO-Tyr(tBu)-Met-Gly-Trp-Met-Asp(OtBu)-MePhe-OCH$_2$-Pam-resin which was deprotected, sulfated, and cleaved from the resin according to Table 1 (Steps 10-15, Steps 21-25, and then Steps 26-29 with ammonia) to give the title compound which was chromatographically purified on Amberlite XAD-2, Trisacryl M DEAE, and P-40 ODS-3, sequentially, according to Table 1 (Step 30) to give 302 mg of the ammonium salt of the title compound. Amino acid analysis following acid decomposition gave Asp 1.03 (1), Tyr 1.02 (1), Met 1.91 (2), and Gly 1.04 (1). Infrared absorption spectrum showed a strong peak typical of a sulfuric acid ester at 1050 cm$^{-1}$. TLC R$_f$ 0.67.

EXAMPLE 50

H-Asp-DTyr(SOH$_3$)-Met-Gly-Trp-Met-Asp-MePhe-NH$_2$

H-MePhe-OCH$_2$-Pam-resin (Example 12) was sequentially coupled with Fmoc-Met-Asp(OtBu)-OH (Example 10), Fmoc-Trp-OH, Fmoc-Gly-OH, Fmoc-Met-OH, Fmoc-DTyr(tBu)-OH, and Fmoc-Asp(OtBu)-OH according to Table 1 (coupling Steps 3-4 followed by Fmoc removal Steps 16-20) to give Fmoc-Asp-(OtBu)-DTyr(tBu)-Met-Gly-Trp-Met-Asp(OtBu)-MePhe-OCH$_2$-Pam which was deprotected, sulfated, deprotected, and cleaved from the resin according to Table 1 (Steps 10-15, Steps 21-25, Steps 16-20, and then Steps 26-29 with ammonia) to give the title compound which was chromatographically purified on Trisacryl M DEAE and P-40 ODS-3, sequentially, according to Table 1 (Step 30) to give 29 mg of the ammonium salt of the title compound Amino acid analysis following acid decomposition gave Asp 2.02 (2), Tyr 0.97 (1), Met 1.93 (2), and Gly 1.07 (I). Infrared absorption spectrum showed a strong peak typical of a sulfuric acid ester at 1050 cm$^{-1}$ TLC $R_f$ 0.28.

EXAMPLE 51

Hpp(SO$_3$H)-Met-Gly-Trp-Met-Asp-MePhe-NH$_2$

H-MePhe-OCH$_2$-Pam-resin (Example 12) was sequentially coupled with Fmoc-Met-Asp(OtBu)-OH (Example 10), Fmoc-Trp-OH, Fmoc-Gly-OH, and Fmoc-Met-OH according to Table 1 (coupling Steps 3-4 followed by Fmoc removal Steps 16-20) to give H-Met-Gly-Trp-Met-Asp(OtBu)-MePhe-OCH$_2$-Pam-resin which was coupled with 3-(4-hydroxyphenyl)propionic acid N-hydroxysuccinimide ester (Hpp-OSu) according to Table 1 (Steps 8-9) to give Hpp-Met-Gly-Trp-Met-Asp(OtBu)-MePhe-OCH$_2$-Pam-resin which was deprotected, sulfated, and cleaved from the resin according to Table 1 (Steps 10-15, Steps 21-25, and then Steps 26-29 with ammonia) to give the title compound which was chromatographically purified on Trisacryl. M DEAE, and P-40 ODS-3, sequentially, according to Table 1 (Step 30) to give 170 mg of the ammonium salt of the title compound. Amino acid analysis following acid decomposition gave Asp 1.02 (1), Met 1.97 (2), and Gly 1.01 (1). Infrared absorption spectrum showed a strong peak typical of a sulfuric acid ester at 1050 cm$^{-1}$. TLC $R_f$ 0.58.

EXAMPLE 52

Hpp(SO$_3$H)-Met-DAla-Trp-Met-Asp-MePhe-NH$_2$

H-MePhe-OCH$_2$-Pam-resin (Example 12) was sequentially coupled with Fmoc-Met-Asp(OtBu)-OH (Example 10), Fmoc-Trp-OH, Fmoc-DAla-OH, and Fmoc-Met-OH according to Table 1 (coupling Steps 5-7 followed by Fmoc removal Steps 16-20) to give H-Met-Gly-DAla-Trp-Met-Asp(OtBu)-MePhe-OCH$_2$-Pam-resin which was coupled with Hpp-OSu according to Table 1 (Steps 8-9) to give Hpp-Met-DAla-Trp-Met-Asp(OtBu)-MePhe-OCH$_2$-Pam-resin which was deprotected, sulfated, and cleaved from the resin according to Table 1 (Steps 10-15, Steps 21-25, and then Steps 26-29 with ammonia) to give the title compound which was chromatographically purified on Amberlite XAD-2, Trisacryl M DEAE, and P-40 ODS-3, sequentially, according to Table 1 (Step 30) to give 84 mg of the ammonium salt of the title compound. Amino acid analysis following acid decomposition gave Asp 0.99 (1), Met 1.94 (2), and Ala 1.08 (1). Infrared absorption spectrum showed a strong peak typical of a sulfuric acid ester at 1050 cm$^{-}$. TLC $R_f$20 0.49.

EXAMPLE 53

PrOCO-Tyr(SO$_3$H)-Met-Gly-Trp-Met-Asp-Phe-NH$_2$

H-Phe-OCH$_2$-Pam-resin (Example 11) was sequentially coupled with Fmoc-Met-Asp(OtBu)-OH, Fmoc-Met-OH, Fmoc-Trp-OH, Fmoc-Gly-OH, Fmoc-Met-OH, and Fmoc-Tyr(tBu)-OH according to Table 1 (coupling Steps 5-7 followed by Fmoc removal Steps 16-20) to give H-Tyr-(tBu)-Met-Gly-Trp-Met-Asp(OtBu)-Phe-OCH$_2$-Pam-resin which was coupled with PrOCO-OSu (mp 31°-34° C., prepared according to the procedure of Example 1 except that propyl chloroformate was substituted for isobutyl chloroformate) according to Table 1 (Steps 8-9) to give PrOCO-Tyr(-tBu)-Met-Gly-Trp-Met-Asp(OtBu)-Phe-OCH$_2$-Pam-resin which was deprotected, sulfated, and cleaved from the resin according to Table 1 (Steps 10-15, Steps 21-25and 5 then Steps 26-29 with ammonia) to give the title compound which was chromatographically purified on Amberlite XAD-2 and P-40 ODS-3, sequentially, according to Table 1 (Step 30) to give 270 mg of the ammonium salt of the title compound. Amino acid analysis following acid decomposition gave Asp 1.01 (1), Tyr 1.03 (1), Met 1.87 (2), Gly 1.02 (1), and Phe 1.06 (1). Infrared absorption spectrum showed a strong peak typical of a sulfuric acid ester at 1050 cm$^{-1}$ TLC $R_f$ 0.45.

EXAMPLE 54

EtOCO-Tyr(SO$_3$H)-Met-Gly-Trp-Met-Asp-Phe-NH$_2$

H-Phe-OCH$_2$-Pam-resin (Example 11) was sequentially coupled with Fmoc-Asp(OtBu)-OH, Fmoc-Met-OH, Fmoc-Trp-OH, Fmoc-Gly-OH Fmoc-Met-OH, and Fmoc-Tyr(tBu)-OH according to Table 1 (coupling Steps 5-7 followed by Fmoc removal Steps 16-20) to give H-Tyr-(tBu)-Met-Gly-Trp-Met-Asp(OtBu)-Phe-OCH$_2$-Pam-resin which was coupled with EtOCO-OSu (mp 52°-54.5° C., prepared according to the procedure of Example except that ethyl chloroformate was substituted for isobutyl chloroformate) according to Table 1 (Steps 8-9) to give EtOCO-Tyr(tBu)-Met-Gly-Trp-Met-Asp(OtBu)-Phe-OCH$_2$-Pam-resin which was deprotected, sulfated, and cleaved from the resin according to Table 1 (Steps 10-15, Steps 21-25, and then Steps 26-29 with ammonia) to give the title compound which was chromatographically purified on Amberlite XAD-2 and P-40 ODS-3, sequentially, according to Table 1 (Step 30) to give 300 mg of the ammonium salt of the title compound. Amino acid analysis following acid decomposition gave Asp 1.02 (1), Tyr 1.01 (1), Met 1.91 (2), Gly 1.02 (1), and Phe 1.04 (1). Infrared absorption spectrum showed a strong peak typical of a sulfuric acid ester at 1050 cm$^{-1}$. TLC $R_f$0.44.

EXAMPLE 55

MeOCO-Tyr(SO$_3$H)-Met-Gly-Trp-Met-Asp-Phe-NH$_2$

H-Phe-OCH$_2$-Pam-resin (Example 11) was sequentially coupled with Fmoc-Asp(OtBu)-OH, Fmoc-Met-OH, Fmoc-Trp-OH, Fmoc-Gly-OH, Fmoc-Met-OH, and Fmoc-Tyr(tBu)-OH according to Table 1 (coupling Steps 5-7 followed by Fmoc removal Steps 16-20) to give H-Tyr-(tBu)-Met-Gly-Trp-Met-Asp(OtBu)-Phe-OCH$_2$-Pam-resin which was coupled with MeOCO-OSu (mp 87°-89° C., prepared according to the procedure of Example 1 except that methyl chloroformate was substituted for isobutyl chloroformate) according to Table 1 (Steps 8-9) to give MeOCO-Tyr(tBu)-Met-Gly-Trp-Met-Asp(OtBu)-Phe-OCH$_2$-Pam-resin which was deprotected, sulfated, and cleaved from the resin according to Table 1 (Steps 10-15, Steps 21-25, and then Steps 26-29 with ammonia) to give the title compound which was chromatographically purified on Amberlite XAD-2 and P-40 ODS-3, sequentially, according to Table 1 (Step 30) to give 270 mg of the ammonium salt of the title compound. Amino acid analysis following acid decomposition gave Asp 1.04 (1), Tyr 1.05 (1), Met 1.82 (2), Gly 1.03 (1), and Phe 1.06 (1). Infrared absorption spectrum showed a strong peak typical of a sulfuric acid ester at 1050 cm$^{-1}$. TLC $R_f$ 0.44.

EXAMPLE 56

H-βAsp-Tyr(SO$_3$H)-Met-Gly-Trp-Met-Asp-Phe-NH$_2$

The title compound has previously been prepared (Digestive Diseases, 15, 149–156 (1970)). H-Phe-OCH$_2$-Pam-resin (Example 11) was sequentially coupled with Fmoc-Asp(OtBu)OH, Fmoc-Met-OH, Fmoc-Trp-OH, Fmoc-Gly-OH, Fmoc-Met-OH, FmOc-Tyr-OH (Example 3), and Boc-βAsp(OtBu)-OH according to Table 1 (coupling Steps 3–4 followed by Fmoc removal Steps 16–20) to provide Boc-βAsp(OtBu)-Tyr-Met-Gly-Trp-Met-Asp(OtBu)-Phe-OCH$_2$-Pam-resin which was sulfated, deprotected, and cleaved from the resin according to Table 1 (Steps 21–25, Steps 10–15, and then Steps 26–29 with ammonia to give the title compound which was chromatographically purified on Trisacryl M DEAE according to Table 1 (Step 30) to give 283 mg of the ammonium salt of the title compound. Amino acid analysis following acid decomposition gave Asp 2.03 (2), Tyr 0.94 (1), Met 2.08 (2), Gly 0.99 (1), and Phe 0.96 (1). Infrared absorption spectrum showed a strong peak typical of a sulfuric acid ester at 1050 cm$^{-1}$. TLC R$_f$ 0.52.

EXAMPLE 57

H-Tyr(SO$_3$H)-Met-Gly-Trp-Met-Asp-Phe-NH$_2$

The title compound has previously been prepared (U.S. Pat. Nos. 3,839,315 and 3,705,140). H-Phe-OCH$_2$-Pam-resin (Example 11) was sequentially coupled with Fmoc-Asp(OtBu)-OH, Fmoc-Met-OH, Fmoc-Trp-OH, Fmoc-Gly-OH, Fmoc-Met-OH, and Boc-Tyr-OH according to Table 1 (coupling Steps 3–4 followed by Fmoc removal Steps 16–20) to provide Boc-Tyr-Met-Gly-Trp-Met-Asp(OtBu)-Phe-OCH$_2$-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE according to Table 1 (Step 30) to give 240 mg of the ammonium salt of the title compound. Amino acid analysis following acid decomposition gave Asp 1.05 (1), Tyr 1.04 (1), Met 2.10 (2), Gly 1.07 (1), and Phe 1.08 (1). Infrared absorption spectrum showed a strong peak typical of a sulfuric acid ester at 1050 cm$^{-1}$. TLC R$_f$ 0.55.

EXAMPLE 58

Suc-Tyr(SO$_3$H)-Met-Gly-Trp-Met-Asp-Phe-NH$_2$

The title compound has previously been prepared (European Patent Application 0107860). H-Phe-OCH$_2$-Pam-resin (Example 11) was sequentially coupled with Fmoc-Asp(OtBu)-OH, Fmoc-Met-OH, Fmoc-Trp-OH, Fmoc-Gly-OH, Fmoc-Met-OH, and Fmoc-Tyr-OH (Example 3) according to Table 1 (coupling Steps 3–4 followed by Fmoc removal Steps 16–20) to provide H-Tyr-Met-Gly-Trp-Met-Asp(OtBu)-Phe-OCH$_2$-Pam-resin which was coupled with succinic anhydride in DMF according to Table 1 (Steps 8–9) to give Suc-Tyr-Met-Gly-Trp-Met-Asp(OtBu)-Phe-OCH$_2$-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE according to Table 1 (Step 30) to give 246 mg of the ammonium salt of the title compound. Amino acid analysis following acid decomposition gave Asp 1.03 (1), Tyr 0.95 (1), Met 2.08 (2), Gly 0.98 (1), and Phe 0.96 (1). Infrared absorption spectrum showed a strong peak typical of a sulfuric acid ester at 1050 cm$^{-1}$ TLC R$_f$ 0.54.

EXAMPLE 59

Hpp(SO$_3$H)-Met-Gly-Trp-Met-Asp-Phe-NH$_2$

The title compound has previously been prepared (Int. J. Peptide Protein Res., 16, 402–411 (1980)). H-Phe-OCH$_2$-Pamresin (Example 11) was sequentially coupled with Fmoc-Asp-(OtBu)-OH, Fmoc-Met-OH, Fmoc-Trp-OH, Fmoc-Gly-OH, and Fmoc-Met-OH according to Table 1 (coupling Steps 3–4 followed by Fmoc removal Steps 16–20) to provide H-Met-Gly-Trp-Met-Asp(OtBu)-Phe-OCH$_2$-Pam-resin which was coupled with Hpp-OSu in DMF according to Table 1 (Steps 8–9) to give Hpp-Met-Gly-Trp-Met-Asp(OtBu)-Phe-OCH$_2$-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE according to Table 1 (Step 30) to give 65 mg of the ammonium salt of the title compound. Amino acid analysis following acid decomposition gave Asp 1.04 (1), Met 2.04 (2), Gly 0.95 (1), and Phe 1.00 (1). Infrared absorption spectrum showed a strong peak typical of a sulfuric acid ester at 1050 cm$^{-1}$. TLC R$_f$ 0.47.

EXAMPLE 60

H-Asp-Tyr(SO$_3$H)-Ahx-Gly-Trp-Met-Asp-Phe-NH$_2$

The title compound has previously been prepared (U.S. Pat. No. 3,892,726). H-Phe-OCH$_2$-Pam-resin (Example 11) was sequentially coupled with Fmoc-Asp(OtBu)-OH, Fmoc-Met-OH, Fmoc-Trp-OH, Fmoc-Gly-OH, Fmoc-Ahx-OH, Fmoc-Tyr(tBu)-OH, and Fmoc-Asp(OtBu)-OH according to Table 1 (coupling Steps 5–7 followed by Fmoc removal Steps 16–20) to provide Fmoc-Asp(OtBu)-Tyr(tBu)-Ahx-Gly-Trp-Met-Asp(OtBu)-Phe-OCH$_2$-Pam-resin which was deprotected, sulfated, deprotected, and cleaved from the resin according to Table 1 (Steps 10–15, Steps 21–25, Steps 16–20, and then Steps 26–29 with ammonia) to give the title compound which was chromatographically purified on Trisacryl M DEAE and P-40 ODS-3, sequentially, according to Table 1 (Step 30) to give 188 mg of the ammonium salt of the title compound. Amino acid analysis following acid decomposition gave Asp 1.97 (2), Tyr 0.99 (1), Ahx 1.06 (1), Gly 1.07 (1), Met 0.93 (1), and Phe 0.98 (1). Infrared absorption spectrum showed a strong peak typical of a sulfuric acid ester at 1050 cm$^{-1}$. TLC R$_f$ 0.57.

EXAMPLE 61

H-Asp-Tyr(SO$_3$H)-Met-Gly-DTrp-Met-Asp-Phe-NH$_2$

The title compound has previously been prepared (U.S. Pat. No. 3,892,726). H-Phe-OCH$_2$-Pam-resin (Example 11) was sequentially coupled with Fmoc-Asp(OtBu)-OH, Fmoc-Met-OH, Fmoc-DTrp-OH, Fmoc-Gly-OH, Fmoc-Met-OH, Fmoc-Tyr-OH (Example 3), and Boc-Asp(OtBu)-OH according to Table 1 (coupling Steps 3–4 followed by Fmoc removal Steps 16–20) to provide Boc-Asp(OtBu)-Tyr-Met-Gly-DTrp-Met-Asp(OtBu)-Phe- OCH$_2$-Pam-resin which was sulfated, deprotected, and cleaved the resin according to Table 1 (Steps 21–25, Steps 10–15, and then Steps 26–29 with ammonia) to give the title compound which was chromatographically purified on Trisacryl M DEAE according to Table 1 (Step 30) to give 314 mg of the ammonium salt of the title compound. Amino acid analysis following acid decomposition gave Asp 2.07 (2), Tyr 1.01 (1), Met 2.01 (2), Gly 1.06 (1), and Phe 0.98 (1). Infrared absorption spectrum showed a strong peak typical of a sulfuric acid ester at 1050 cm$^{-1}$. TLC R$_f$ 0.30.

EXAMPLE 62

H-Asp-Tyr(SO$_3$H)-Met-Gly-Trp-Ahx-Asp-Phe-NH$_2$

The title compound has previously been prepared (U.S. Pat. No. 3,892,726). H-Phe-OCH$_2$-Pam-resin (Example 11) was sequentially coupled with Fmoc-Asp(OtBu)-OH, Fmoc-Ahx-OH, Fmoc-Trp-OH, Fmoc-Gly-OH, Fmoc-Met-OH, Fmoc-Tyr-OH (Example 3), and Boc-Asp(OtBu)-OH according to Table 1 (coupling Steps 3–4 followed by Fmoc removal Steps 16–20) to provide Boc-Asp(OtBu)-Tyr-Met-Gly-Trp-Ahx-Asp(OtBu)-Phe-OCH$_2$-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE according to Table 1 (Step 30) to give 87 mg of the ammonium salt of the title compound. Amino acid analysis following acid decomposition gave Asp 2.11 (2), Tyr 1.00 (1), Met 1.11 (1), Gly 1.02 (1), Ahx 1.04 (1), and Phe 0.99 (1). Infrared absorption spectrum showed a strong peak typical of a sulfuric acid ester at 1050 cm$^{-1}$. TLC R$_f$ 0.23.

EXAMPLE 63

H-Asp-Tyr(SO$_3$H)-Met-Gly-Trp-Met

The title compound has previously been prepared (U.S. Pat. No. 3,892,726). H-DPhe-OCH$_2$-Pam-resin {prepared in an analogous fashion as H-Phe-OCH$_2$-Pam-resin [Example 11, Boc-Phe-(4-oxymethylphenyl)acetic acid replaced with Boc-DPhe(4-oxymethylphenyl)acetic acid] from Boc-DPhe-(4-oxymethylphenyl)acetic acid [Example 5, Boc-MePhe-OH replaced with Boc-DPhe-OH]} was sequentially coupled with Fmoc-Asp(OtBu)OH, Fmoc-Met-OH, Fmoc-Trp-OH, Fmoc-Gly-OH, Fmoc-Met-OH, Fmoc-Tyr-OH (Example 3), and Boc-Asp(OtBu)-OH according to Table 1 (coupling Steps 3–4 followed by Fmoc removal Steps 16–20) to provide Boc-Asp(OtBu)-Tyr-Met-Gly-Trp-Met-Asp-(OtBu)-DPhe-OCH:-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE according to Table 1 (Step 30) to give 141 mg of the ammonium salt of the title compound. Amino acid analysis following acid decomposition gave Asp 1.97 (2), Tyr 0.98 (1), Met 2.03 (2), Gly 1.09 (1), and Phe 1.05 (1) Infrared absorption spectrum showed a strong peak typical of a sulfuric acid ester at 1050 cm$^{-1}$. TLC R$_f$ 0.32.

EXAMPLE 64

H-Asp-Tyr(SO$_3$H)-MetO-Gly-Trp-MetO-Asp-Phe-NH$_2$

The title compound has previously been prepared (Nobel, Symp. 16, (Front. Gastrointest. Horm. Res.), 41–56 (1973)). H-Phe-OCH$_2$-Pam-resin (Example 11) was sequentially coupled with Fmoc-Asp(OtBu)-OH, Fmoc-MetO-OH, Fmoc-Trp-OH, Fmoc-Gly-OH, Fmoc-MetO-OH, Fmoc-Tyr-OH (Example 3), and Boc-Asp(OtBu)-OH according to Table 1 (coupling Steps 3–4 followed by Fmoc removal Steps 16–20) to provide Boc-Asp(OtBu)-Tyr-MetO-Gly-Trp-MetO-AspOtBu)-Phe-OCH$_2$-Pam-resin resin which was sulfated, deprotected, and cleaved from the resin according to Table 1 (Steps 2–25, Steps 10–15, and then Steps 26–29 with ammonia) to give the title compound which was chromatographically purified on Trisacryl M DEAE according to Table 1 (Step 30) to give 162 mg of the ammonium salt of the title compound. Amino acid analysis following acid decomposition gave Asp 2.09 (2), Tyr 1.00 (1), MetO 1.83 (2), Gly 1.08 (1), and Phe 1.08 (1). Infrared absorption spectrum showed a strong peak typical of a sulfuric acid ester at 1050 cm$^{-1}$. TLC R$_f$0.14.

EXAMPLE 65

H-Asp-Tyr(SO$_3$H)-Ahx-Gly-Trp-Ahx-Asp-Phe-NH$_2$

The title compound has previously been prepared (U.S. Pat. No. 3,892,726). H-Phe-OCH$_2$-Pam-resin (Example 11) was sequentially coupled with Fmoc-Asp(OtBu)-OH, Fmoc-Ahx-OH, Fmoc-Trp-OH, Fmoc-Gly-OH, Fmoc-Ahx-OH, Fmoc-Tyr-OH (Example 3), and Boc-Asp(OtBu)-OH according to Table 1 (coupling Steps 3–4 followed by Fmoc removal Steps 16–20) to provide Boc-Asp(OtBu)-Tyr-Ahx-Gly-Trp-Ahx-Asp(OtBu)-Phe-OCH$_2$-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE accordin to Table 1 (Step 30) to give 94 pmg of the ammonium salt of the title compound. Amino acid analysis following acid decomposition gave Asp 2.18 (2), Tyr 1.06 (1), Ahx 2.01 (2), Gly 1.10 (1), and Phe 0.94 (1). Infrared absorption spectrum showed a strong peak typical of a sulfuric acid ester at 1050 cm$^{-1}$. TLC R$_f$ 0.32.

EXAMPLE 66

H-Asp-Tyr(SO$_3$H)-Leu-Gly-Trp-Leu-Asp-Phe-NH$_2$

The title compound has previously been prepared (Digestive Diseases 15, 149–156 (1970)). H-Phe-OCH$_2$-Pam-resin (Example 11) was sequentially coupled with Fmoc-Asp(OtBu)OH, Fmoc-Leu-OH, Fmoc-Trp-OH, Fmoc-Gly-OH, Fmoc-Leu-OH, Fmoc-Tyr(tBu)-OH, and Fmoc-Asp(OtBu)-OH according to Table 1 (coupling Steps 3–4 followed by Fmoc removal Steps 16–20) to provide Fmoc-Asp(OtBu)-Tyr(tBu)-Leu-Gly-Trp-Leu-Asp- (OtBu)-Phe-OCH$_2$-Pam-resin which was deprotected, sulfated, deprotected, and cleaved from the resin according to Table 1 (Steps 10–15, Steps 21–25, Steps 16–20, and then Steps 26–29 with ammonia) to give the title compound which was chromatographically purified on Amberlite XAD-2, Trisacryl M DEAE, and P-40 ODS-3, sequentially, according to Table 1 (Step 30) to give 150 mg of the ammonium salt of the title compound. Amino acid analysis following acid decomposition gave Asp 2.02 (2), Tyr 0.99 (1), Leu 2.02 (2), Gly 0.98 (1), and Phe 0.98 (1). Infrared absorption spectrum showed a strong peak typical of a sulfuric acid ester at 1050 cm$^{-1}$. TLC R$_f$0.35.

EXAMPLE 67

For-Tyr(SO$_3$H)-Met-Gly-Trp-Met-Asp-Phe-NH$_2$

The title compound has previously been prepared (U.S. Pat. No. 3,705,140). H-Phe-OCH$_2$-Pam-resin (Example 11) was sequentially coupled with Fmoc-Asp(OtBu)-OH, Fmoc-Met-OH, Fmoc-Trp-OH, Fmoc-Gly-OH, and Fmoc-Met-OH according to Table 1 (coupling Steps 3–4 followed by Fmoc removal Steps 16–20) to provide H-Met-Gly-Trp-Met-Asp(OtBu)-Phe-OCH$_2$-Pam-resin which was deprotected according to Table 1 (Steps 10–15) to provide H-Met-Gly-Trp-Met-Asp-Phe-OCH$_2$-Pam-resin which was coupled with For-Tyr-OH according to Table 1 Steps 3–4) to give For-Tyr-Met-Gly-Trp-Met-Asp-Phe-OCH$_2$-Pam-resin which was sulfated and cleaved from the resin according to Table 1 (Steps 21–25 and then Steps 26–29 with ammonia) to give the title compound which was chromatographically purified on Trisacryl M DEAE and P-40 ODS-3, sequentially, according to Table 1 (Step 30) to give 30 mg of the ammonium salt of the title compound. Amino acid analysis following acid decomposition gave Asp 1.00 (1), Met 1.98 (2), Gly 1.07 (1), and Phe 1.00 (1). Infrared absorption spectrum showed a strong peak typical of a sulfuric acid ester at 1050 cm$^{-1}$. TLC R$_f$ 0.37.

EXAMPLE 68

H-Asp-Tyr(SO$_3$H)-MetO-Gly-Trp-Met-Asp-Phe-NH$_2$

H-Phe-OCH$_2$-Pam-resin (Example 11)was sequentially coupled with Fmoc-Asp(OtBu)-OH, Fmoc-Met-OH, Fmoc-Trp-OH, Fmoc-Gly-OH, and Fmoc-MetO-OH, and Fmoc-Tyr-OH (Example 3), and Boc-Asp(OtBu)-OH according to Table 1 (coupling Steps 3–4 followed by Fmoc removal Steps 16–20) to provide Boc-Asp(OtBu)-Tyr-MetO-Gly-Trp-Met-Asp(OtBu)-Phe-OCH$_2$-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE according to Table 1 (Step 30) to give 230 mg of the ammonium salt of the title compound. Infrared absorption spectrum showed a strong peak typical of a sulfuric acid ester at 1050 cm$^{-1}$. TLC R$_f$ 0.26.

EXAMPLE 69

H-Asp-Tyr(SO$_3$H)-Met-DAla-Trp-Met-Asp-Phe-NH$_2$

The title compound has previously been prepared (Peptides 1984, 383-385 (1984)). H-Phe-OCH$_2$-Pam-resin (Example 11) was sequentially coupled with Fmoc-Asp(OtBu)-OH, Fmoc-Met-OH, Fmoc-Trp-OH, Fmoc-DAla-OH, and Fmoc-Met-OH, Fmoc-TyrOH (Example 3), and Boc-Asp(OtBu)-OH according to Table 1 (coupling Steps 3–4 followed by Fmoc removal Steps 16–20) to provide Boc-Asp(OtBu)-Tyr-Met-DAla-Trp-Met-Asp(OtBu)-Phe-OCH$_2$-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEE and Amberlite XAD-2, sequentially, according to Table 1 (Step 30) to give 140 mg of the ammonium salt of the title compound. Amino acid analysis following acid decomposition gave Asp 1.93 (2), Tyr 0.94 (1), Met 1.81 (2), Ala 0.97 (1), and Phe 0.95 (1). Infrared absorption spectrum showed a strong peak typical of a sulfuric acid ester at 1050 cm$^{-1}$. TLC R$_f$ 0.34.

EXAMPLE 70

H-Asp-Tyr(SO$_3$H)-Met-Gly-Trp-DMet-Asp-Phe-NH$_2$

H-Phe-OCH$_2$-Pam-resin (Example 11) was sequentially coupled with Fmoc-Asp(OtBu)-OH, Fmoc-DMet-OH, Fmoc-Trp-OH, Fmoc-Asp(OtBu)-OH according to Table 1 (coupling Steps 3–4 followed by Fmoc removal Steps 16–20) to provide Boc-Asp(OtBu)-Tyr-Met-Gly-Trp-DMet-Asp(OtBu)-Fhe-OCH$_2$-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE according to Table 1 (Step 30) to give 368 mg of the ammonium salt of the title compound. Amino acid analysis following acid decomposition gave Asp 1.90 (2), Tyr 0.99 (1), Met 1.97 (2), Gly 0.92 (1), and Phe 0.98 (1). Infrared absorption spectrum showed a strong peak typical of a sulfuric acid ester at 1050 cm$^{-1}$. TLC R$_f$0.31.

EXAMPLE 71

H-Asp-Tyr(SO$_3$H)-Met-Gly-Trp-MetO-Asp-Phe-NH$_2$

H-Phe-OCH$_2$-Pam-resin (Example 11)was sequentially coupled with Fmoc-Asp(OtBu)-OH, Fmoc-MetO-OH, Fmoc-Trp-OH, Fmoc-Gly-OH, Fmoc-Met-OH, Fmoc-Tyr-OH (Example 3), and Boc-Asp(OtBu)-OH according to Table 1 (coupling Steps 3–4 followed by Fmoc removal Steps 16–20) to provide Boc-Asp(OtBu)-Tyr-Met-Gly-Trp-MetO-Asp(OtBu)-Phe-OCH$_2$-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE according to Table 1 (Step 30) to give 126 mg of the ammonium salt of the title compound. Amino acid analysis following acid decomposition gave Asp 2.03 (2), Tyr 0.96 (1), Met 0.98 (1), Gly 1.10 (1), MetO 0.97 (1), and Phe 0.96 (1). Infrared absorption spectrum showed a strong peak typical of a sulfuric acid ester at 1050 cm$^{-1}$. TLC R$_f$0.29.

EXAMPLE 72

H-Asp-Tyr(SO$_3$H)-Met-Gly-Trp-Met-Asp-Phe(4-Me)-NH$_2$

H-Phe(4-Me)-OCH$_2$-Pam-resin {prepared in an analogous fashion as H-Phe-OCH$_2$-Pam-resin [Example 11, Boc-Phe-(4-oxymethylphenyl)acetic acid replaced with Boc-Phe(4-Me)-(4-oxymethylphenyl)acetic acid] from Boc-Phe(4-Me)-(4-oxymethylphenyl)acetic acid [Example 5, Boc-MePhe-OH replaced with Boc-Phe(4-Me)-OH]} was sequentially coupled with Fmoc-Asp(OtBu)-OH, Fmoc-Met-OH, Fmoc-Trp-OH, Fmoc-Gly-OH, Fmoc-Met-OH, Fmoc-Tyr(tBu)-OH, and Fmoc-Asp(OtBu)-OH according to Table 1 (coupling Steps 5–7 followed by Fmoc removal Steps 16–20) to provide Fmoc-Asp(OtBu)-Tyr(tBu)-Met-Gly-Trp-Met-Asp(OtBu)-Phe(4-Me)-OCH$_2$-Pam-resin which was deprotected, sulfated, deprotected, and cleaved from the resin according to Table 1 (Steps 10–15, Steps 21–25, Steps 16–20, and then Steps 26–29 with ammonia) to give the title compound which was chromatographically purified on Amberlite XAD-2, Trisacryl M DEAE and P-40 ODS-3, sequentially, according to Table 1 (Step 30) to give 420 mg of the ammonium salt of the title compound. Amino acid analysis following acid decomposition gave Asp 2.02 (2), Tyr 1.00 (1), Met 1.91 (2), Gly 1.06 (1), and Phe(4-Me) 1 12 (1). Infrared absorption spectrum showed a strong peak typical of a sulfuric acid ester at 1050 cm$^{-1}$. TLC R$_f$ 0.44.

EXAMPLE 73

H-Asp-Tyr(SO$_3$H)-Met-Gly-Trp-Met-Asp-Tyr-NH$_2$

H-Tyr(tBu)-OCH$_2$-Pam-resin (prepared in an analogous fashion as H-Phe-OCH$_2$-Pam-resin [Example 11, Boc-Phe-(4-oxymethylphenyl)acetic acid replaced with Fmoc-Tyr(tBu)-(4-oxymethylphenyl)acetic acid]from Fmoc-Tyr(tBu)-(4-oxymethylphenyl)acetic acid [Example 5, Boc-MePhe-OH replaced with Fmoc-Tyr(-tBu)-OH]} was sequentially coupled with Fmoc-Asp(OtBu)-OH, Fmoc-Met-OH, Fmoc-Trp-OH, Fmoc-Gly-O,, Fmoc-Met-OH, Fmoc-Tyr-OH (Example 3), and Boc-Asp(OtBu)-OH according to Table 1 (coupling Steps 5-7 followed by Fmoc removal Steps 16-20) to provide Boc-Asp(OtBu)-Tyr-Met-Gly-Trp-Met-Asp-(OtBu)-Tyr(tBu)-OCH$_2$-Pam-resin which was sulfated, deprotected, and cleaved from the resin according to Table 1 (Steps 21-25, Steps 10-15, and then Steps 26-29 with ammonia) to give the title compound which was chromatographically purified on Amberlite XAD-2, Trisacryl M DEAE and P-40 ODS-3, sequentially, according to Table 1 (Step 30) to give 42 mg of the ammonium salt of the title compound. Amino acid analysis following acid decomposition gave Asp 2.09 (2), Tyr 2.16 (2), Met 1.66 (2), and Gly 1.09 (1). Infrared absorption spectrum showed a strong peak typical of a sulfuric acid ester at 1050 cm$^{-1}$. TLC R$_f$ 0.29.

EXAMPLE 74

Hpp(SO$_3$H)-Met-Gly-Trp-Pro-Asp-Phe-NH$_2$

H-Phe-OCH$_2$-Pam-resin (Example 11) was sequentially coupled with Fmoc-Asp(OtBu)-OH, Fmoc-Pro-OH, Fmoc-Trp-OH, Fmoc-Gly-OH, and Fmoc-Met-OH, according to Table 1 (coupling Steps 5-7 followed by Fmoc removal Steps 16-20) to provide H-Met-Gly-Trp-Pro-Asp(OtBu)-Phe-OCH$_2$-Pam-resin which was coupled with Hpp-OSu in DMF according to Table 1 (Steps 8-9) to give Hpp-Met-Gly-Trp-Pro-Asp(OtBu)-Phe-OCH$_2$-Pam resin which was deprotected, sulfated, and cleaved from the resin according to Table 1 (Steps 10-15, Steps 21-25, and then Steps 26-29 with ammonia) to give the title compound which was chromatographically purified on Amberlite XAD-2, Trisacryl M DEAE, and P-40 ODS-3, sequentially, according to Table 1 (Step 30) to give 70 mg of the ammonium salt of the title compound. Amino acid analysis following acid decomposition gave Met 1.01 (1), Gly 1.04 (1), Pro 0.97 (1), Asp 1.04 (1), and Phe 0.94 (1). Infrared absorption spectrum showed a strong peak typical of a sulfuric acid ester at 1050 cm$^{-1}$. TLC R$_f$ 0.51.

EXAMPLE 75

Hpp(SO$_3$H)-Pro-Gly-Trp-Pro-Asp-Phe-NH$_2$

H-Phe-OCH$_2$-Pam-resin (Example 11) was sequentially coupled with Fmoc-Asp(OtBu)-OH, Fmoc-Pro-OH, Fmoc-Trp-OH, Fmoc-Gly-OH, and Fmoc-Pro-OH according to Table 1 (coupling Steps 5-7 followed by Fmoc removal Steps 16-20) to provide H-Pro-Gly-Trp-Pro-Asp(OtBu)-Phe-OCH$_2$-Pam-resin which was coupled with Hpp-OSu in DMF according to Table 1 (Steps 8-9) to give Hpp-Pro-Gly-Trp-Pro-Asp(OtBu)-Phe-OCH$_2$-Pam resin which was deprotected, sulfated, and cleaved from the resin according to Table 1 (Steps 10-15, Steps 21-25, and then Steps 26-29 with ammonia) to give the title compound which was chromatographically purified on Amberlite XAD-2, Trisacryl M DEAE, and P-40 ODS-3, sequentially, according to Table 1 (Step 30) to give 480 mg of the ammonium salt of the title compound. Amino acid analysis following acid decomposition gave pro 2.02 (2), Gly 1.05 (1), Asp 1.00 (1), and Phe 0.93 (1). Infrared absorption spectrum showed a strong peak typical of a sulfuric acid ester at 1050 cm$^{-1}$. TLC R$_f$ 0.44.

EXAMPLE 76

Suc-Tyr(SO$_3$° H)-Ahx-Gly-Trp-Ahx-Asp-MePhe-NH$_2$

H-MePhe-OCH-Pam-resin (Example 12) was sequentially coupled with Fmoc-Ahx-Asp(OtBu)-OH (Example 10, Fmoc-Met-OH replaced with Fmoc-Ahx-OH), Fmoc-Trp-OH, Fmoc-Gly-OH, Fmoc-Ahx-OH, and Fmoc-Tyr(tBu)-OH according to Table 1 (coupling Steps 5-7 followed by Fmoc removal Steps 16-20) to provide H-Tyr(tBu)-Ahx-Gly-Trp-Ahx-Asp(OtBu)-MePhe-OCH$_2$-Pam-resin which was coupled with succinic anhydride in DMF according to Table 1 (Steps 8-9) to give Suc-Tyr(tBu)-Ahx-Gly-Trp-Ahx-Asp(OtBu)-MePhe-OCH$_2$-Pam resin which was deprotected, sulfated, and cleaved from the resin according to Table 1 (Steps 10-15, Steps 21-25, and then Steps 26-29 with ammonia) to give the title compound which was chromatographically purified on Amberlite XAD-2, Trisacryl M DEAE, and P-40 ODS-3, sequentially, according to Table 1 (Step 30) to give 100 mg of the ammonium salt of the title compound. Amino acid analysis following acid decomposition gave Tyr 0.97 (1), Gly 1.00 (1), and Asp 1.00 (1). Infrared absorption spectrum showed a strong peak typical of a sulfuric acid ester at 1050 cm$^{-1}$. TLC R$_f$ 0.46.

EXAMPLE 77 iBuOCO-Tyr(SO$_3$H)-Ahx-Gly-Trp-Ahx-Asp-MePhe-NH$_2$

H-MePhe-OCH$_2$-Pam-resin (Example 12) was sequentially coupled with Fmoc-Ahx-Asp(OtBu)-OH (Example 10, Fmoc-Met-OH replaced with Fmoc-Ahx-OH), Fmoc-Trp-OH, Fmoc-Gly-OH, Fmoc- Ahx-OH, and Fmoc-Tyr(tBu)-OH according to Table 1 (coupling Steps 5-7 followed by Fmoc removal Steps 16-20) to provide H-Tyr(tBu)-Ahx-Gly-Trp-Ahx-Asp(OtBu)-MePhe-OCH$_2$-Pam-resin which was coupled with iBuOCO-OSu (Example 1) in DMF according to Table 1 (Steps 8-9) to give iBuOCO-Tyr(tBu)-Ahx-Gly-Trp-Ahx-Asp(OtBu)-MePhe-OCH$_2$-Pam resin which was deprotected, sulfated, and cleaved from the resin according to Table 1 (Steps 10-15, Steps 21-25, and then Steps 26-29 with ammonia) to give the title compound which was chromatographically purified on Amberlite XAD-2 and P-40 ODS-3, sequentially, according to Table 1 (Step 30) to give 290 mg of the ammonium salt of the title compound. Infrared absorption spectrum showed a strong peak typical of a sulfuric acid ester at 1050 cm$^{-1}$. TLC R$_f$ 0.54.

EXAMPLE 78

Hpp(SO$_3$sH)-Ahx-Gly-Trp-Ahx-Asp-MePhe-NH$_2$

H-MePhe-OCH$_2$-Pam-resin (Example 12) was sequentially coupled with Fmoc-Ahx-Asp(OtBu)-OH (Example 10, Fmoc-Met-OH replaced with Fmoc-Ahx-OH), Fmoc-Trp-OH, Fmoc-Gly-OH, and Fmoc-Ahx-OH according to Table 1 (coupling Steps .5–7. followed by Fmoc removal Steps 16–20) to provide H-Ahx-Gly-Trp-Ahx-Asp(OtBu)-MePhe-OCH$_2$-Pam-resin which was coupled with Hpp-OSu in DMF according to Table 1 (Steps 8–9) to give Hpp-Ahx-Gly-Trp-Ahx-Asp(OtBu)-MePhe-OCH$_2$-Pam resin which was deprotected, sulfated, and cleaved from the resin according to Table 1 (Steps 10–15, Steps 21–25, and then Steps 26–29 with ammonia) to give the title compound was chromatographically purified on Amberlite XAD-2, Trisacryl M DEAE, and P-40 ODS-3, sequentially, according to Table 1 (Step 30) to give 91 mg of the ammonium salt of the title compound. Amino acid analysis following acid decomposition gave Ahx 1.92 (2), Gly 1.03 (1), and Asp 1.05 (1). Infrared absorption spectrum showed a strong peak typical of a sulfuric acid ester at 1050 cm$^{-1}$. TLC R$_f$0.40.

EXAMPLE 79 iBuOCO-Tyr(SO$_3$H)-Ahx-Gly-Trp-Ahx-Asp-Phe-NH$_2$

H-Phe-OCH$_2$-Pam-resin (Example 11) was sequentially coupled with Fmoc-Asp(OtBu)-OH, Fmoc-Ahx-OH, Fmoc-Trp-OH, Fmoc-GlyOH, Fmoc-Ahx-OH, and Fmoc-Tyr(tBu)-OH according to Table 1 (coupling Steps 5–7 followed by Fmoc removal Steps 16–20) to provide H-Tyr(tBu)-Ahx-Gly-Trp-Ahx-Asp(OtBu)-Phe-OCH$_2$-Pam-resin which was coupled with iBuOCO-OSu (Example 1) in DMF according to Table 1 (Steps 8–9) to give iBuOCO-Tyr-(tBu)-Ahx-Gly-Trp-Ahx-Asp(OtBu)-Phe-OCH$_2$-Pam resin which was deprotected, sulfated, and cleaved from the resin according to Table 1 (Steps 10–15, Steps 21–25, and then Stps 26–29 with ammonia) to give the title compound which was chromatographically purified on Amberlite XAD-2 and P-40 ODS-3, sequentially, according to Table 1 (Step 30) to give 800 mg of the ammonium salt of the title compound. Amino acid analysis following acid decomposition gave Tyr 0.90 (1), Ahx 1.84 (2), Gly 1.12 (1), Asp 1.12 (1), and Phe 0.92 (1). Infrared absorption spectrum showed a strong peak typical of a sulfuric acid ester at 1050 cm$^{-1}$. TLC R$_f$0.58.

EXAMpLE 80

Hpp(SO$_3$H)-Ahx-Gly-Trp-Ahx-Asp-Phe-NH$_2$

H-Phe-OCH$_2$-Pam-resin (Example 11) was sequentially coupled with Fmoc-Asp(OtBu)-OH, Fmoc-Ahx-OH, Fmoc-Trp-OH, Fmoc-Gly-OH, and Fmoc-Ahx-OH according to Table 1 (coupling Steps 5–7 followed by Fmoc removal Steps 16–20) to provide H-Ahx-Gly-Trp-Ahx-Asp(OtBu)-Phe-OCH$_2$-Pam-resin which was coupled with Hpp-OSu in DMF according to Table 1 (Steps 8–9) to give Hpp-Ahx-Gly-Trp-Ahx-Asp(OtBu)-Phe-OCH$_2$-Pam-resin which was deprotected, sulfated, and cleaved from the resin according to Table 1 (Steps 10–15, Steps 21–25, and then Steps 26–29 with ammonia) to give the title compound which was chromatographically purified on Amberlite XAD-2, and P-40 ODS-3, sequentially, according to Table 1 (Step 30) to give 450 mg of the ammonium salt of the title compound. Amino acid analysis following acid decomposition gave Ahx 1.92 (2), Gly 1.01 (1), Asp 1.10 (1), and Phe 0.97 (1). Infrared absorption spectrum showed a strong peak typical of a sulfuric acid ester at 1050 cm$^{-1}$. TLC R$_f$0.47.

EXAMPLE 81

Suc-Tyr(SO$_3$H)-Met-DAla-Trp-Met-Asp-Phe-NH$_2$

The title compound has previously been prepared (Petides 1984, 373–378 (1984)). H-Phe-OCH$_2$-Pam-resin (Example 11) was sequentially coupled with Fmoc-Met-Asp(OtBu)-OH (Example 10), Fmoc-Trp-OH, Fmoc-DAla-OH, Fmoc-Met-OH, and Fmoc-Tyr-(tBu)-OH according to Table 1 (coupling Steps 3–4 followed by Fmoc removal Steps 16–20) to provide H-Tyr-(tBu)-Met-DAla-Trp-Met-Asp(OtBu)-Phe-OCH$_2$-Pam-resin which was coupled with succinic anhydride in DMF according to Table1 (Steps 8–9) to give Suc-Tyr(tBu)-Met-DAla-Trp-Met-Asp(OtBu)-Phe-OCH$_2$-Pam-resin which was deprotected, sulfated, and cleaved from the resin according to Table 1 (Steps 10–15, Steps 21–25, and then Steps 26–29 with ammonia) to give the title compound which was chromatographically purified on Trisacryl M DEAE and P-40 ODS-3, sequentially, according to Table 1 (Step 30) to give 110 mg of the ammonium salt of the title compound. Amino acid analysis following acid decomposition gave Tyr 1.02 (1), Met 1.93 (2), Ala 1.00 (1), Asp 1.05 (I), and Phe 1.01 (1). Infrared absorption spectrum showed a strong peak typical of a sulfuric acid ester at 1050 cm$^{-1}$. TLC R$_f$ 0.38.

EXAMPLE 82

For-Tyr(SO$_3$H)-Ile-Gly-Trp-Ile-Asp-Phe-NH$_2$

H-Phe-OCH$_2$-Pam-resin (Example 11) was sequentially coupled with Fmoc-Ile-Asp(OtBu)-OH (Example 10, Fmoc-Met-OH replaced with Fmoc-Ile-OH), Fmoc-Trp-OH, Fmoc-Gly-OH, and Fmoc-Ile-OH according to Table 1 (coupling Steps 5–7 followed by Fmoc removal Steps 16–20) to provide H-Ile-Gly-Trp-Ile-Asp(OtBu)-Phe-OCH$_2$-Pam-resin which was deprotected according to Table 1 (Steps 10–15) to provide H-Ile-Gly-Trp-Ile-Asp-Phe-OCH$_2$-Pam-resin which was coupled with For-Tyr-OH according to Table 1 (Steps 3–4) to give For-Tyr-H Ile-Gly-Trp-Ile-Asp-Phe-OCH$_2$-Pam-resin which was sulfated and cleaved from the resin according to Table 1 (Steps 21–25 and then Steps 26–29 with ammonia) to give the title compound which was chromatographically purified on Amberlite XAD-2 and P-40 ODS-3, sequentially, according to Table 1 (Step 30) to give 200 mg of the ammonium salt of the title compound. Amino acid analysis following acid decomposition gave Tyr 0.98 (1), Ile 1.94 (2), Gly 1.00 (1), Asp 1.09 (1), and Phe 0.98 (1). Infrared absorption spectrum showed a strong peak typical of a sulfuric acid ester at 1050 cm$^{-1}$. TLC R$_f$0.59.

EXAMPLE 83

Suc-Tyr(SO$_3$H)-Ile-Gly-Trp-Ile-Asp-Phe-NH$_2$

H-Phe-OCH$_2$-Pam-resin (Example 11) was sequentially coupled with Fmoc-Ile-Asp(OtBu)-OH (Example 10, Fmoc-Met-OH replaced with Fmoc-Ile-OH), Fmoc-Trp-OH, Fmoc-Gly-OH, Fmoc-Ile-OH, and Fmoc-Tyr(tBu)-OH according to Table 1 (coupling Steps 5–7 followed by Fmoc removal Steps 16–20) to provide H-Tyr(tBu)-Ile-Gly-Trp-Ile-Asp(OtBu)-Phe-OCH$_2$-Pam-resin which was coupled with succinic anhydride in DMF according to Table (Steps 8–9) to give Suc-Tyr(tBu)-Ile-Gly-Trp-Ile-Asp(OtBu)-Phe-OCH$_2$-Pam-resin which was deprotected, sulfated, and cleaved from the resin according to Table 1 (Steps 10–15, Steps 21–25, and then Steps 26–29 with ammonia) to give the title compound which was chromatographically purified on Amberlite XAD-2 and P-40 ODS-3, sequentially, according to Table 1 (Step 30) to give 300 mg of the ammonium salt of the title compound. Amino acid analysis following acid decomposition gave Tyr 1.00 (1), Ile 2.07 (2), Gly 0.97 (1), Asp 0.97 (1), and Phe 0.99 (1). Infrared absorption spectrum showed a strong peak typical of a sulfuric acid ester at 1050 cm$^{-1}$. TLC R$_f$ 0.42.

EXAMPLE 84 iBuOCO-Tyr(SO$_3$H)-Ile-Gly-Trp-Ile-Asp-Phe-NH$_2$

H-Phe-OCH$_2$-Pam-resin (Example 11) was sequentially coupled with Fmoc-Ile-Asp(OtBu)-OH (Example 10, Fmoc-Met-OH replaced with Fmoc-Ile-OH), Fmoc-Trp-OH, Fmoc-Gly-OH, Fmoc-Ile-OH, and Fmoc-Tyr(tBu)-OH according to Table 1 (coupling Steps 5–7 followed by Fmoc removal Steps 16–20) to provide H-Tyr(tBu)-Ile-Gly-Trp-Ile-Asp(OtBu)-Phe-OCH$_2$-Pam-resin which was coupled with iBuOCO-OSu (Example 1) in DMF according to Table 1 (Steps 8–9) to give iBuOCO-Tyr(tBu)-Ile-Gly-Trp-Ile-Asp(OtBu)-Phe-OCH$_2$-Pam-resin which was deprotected, sulfated, and cleaved from the resin according to Table 1 (Steps 10–15, Steps 21–25, and then Steps 26–29 with ammonia) to give the title compound which was chromatographically purified on Amberlite XAD-2 and P-40 ODS-3, sequentially, according to Table 1 (Step 30) to give 390 mg of the ammonium salt of the title compound. Amino acid analysis following acid decomposition gave Tyr 1.07 (1), Ile 2.21 (2), Gly 1.04 (1), Asp 1.00 (1), and Phe 1.03 (1). Infrared absorption spectrum showed a strong peak typical of a sulfuric acid ester at 1050 cm$^{-1}$. TLC R$_f$ 0.61.

EXAMPLE 85

Hpp(SO$_3$H)-Ile-Gly-Trp-Ile-Asp-Phe-NH$_2$

H-Phe-OCH$_2$-Pam-resin (Example 11) was sequentially coupled with Fmoc-Ile-Asp(OtBu)-OH (Example 10, Fmoc-Met-OH replaced with Fmoc-Ile-OH), Fmoc-Trp-OH, Fmoc-Gly-OH, and Fmoc-Ile-OH according to Table 1 (coupling Steps 5–7 followed by Fmoc removal Steps 16–20) to provide H-Ile-Gly-Trp-Ile-Asp(OtBu)-Phe-OCH$_2$-Pam-resin which was coupled with Hpp-OSu in DMF according to Table I (Steps 8–9) to give Hpp-Ile-Gly-Trp-Ile-Asp(OtBu)-Phe-OCH$_2$-Pam-resin which was deprotected, sulfated, and cleaved from the resin according to Table 1 (Steps 10–15, Steps 21–25, and then Steps 26–29 with ammonia) to give the title compound which was chromatographically purified on Amberlite XAD-2 and P40 ODS-3, sequentially, according to Table 1 (Step 30) to give 280 mg of the ammonium salt of the title compound. Amino acid analysis following acid decomposition gave Ile 2.04 (2), Gly 0.99 (1), Asp 0.98 (1), and Phe 0.99 (1).

Infrared absorption spectrum showed a strong peak typical of a sulfuric acid ester at 1050 cm$^{-1}$. TLC R$_f$ 0.52.

EXAMPLE 86

Suc-Tyr(SO$_3$H)-Met-Gly-Trp-Met-Asp-MePhe-NH$_2$

The title compound has previously been prepared (N. Yanaihara, et al., in Peptides 1984: Proceedings of the 18th European Peptide Symposium. U. Ragnarsson, Ed., Almqvist and Wiksell International, Publisher, Stockholm, Sweden, 1985, pp 373–378). H-MePhe-OCH$_2$-Pam-resin (Example 12) was sequentially coupled with Fmoc-Met-Asp(OtBu)-OH (Example 10) Fmoc-Trp-OH, Fmoc-Gly-OH, Fmoc-Met-OH, and Fmoc-Tyr(tBu)-OH according to Table 1 (coupling Steps 5–7 followed by Fmoc removal Steps 16–20) to provide H-Tyr(tBu)-Met-Gly-Trp-Met-Asp(OtBu)-MePhe-OCH$_2$-Pam-resin which was coupled with succinic anhydride in DMF according to Table 1 (Steps 8–9) to give Suc-Tyr(tBu)-Met-Gly-Trp-Met-Asp(OtBu)-MePhe-OCH$_2$-Pam-resin which was deprotected, sulfated, and cleaved from the resin according to Table 1 (Steps 10–15, Steps 21–25, and then Steps 26–29 with ammonia) to give the title compound which was chromatographically purified on Amberlite XAD-2 and P-40 ODS-3, sequentially, according to Table 1 (Step 30) to give 170 mg of the ammonium salt of the title compound. Amino acid analysis following acid decomposition gave Tyr 1.02 (1), Met 1.94 (2), Gly 1.09 (1), Asp 1.00 (1), and MePhe 1.02 (1). Infrared absorption spectrum showed a strong peak typical of a sulfuric acid ester at 1050 cm$^{-1}$. TLC R$_f$ 0.58.

EXAMPLE 87

H-DAsp-Tyr(SO$_3$H)-Ile-Gly-Trp-Ile-Asp-MePhe-NH$_2$

H-MePhe-OCH$_2$-Pam-resin (Example 12) was sequentially coupled with Fmoc-Ile-Asp(OtBu)-OH (Example 10, Fmoc-Met-OH replaced with Fmoc-Ile-OH), Fmoc-Trp-OH, Fmoc-Gly-OH, Fmoc-Ile-OH, Fmoc-Tyr(tBu)-OH, and Fmoc-DAsp(OtBu)-OH according to Table 1 (coupling Steps 5–7 followed by Fmoc removal Steps 16–20) to provide Fmoc-DAsp(OtBu)-Tyr(tBu)-Ile-Gly-Trp-Ile-Asp(OtBu)-MePhe-OCH$_2$-Pam-resin which was deprotected, sulfated, deprotected, and cleaved from the resin according to Table 1 (Steps 10–15, Steps 21–25, Steps 16–20, and then Steps 26–29 with ammonia) to give the title compound which was chromatographically purified on Amberlite XAD-2 and P-40 ODS-3, sequentially, according to Table 1 (Step 30) to give 30 mg of the ammonium salt of the title compound. Amino acid analysis following acid decomposition gave Asp 1.96 (2), Tyr 0.97 (1), Ile 1.92 (2), Gly 0.98 (1), and MePhe 1.18 (1). Infrared absorption spectrum showed a strong peak typical of a sulfuric acid ester at 1050 cm$^{-1}$. TLC R$_f$ 0.36.

EXAMPLE 88

For-Tyr(SO$_3$H)-Ile-Gly-Trp-Ile-Asp-MePhe-NH$_2$

H-MePhe-OCH$_2$*-Pam-resin (Example 12) was sequentially coupled with Fmoc-Ile-Asp(OtBu)-OH (Example 10, Fmoc-Met-OH replaced with Fmoc-Ile-OH), Fmoc-Trp-OH, Fmoc-Gly-OH and Fmoc-Ile-OH according to Table (coupling Steps 5–7 followed by Fmoc removal Steps 16–20) to provide H-Ile-Gly-Trp-Ile-Asp-MePhe-OCH$_2$-Pam-resin which was deprotected according to Table 1 (Steps 10–15) to provide H-Ile-Gly-Trp-Ile-Asp-MePhe-OCH$_2$-Pam-resin which was coupled with For-Tyr-OH according to Table 1 (coupling Steps 3-4) to give For-Tyr-Ile-Gly-Trp-Ile-Asp-MePhe-OCH$_2$-Pam-resin which was sulfated and cleaved from the resin according to Table 1 (Steps 21-25 and then Steps 26-29 with ammonia) to give the title compound which was chromatographically purified on Amberlite XAD-2 and P-40 ODS-3, sequentially, according to Table 1 (Step 30) to give 90 mg of the ammonium salt of the title compound. Amino acid analysis following acid decomposition gave Tyr 1.04 (1), Ile 1.95 (2), Gly 0.97 (1), Asp 1.01 (1), and MePhe 1.03 (1). Infrared absorption spectrum showed a strong peak typical of a sulfuric acid ester at 1050 cm$^{-1}$. TLC R$_f$0.60.

EXAMPLE 89

Suc-Tyr(SO$_3$H)-Ile-Gly-Trp-Ile-Asp-,MePhe-NH$_2$

H-MePhe-OCH$_2$-Pam-resin (Example 12) was sequentially coupled with Fmoc-Ile-Asp(OtBu)-OH (Example 10, Fmoc-Met-OH replaced with Fmoc-Ile-OH), Fmoc-Trp-OH, Fmoc-Gly-OH, Fmoc-Ile-OH, and Fmoc-Tyr(tBu)-OH according to Table 1 (coupling Steps 5-7 followed by Fmoc removal Steps 16-20) to give H-Tyr(tBu)-Ile-Gly-Trp-Ile-Asp(OtBu)-MePhe-OCH$_2$-Pam-resin which was coupled with succinic anhydride in DMF according to Table 1 (Steps 8-9) to give Suc-Tyr(tBu)-Ile-Gly-Trp-Ile-Asp(OtBu)-MePhe-OCH$_2$-Pam-resin which was deprotected, sulfated, and cleaved from the resin according to Table 1 (Steps 10-15, Steps 21-25, and then Steps 26-29 with ammonia) to give the title compound which was chromatographically purified on Amberlite XAD-2 and P-40 ODS-3, sequentially, according to Table 1 (Step 30) to give 130 mg of the ammonium salt of the title compound. Amino acid analysis following acid decomposition gave Tyr 0.94 (1), Ile 1.92 (2), Gly 1.04 (1), Asp 1.09 (1), and MePhe 1.00 (1). Infrared absorption spectrum showed a strong peak typical of a sulfuric acid ester at 1050 cm$^{-1}$. TLC R$_f$0.37.

EXAMPLE 90 iBuOCO-Tyr(SO$_3$sH)-Ile-Gly-Trp-Ile-Asp-MePhe-NH$_2$

H-MePhe-OCH$_2$-Pam-resin (Example 12) was sequentially coupled with Fmoc-Ile-Asp(OtBu)-OH (Example 10, Fmoc-Met-OH replaced with Fmoc-Ile-OH), Fmoc-Trp-OH, Fmoc-Gly-OH, Fmoc-Ile-OH, and Fmoc-Tyr(tBu)-OH according to Table 1 (coupling Steps 5-7 followed by Fmoc removal Steps 16-20) to provide H-Tyr(tBu)-Ile-Gly-Trp-Ile-Asp(OtBu)-MePhe-OCH$_2$-Pam-resin which was coupled with iBuOCO-OSu (Example in DMF according to Table 1 (Steps 8-9) to give iBuOCO-Tyr(tBu)-Ile-Gly-Trp-Ile-Asp(OtBu)-MePhe-OCH$_2$-Pam-resin which was deprotected, sulfated, and cleaved from the resin according to Table 1 (Steps 10-15, Steps 21-25, and then Steps 26-29 with ammonia) to give the title compound which was chromatographically purified on Amberlite XAD-2 and P-40 ODS-3, sequentially, according to Table 1 (Step 30) to give 50 mg of the ammonium salt of the title compound. Amino acid analysis following acid decomposition gave Tyr 1.00 (1), Ile 1.92 (2), Gly 1.02 (1), Asp 1.03 (1), and MePhe 1.03 (1). Infrared absorption spectrum showed a strong peak typical of a sulfuric acid ester at 1050 cm$^{-1}$. TLC R$_f$0.74.

EXAMPLE 91

H-Asp-DTyr(SO$_3$H)-Ile-Gly-Trp-Ile-Asp-MePhe-NH$_2$

H-MePhe-OCH$_2$-Pam-resin (Example 12) was sequentially coupled with Fmoc-Ile-Asp(OtBu)-OH (Example 10, Fmoc-Met-OH replaced with Fmoc-Ile-OH), Fmoc-Trp-OH, Fmoc-Gly-OH, Fmoc-Ile-OH, Fmoc-DTyr(tBu)-OH, and Fmoc-Asp(OtBu)-OH according to Table 1 (coupling Steps 5-7 followed by Fmoc removal Steps 16-20) to provide Fmoc-Asp(OtBu)-DTyr(tBu)-Ile-Gly- Trp-Ile-Asp(OtBu)-MePhe-OCH$_2$-Pam-resin which was deprotected, sulfated, deprotected, and cleaved from the resin according to Table I (Steps 10-15, Steps 21-25, Steps 16-20, and then Steps 26-29 with ammonia) to give the title compound which was chromatographically purified on Amberlite XAD-2 and P-40 ODS-3, sequentially, according to Table 1 (Step 30) to give 200 mg of the ammonium salt of the title compound. Amino acid analysis following acid decomposition gave Asp 2.08 (2), Tyr 1.01 (1), Ile 1.94 (2), Gly 0.98 (1), and MePhe 0.99 (1). Infrared absorption spectrum showed a strong peak typical of a sulfuric acid ester at 1050 cm$^{-1}$. TLC R$_f$0.38.

EXAMPLE 92

Hpp(SO$_3$H)-Ile-Gly-Trp-Ile-Asp-MePhe-NH$_2$

H-MePhe-OCH$_2$-Pam-resin (Example 12) was sequentially coupled with Fmoc-Ile-Asp(OtBu)-OH (Example 10, Fmoc-Met-OH replaced with Fmoc-Ile-OH), Fmoc-Trp-OH, Fmoc-Gly-OH, and Fmoc-Ile-OH according to Table 1 (coupling Steps 5-7 followed by Fmoc removal Steps 16-20) to provide H-Ile-Gly-Trp-Ile-Asp(OtBu)-MePhe-OCH$_2$-Pam-resin which was coupled with Hpp-OSu according to Table 1 (coupling Steps 8-9) to give Hpp-Ile-Gly-Trp-Ile-Asp(OtBu)-MePhe-OCH$_2$-Pam-resin which was deprotected, sulfated, and cleaved from the resin according to Table 1 (Steps 10-15, Steps 21-25, and then Steps 26-29 with ammonia) to give the title compound 30 which was chromatographically purified on Amberlite XAD-2 and P-40 ODS-3, sequentially, according to Table 1 (Step 30) to give 70 mg of the ammonium salt of the title compound. Amino acid analysis following acid decomposition gave Ile 1.94 (2), Gly 1.01 (1), Asp 1.02 (1), and MePhe 1.04 (1). Infrared absorption spectrum showed a strong peak typical of a sulfuric acid ester at 1050 cm$^{-1}$. TLC R$_f$0.63.

EXAMPLE 93

H-DAsp-Tyr(SO$_3$H)-Ile-Gly-Trp-Ile-Asp-Phe-NH$_2$

H-Phe-OCH$_2$-Pam-resin (Example 11) was sequentially coupled with Fmoc-Ile-Asp(OtBu)-OH (Example 10, Fmoc-Met-OH replaced with Fmoc-Ile-OH), Fmoc-Trp-OH, Fmoc-Gly-OH, Fmoc-Ile-OH, Fmoc-Tyr(tBu)-OH and Fmoc-DAsp(OtBu)-OH according to Table 1 (coupling Steps 5-7 followed by Fmoc removal Steps 16-20) to provide Fmoc-DAsp(OtBu)-Tyr(tBu)-Ile-Gly-Trp-Ile-Asp(OtBu)-Phe-OCH$_2$-Pam-resin which was deprotected, sulfated, deprotected, and cleaved from the resin according to Table 1 (Steps 10-15, Steps 21-25, Steps 16-20, and then Steps 26-29 with ammonia) to give the title compound which was chromatographically purified on Amberlite XAD-2 and P-40 ODS-3, sequentially, according to Table 1 (Step 30) to give 270 mg of the ammonium salt of the title compound. Amino acid analysis following acid decomposition gave Tyr 1.00 (1), Ile 1.94 (2), Gly 0.98 (1), Asp 2.14 (2), and Phe 0.94 (1). Infrared absorption spectrum showed a strong peak typical of a sulfuric acid ester at 1050 cm$^{-1}$. TLC R$_f$0.41.

EXAMPLE 94

H-Asp-Tyr(SO$_3$H)-Met-Pro-Trp-Met-Asp-MePhe-NH$_2$

H-Mephe-OCH$_2$-Pam-resin (Example 12) was sequentially coupled with Fmoc-Met-Asp(OtBu)-OH (Example 10), Fmoc-TrpOH, Fmoc-Pro-OH, Fmoc-Met-OH, Fmoc-Tyr-OH, and Boc-Asp-(OtBu)-OH according to Table 1 (coupling Steps 3–4 followed by Fmoc removal Steps 16–20) to provide Boc-Asp(OtBu)-Tyr-Met-Pro-Trp-Met-Asp(Otuu)-MePhe-OCH$_2$-Pam-resin which was sulfated, deprotected, and cleaved from the resin according to Table 1 (Steps 21–25, Steps 10–15, and then Steps 26–29 with ammonia) to give the title compound which was chromatographically purified on Trisacryl M DEAE and P-40 ODS-3, sequentially, according to Table 1 (Step 30) to give 83 mg of the ammonium salt of the title compound. Amino acid analysis following acid decomposition gave Asp 1.99 (2), Tyr 1.00 (1), Met 1.91 (2), and Pro 1.11 (1). Infrared absorption spectrum showed a strong peak typical of a sulfuric acid ester at 1050 cm$^{-1}$. TLC R$_f$0.34.

EXAMPLE 95 iBuOCO-Tyr(SO$_3$sH)-Met-DAla-Trp-Met-Asp-MePhe-NH$_2$

H-MePhe-OCH$_2$-Pam-resin (Example 12) was sequentially coupled with Fmoc-Met-Asp(OtBu)-OH (Example 10), Fmoc-Trp-OH, Fmoc-DAla-OH, Fmoc-Met-OH, and Fmoc-Tyr(tBu)-OH according to Table 1 (coupling Steps 5–7 followed by Fmoc removal Steps 16–20) to provide H-Tyr(tBu)-Met-DAla-Trp-Met-Asp-(OtBu)-MePhe-OCH$_2$-Pam-resin which was coupled with iBuOCO-OSu (Example 1) in DMF according to Table 1 (Steps 8–9) to give iBuOCO-Tyr(tBu)-Met-DAla-Trp-Met-Asp(OtBu)-MePhe-OCH$_2$-Pam-resin which was deprotected, sulfated, and cleaved from the resin according to Table 1 (Steps 10–15, Steps 21–25, and then Steps 26–29 with ammonia) to give the title compound which was chromatographically purified on Amberlite XAD-2 and P-40 ODS-3, sequentially, according to Table 1 (Step 30) to give 80 mg of the ammonium salt of the title compound. Amino acid analysis following acid decomposition gave Tyr 1.02 (1), Met 1.84 (2), Ala 1.05 (1), Asp 1.05 (1), and MePhe 1.04 (1). Infrared absorption spectrum showed a strong peak typical of a sulfuric acid ester at 1050 cm$^{-1}$. TLC R$_f$0.95.

EXAMPLE 96

H-βAsp-Tyr(SO$_3$H)-Ile-Gly-Trp-Ile-Asp-MePhe-NH$_2$

H-MePhe-OCH$_2$-Pam-resin (Example 12) was sequentially coupled with Fmoc-Ile-Asp(OtBu)-OH (Example 10, Fmoc-Met-OH replaced with Fmoc-Ile-OH), Fmoc-Trp-OH, Fmoc-Gly-OH, Fmoc-Ile-OH, Fmoc-Tyr(tBu)-OH and Boc-βAsp(OtBu)-OH according to Table 1 (coupling Steps 5–7 followed by Fmoc removal Steps 16–20) to provide Boc-βAsp(OtBu)-Tyr(tBu)-Ile-Gly-Trp-Ile-Asp(OtBu)-MePhe-OCH$_2$-Pam-resin which was deprotected according to Table 1 (Steps 10–15) and coupled with Fmoc-OSu according to Table 1 (Steps 8–9) to give Fmoc-βAsp-Tyr-Ile-Gly-Trp-Ile-Asp-MePhe-OCH$_2$-Pam-resin which was sulfated, deprotected, and cleaved from the resin according to Table 1 (Steps 21–25, Steps 16–20, and then Steps 26–29 with ammonia) to give the title compound which was chromatographically purified on Amberlite XAD-2 and P-40 ODS-3, sequentially, according to Table 1 (Step 30) to give 100 mg of the ammonium salt of the title compound. Amino acid analysis following acid decomposition gave Asp 2.01 (2), Tyr 1.00 (1), Ile 1.98 (2), Gly 1.02 (1), and MePhe 0.95 (1). Infrared absorption spectrum showed a strong peak typical of a sulfuric acid ester at 1050 cm$^{-1}$. TLC R$_f$0.47.

EXAMPLE 97

For-Tyr(SO$_3$H)-Ile-Gly-Trp-Ahx-Asp-MePhe-NH$_2$

H-MePhe-OCH$_2$-Pam-resin (Example 12) was sequentially coupled with Fmoc-Ahx-Asp(OtBu)-OH (Example 10, Fmoc-Met-OH replaced with Fmoc-Ahx-OH), Fmoc-Trp-OH, Fmoc-Gly-OH, and Fmoc-Ile-OH according to Table 1 (coupling Steps 5–7 followed by Fmoc removal Steps 16–20) to provide H-Ile-Gly-Trp-Ahx-Asp(OtBu)-MePhe-OCH$_2$-Pam-resin which was deprotected according to Table 1 (Steps 10–15) to provide H-Ile-Gly-Trp-Ahx-Asp-MePhe-OCH$_2$-Pam-resin which was coupled with For-Tyr-OH according to Table 1 (Steps 3–4) to give For-Ile-Gly-Trp-Ahx-Asp-MePhe-OCH$_2$-Pam-resin which was sulfated and cleaved from the resin according to Table 1 (Steps 21–25 and then Steps 26–29 with ammonia) to give the title compound which was chromatographically purified on Amberlite XAD-2 and P-40 ODS-3, sequentially, according to Table 1 (Step 30) to give 60 mg of the ammonium salt of the title compound. Amino acid analysis following acid decomposition gave Tyr 0.99 (1), Ile 1.01 (1), Ahx 1.05 (1), Gly 1.04 (1), Asp 1.05 (1), and MePhe 0.86 (1). Infrared absorption spectrum showed a strong peak typical of a sulfuric acid ester at 1050 cm$^{-1}$. TLC R$_f$0.51.

EXAMPLE 98

Suc-Tyr(SO$_3$H)-Ile-Gly-Trp-Ahx-Asp-MePhe-NH$_2$

H-MePhe-OCH$_2$-Pam-resin (Example 12) was sequentially coupled with Fmoc-Ahx-Asp(OtBu)-OH (Example 10, Fmoc-Met-OH replaced with Fmoc-Ahx-OH), Fmoc-Trp-OH, Fmoc-Gly-OH, Fmoc-Ile-OH, and Fmoc-Tyr(tBu)-OH according to Table 1 (coupling Steps 5–7 followed by Fmoc removal Steps 16–20) to provide H-Tyr(tBu)-Ile-Gly-Trp-Ahx-Asp(OtBu)-MePhe-OCH$_2$-Pam-resin which was coupled with succinic anhydride in DMF according to Table 1 (Steps 8–9) to give Suc-Tyr(tBu)-Ile-Gly-Trp-Ahx-Asp(OtBu)-MePhe-OCH$_2$-Pam-resin which was deprotected, sulfated, and cleaved from the resin according to Table 1 (Steps 10–15, Steps 21–25, and then Steps 26–29 with ammonia) to give the title compound which was chromatographically purified on Amberlite XAD-2 and P-40 ODS-3, sequentially, according to Table 1 (Step 30) to give 130 mg of the ammonium salt of the title compound. Amino acid analysis following acid decomposition gave Tyr 0.99 (1), Ile 0.94 (1), Ahx 0.96 (1), Gly 1.02 (1), Asp 1.00 (1), and MePhe 1.09 (1). Infrared absorption spectrum showed a strong peak typical of a sulfuric acid ester at 1050 cm$^{-1}$. TLC R$_f$0.65.

EXAMPLE 99 iBuOCO-Tyr(SO3H)-Ile-Gly-Trp-Ahx-Asp-MePhe-NH2

H-MePhe-OCH2-Pam-resin (Example 12) was sequentially coupled with Fmoc-Ahx-Asp(OtBu)-OH (Example 10, Fmoc-Met-OH replaced with Fmoc-Ahx-OH), Fmoc-Trp-OH, Fmoc-Gly-OH, Fmoc-Ile-OH, and Fmoc-Tyr(tBu)-OH according to Table 1 (coupling Steps 5-7 followed by Fmoc removal Steps 16-20) to provide H-Tyr(tBu)-Ile-Gly-Trp-Ahx-Asp(OtBu)-MePhe-OCH2-Pam-resin which was coupled with iBuOCO-OSu (Example 1) in DMF according to Table 1 (Steps 8-9) to give iBuOCO-Tyr(tBu)- Ile-Gly-Trp-Ahx-Asp(OtBu)-MePhe-OCH2-Pam-resin which was deprotected, sulfated, and cleaved from the resin according to Table 1 (Steps 10-15, Steps 21-25, and then Steps 26-29 with ammonia) to give the title compound which was chromatographically purified on Amberlite XAD-2 and P-40 ODS-3, sequentially, according to Table 1 (Step 30) to give 140 mg of the ammonium salt of the title compound. Amino acid analysis following acid decomposition gave Tyr 1.05 (1), Ile 1.04 (1), Ahx 1.03 (1), Gly 1.06 (1), Asp 1.07 (1), and MePhe 0.76 (1). Infrared absorption spectrum showed a strong peak typical of a sulfuric acid ester at 1050 cm$^{-1}$. TLC $R_f$ 0.93.

EXAMPLE 100

Hpp(SO3sH)-Ile-Gly-Trp-Ahx-Asp-MePhe-NH2

H-MePhe-OCH2-Pam-resin (Example 12) was sequentially coupled with Fmoc-Ahx-Asp(OtBu)-OH (Example 10, Fmoc-Met-OH replaced with Fmoc-Ahx-OH), Fmoc-Trp-OH, Fmoc-Gly-OH, and Fmoc-Ile-OH according to Table 1 (coupling Steps 5-7 followed by Fmoc removal Steps 16-20) to provide H-Ile-Gly-Trp-Ahx-Asp(OtBu)-MePhe-OCH2-Pam-resin which was coupled with Hpp-OSu according to Table 1 (coupling Steps 8-9) to give Hpp-Ile-Gly-Trp-Ahx-Asp(OtBu)-MePhe-OCH2-Pam-resin which was deprotected, sulfated, and cleaved from the resin according to Table 1 (Steps 10-15, Steps 21-25, and then Steps 26-29 with ammonia) to give the title compound which was chromatographically purified on Amberlite XAD-2 and P-40 ODS-3, sequentially, according to Table 1 (Step 30) to give 30 mg of the ammonium salt of the title compound. Amino acid analysis following acid decomposition gave Ile 0.86 (1), Ahx 0.82 (1), Gly 1.16 (1), and Asp 1.17 (1). Infrared absorption spectrum showed a strong peak typical of a sulfuric acid ester at 1050 cm$^{-1}$. TLC $R_f$ 0.64.

What is claimed is:

1. A peptide of the formula

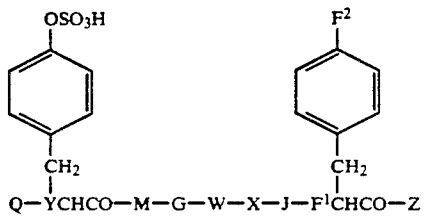

wherein

Q is H, H-Asp, H-βAsp, H-DAsp, H-MeAsp, For, Ac, Suc, desQ, or $R^1R^2$CHOCO;

Y is H, (S)—NH or (R)—$R^3$N, or (S)—$R^3$N;

M is Met, DMet, MeMet, MetO, Ahx, DAhx, MeAhx, Leu, MeLeu, Pro, Ile, MeIle, or Lys;

G is Gly, Pro or Sar,

W is Trp, MeTrp or Nal,

X is Met, MeMet, MetO, Ahx, MeAhx, Leu, MeLeu, Ile, MeIle, Pro, or Lys,

J is Asp, DAsp, MeAsp, or Asn, $F^1$ is (S)—NH, (S)—$R^4$N, or (R)-$R^4$N, $F^2$ is H, Cl, I, Br, F, NO, NH2, $R^5$, or OR$^6$,

Z is NH2, NHR$^7$ or NR$^7R^8$, $R^1$ and $R^2$ are independently H or lower alkyl, $R^3$, $R^4$, and $R^5$ are lower alkyl, $R^6$ is H or lower alkyl, and $R^7$ and $R^8$ are lower alkyl, and pharmaceutically acceptable salts thereof, provided that (1) Q is desQ when Y is H, (2) $F^2$ is not H if, in the same peptide, Q is H-Asp or Ac, Y is (S)—NH, M is either Met, MetO, Ahx or Leu, X is either Met, MetO, Ahx or Leu, G is Gly, DAla or Pro, W is Trp, J is Asp, F is (S)-NH, and Z is NH2, (3) $F^2$ is not H if, in the same peptide, Q is H, H-βAsp or For, Y is (S)-NH, M is Met, Ahx or Leu, G is Gly, W is Trp, X is Met, Ahx or Leu, J is Asp, $F^1$ is (S)—NH, and Z is NH2, (4) $F^2$ is not H if, in the same peptide, Y is H, M is Met, X is Met, G is Gly, W is Trp, J is Asp, $F^1$ is (S)—NH, and Z is NH2, and (5) $F^2$ is not H if, in the same peptide, Q is Suc, Y is (S)—NH, M is Met, X is Met, G is Gly or DAla, W is Trp, J is Asp, $F^1$ is (S)—NH or (S)—$R^4$N, and Z is NH2.

2. A peptide of claim 1 wherein

Q is H, H-Asp, H-βAsp, H-DAsp, For, Ac, Suc, desQ, or $R^1R^2$CHOCO;

Y is H, (S)—NH or (S)—$R^3$N;

M is Met, MeMet, Ahx, MeAhx, Leu, MeLeu, Ile, MeIle, or Pro;

G is Gly or DAla;

W is Trp;

X is Met, MeMet, Ahx, MeAhx, Leu, MeLeu, Ile, MeIle, or Pro;

J is Asp;

$F^1$ is (S)—NH or (S)—$R^4$N;

$F^2$ is H, Cl, NO2, NH2, $R^5$ or OR$^6$; and Z is NH2.

3. A peptide of claim 1 wherein M is Met, DMet, MetO, Ahx, DAhx, Leu, Pro, Ile or Lys and X is Met, MetO, Ahx, Leu, Ile, Pro or Lys.

4. A peptide of claim 1 that is
H-DAsp-Tyr(SO3H)-Met-Gly-Trp-Met-Asp-Phe-NH2.

5. A peptide of claim 1 that is
iBuOCO-Tyr(SO3H)-Met-Gly-Trp-Met-Asp-Phe.-NH2.

6. A peptide of claim 1 that is
H-Asp-Tyr(SO3H)-DMet-Gly-Trp-Met-Asp-Phe-NH2.

7. A peptide-of claim 1 that is
H-Asp-Tyr(SO3H)-DAhx-Gly-Trp-Met-Asp-Phe-NH2.

8. A peptide of claim 1 that is
H-Asp-Tyr(SO3H)-Met-Sar-Trp-Met-Asp-Phe-NH2.

9. A peptide of claim 1 that is
H-Asp-Tyr(SO3H)-Met-Gly-MeTrp-Met-Asp-Phe-NH2.

10. A peptide of claim 1 that is

11. A peptide of claim 1 that is H-Asp-Tyr(SO₃H)-Met-Gly-Trp-Met-DAsp-Phe-NH₂.

11. A peptide of claim 1 that is H-Asp-Tyr(SO₃H)-Met-Gly-Trp-Met-Asn-Phe-NH₂.

12. A peptide of claim 1 that is H-Asp-Tyr(SO₃*H)-Met-Gly-Trp-Met-Asp-MePhe-NH₂.

13. A peptide of claim 1 that is H-Asp-Tyr(SO₃sH)-Met-Gly-Trp-Met-Asp-MeTyr(Me)-NH₂.

14. A peptide of claim 1 that is H-Asp-Tyr(SO₃H)-Met-Gly-Trp-Met-Asp-Phe(4-NO₂)-NH₂.

15. A peptide of claim 1 that is H-Asp-Tyr(SO₃H)-Met-Gly-Trp-Met-Asp-Phe(4-Cl)-NH₂.

16. A peptide of claim 1 that is H-Asp-Tyr(SO₃H)-Met-Gly-Trp-Met-Asp-Phe(4-NH₂)-NH₂.

17. A peptide of claim 1 that is H-Asp-Tyr(SO₃H)-Met-Gly-Trp-Met-Asp-Tyr(Me)-NH₂.

18. A peptide of claim 1 that is H-Asp-Tyr(SO₃H)-Met-Gly-Trp-Met-Asp-Phe-NHMe.

19. A peptide of claim 1 that is H-Asp-Tyr(SO₃H)-Met-Gly-Trp-Met-Asp-Phe-NHEt.

20. A peptide of claim 1 that is H-Asp-Tyr(SO₃H)-Met-Gly-Trp-Met-Asp-Phe-N(Me)₂.

21. A peptide of claim 1 that is H-Asp-Tyr(SO₃H)-Met-Gly-Trp-Met-Asp-Phe-N(Et)₂.

22. A peptide of claim 1 that is H-Asp-Tyr(SO₃*H)-Ile-Gly-Trp-Ile-Asp-Phe-NH₂.

23. A peptide of claim 1 that is H-Asp-Tyr(SO₃H)-Lys-Gly-Trp-Lys-Asp-Phe-NH₂.

24. A peptide of claim 1 that is H-DAsp-Tyr(SO₃H)-Met-Gly-Trp-Met-Asp-MePhe-NH₂.

25. A peptide of claim 1 that is Hpp(SO₃H)-Met-Gly-Trp-Met-Asp-MePhe-NH₂.

26. A peptide of claim 1 that is H-Asp-Tyr(SO₃H)-Met-Gly-Nal-Met-Asp-Phe-NH₂.

27. A peptide of claim 1 that is Hpp(SO₃*H)-Met-DAla-Trp-Met-Asp-Phe-NH₂.

28. A peptide of claim 1 that is Suc-Tyr(SO₃H)-Ahx-Gly-Trp-Ahx-Asp-Phe-NH₂.

29. A peptide of claim 1 that is H-DAsp-Tyr(SO₃sH)-Ile-Gly-Trp-Ile-Asp-Phe-NH₂.

30. A peptide of claim 1 that is H-Asp-Tyr(SO₃H)-Met-Pro-Trp-Met-Asp-MePhe-NH₂.

31. A peptide of claim 1 that is iBuOCO-Tyr(SO₃H)-Met-DAla-Trp-Met-Asp-MePhe-NH₂.

32. A peptide of claim 1 that is H-βAsp-Tyr(SO₃H)-Ile-Gly-Trp-Ile-Asp-MePhe-NH₂.

33. A peptide of claim 1 that is For-Tyr(SO₃H)-Ile-Gly-Trp-Ahx-Asp-MePhe-NH₂.

34. A peptide of claim 1 that is Suc-Tyr(SO₃H)-Ile-Gly-Trp-Ahx-Asp-MePhe-NH₂.

35. A peptide of claim 1 that is iBuOCO-Tyr(SO₃H)-Ile-Gly-Trp-Ahx-Asp-MePhe-NH₂.

36. A peptide of claim 1 that is Hpp(SO₃H)-Ile-Gly-Trp-Ahx-Asp-MePhe-NH₂.

37. A peptide of claim 1 wherein

Q is H, H-Asp, H-βAsp, H-DAsp, For, Ac, Suc, desQ, or R¹R²CHOCO;

Y is H, (S)—NH or (R)—R³N, or (S)—R³N;

M is Met, DMet, MeMet, MetO, Ahx, DAhx, MeAhx, Leu, MeLeu, Pro, Ile, MeIle, or Lys;

G is Gly, Pro or Sar,

W is Trp, MeTrp or Nal,

X is Met, MeMet, MetO, Ahx, MeAhx, Leu, MeLeu, Ile, MeIle, Pro, or Lys,

J is Asp, DAsp, MeAsp, or Asn,

F¹ is (S)—NH, (S)—R⁴N, or (R)-R⁴N,

F² is H, Cl, I, Br, F, NO₂, NH₂, NH₂, R⁵, or OR⁶,

Z is NH₂, NHR⁷ or NR⁷R⁸,

R¹ and R² are independently H or lower alkyl,

R³, R⁴, and R⁵ are lower alkyl,

R⁶ is H or lower alkyl, and

R⁷ and R⁸ are lower alkyl, and pharmaceutically acceptable salts thereof, provided that (1) Q is desQ when Y is H, (2) F² is not H if, in the same peptide, Q is H-Asp or Ac, Y is (S)—NH, M is either Met, MetO, Ahx or Leu, X is either Met, MetO, Ahx or Leu, G is Gly or Pro, W is Trp, J is Asp, F¹ is (S)—NH, and Z is NH₂, (3) F² is not H if, in the same peptide, Q is Asp or For, Y is (S)—NH, M is Met, Ahx or Leu, G is Gly, W is Trp, X is Met, Ahx or Leu, J is Asp, F¹ is (S)—NH, and Z is NH₂, (4) F¹ is not H if, in the same peptide, Y is H, M is Met, X is Met, G is Gly, W is Trp, J is Asp, F¹ is (S)—NH, and Z is NH₂, and (5) F² is not H if, in the same peptide, Q is Suc, Y is (S)—NH, M is Met, X is Met, G is Gly, W is Trp, J is Asp, F¹ is (S)—NH or (S)—RN, and Z is NH₂.

38. A peptide of claim 2 wherein

Q is H, H-Asp, H-βAsp, H-DAsp, For, Ac, Suc, desQ, or R¹R²CHOCO;

Y is H, (S)—NH, or (S)—R³N;

M is Met, MeMet, Ahx, MeAhx, Leu, MeLeu, Ile, MeIle, or Pro;

G is Gly;

W is Trp;

X is Met, MeMet, Ahx, MeAhx, Leu, MeLeu, Ile, MeIle, or Pro;

J is Asp;

F¹ is (S)—NH or (S)—RN;

F² is H, Cl, NO₂, NH₂, R⁵, or OR⁶, and Z is

39. A peptide of claim 1 that is H-βAsp-Tyr(SO₃*H)-Met-Gly-Trp-Met-Asp-MePhe-NH₂.

40. A peptide of claim 1 that is For-Tyr(SO₃H)-Met-Gly-Trp-Met-Asp-MePhe-NH₂.

41. A peptide of claim 1 that is iBuOCO-Tyr(SO₃H)-Met-Gly-Trp-Met-Asp-MePhe-NH₂.

42. A peptide of claim 1 that is Hpp(SO₃H)-Met-DAla-Trp-Met-Asp-MePhe-NH₂.

43. A peptide of claim 1 that is PrOCO-Tyr(SO₃H)-Met-Gly-Trp-Met-Asp-Phe-NH₂.

44. A peptide of claim 1 that is

EtOCO-Tyr(SO3H)-Met-Gly-Trp-Met-Asp-Phe-NH2.

45. A peptide of claim 1 that is
MeOCO-Tyr(SO3H)-Met-Gly-Trp-Met-Asp-Phe-NH2.

46. A peptide of claim 1 that is
H-Asp-Tyr(SO3H)-Met-Gly-Trp-Met-Asp-Phe-(4-Me)-NH2.

47. A peptide of claim 1 that is
H-Asp-Tyr(SO3H)-Met-Gly-Trp-Met-Asp-Tyr-NH2.

48. A peptide of claim 1 that is
Hpp(SO3H)-Met-Gly-Trp-Pro-Asp-Phe-NH2.

49. A peptide of claim 1 that is
Hpp(SO3H)-Pro-Gly-Trp-Pro-Asp-Phe-NH2.

50. A peptide of claim 1 that is
Suc-Tyr(SO3H)-Ahx-Gly-Trp-Ahx-Asp-MePhe-NH2.

51. A peptide of claim 1 that is
iBuOCO-Tyr(SO3H)-Ahx-Gly-Trp-Ahx-Asp-MePhe-NH2.

52. A peptide of claim 1 that is
Hpp(SO3H)-Ahx-Gly-Trp-Ahx-Asp-MePhe-NH2.

53. A peptide of claim 1 that is
iBuOCO-Tyr(SO3H)-Ahx-Gly-Trp-Ahx-Asp-Phe-NH2.

54. A peptide of claim 1 that is
Hpp(SO3H)-Ahx-Gly-Trp-Ahx-Asp-Phe-NH2.

55. A peptide of claim 1 that is
For-Tyr(SO3H)-Ile-Gly-Trp-Ile-Asp-Phe-NH2.

56. A peptide of claim 1 that is
Suc-Tyr(SO3H)-Ile-Gly-Trp-Ile-Asp-Phe-NH2.

57. A peptide of claim 1 that is
iBuOCO-Tyr(SO3H)-Ile-Gly-Trp-Ile-Asp-Phe-NH2.

58. 2 A peptide of claim 1 that is
Hpp(SO3H)-Ile-Gly-Trp-Ile-Asp-Phe-NH2.

59. A peptide of the formula

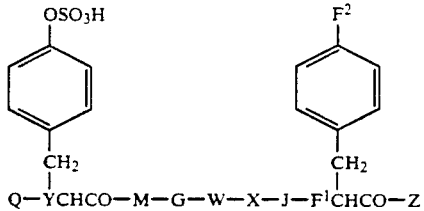

Q—YCHCO—M—G—W—X—J—F¹CHCO—Z wherein
Q is H-βAsp, For, Suc, desQ, or $R^1R^2CHOCO$,
Y is H, or (S)—NH,
M is Met, Ahx, Leu, or Ile,
G is Gly,
W is Trp,
X is Met, Ahx, Leu, or Ile,
J is Asp,
$F^1$ is (S)—NH, or (S)—RN,
$F^2$ is H, NOhd 2, $R^5$, or $OR^6$,
Z is NH2,
$R^1$ and $R^2$ are independently H or lower alkyl,
$R^3$, $R^4$, $R^5$, and $R^6$ are lower alkyl,
and pharmaceutically acceptable salts thereof, provided that
(1) Q is desQ when Y is H,
(2) $F^2$ is not H if, in the same peptide, Q is H-βAsp or For, Y is (S)—NH, M is either Met, Ahx, or Leu, X is either Met, Ahx, or Leu, and $F^1$ is (S)—NH,
(3) $F^2$ is not H if, in the same peptide, Y is H, M is Met, X is Met, and $F^1$ is (S)—NH,
(4) $F^2$ is not H if, in the same peptide, Q is Suc, Y is (S)—NH, M is Met, X is Met, and $F^1$ is (S)—NH or (S)-$R^4$N.

60. A peptide of claim 59 in which Q is iBuOCO.
61. A peptide of claim 59 in which Q is Suc.
62. A peptide of claim 59 in which Q is For.
63. A peptide of claim 1 that is
H-DAsp-Tyr(SO3H)-Ile-Gly-Trp-Ile-Asp-MePhe-NH2.

64. A peptide of claim 1 that is
For-Tyr(SO3H)-Ile-Gly-Trp-Ile-Asp-MePhe-NH2.

65. A peptide of claim 1 that is
Suc-Tyr(SO3H)-Ile-Gly-Trp-Ile-Asp-MePhe-NH2.

66. A peptide of claim 1 that is
iBuOCO-Tyr(SO3H)-Ile-Gly-Trp-Ile-Asp-MePhe-NH2.

67. A peptide of claim 1 that is
Hpp(SO3sH)-Ile-Gly-Trp-Ile-Asp-MePhe-NH2.

68. A peptide of the formula

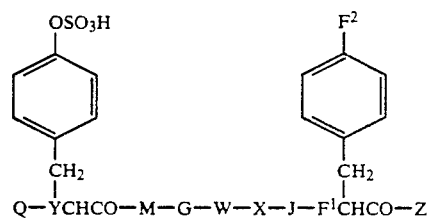

Q—YCHCO—M—G—W—X—J—F¹CHCO—Z wherein
Q is H, H-Asp, H-βAsp, H-DAsp, H-MeAsp, For, Ac, Suc, desQ, or $R^1R^2CHOCO$,
Y is (R)-NH,
M is Met, DMet, MeMet, MetO, Ahx, DAhx, MeAhx, Leu, MeLeu, Pro, Ile, MeIle, or Lys,
G is Gly, DAla, Pro or Sar,
W is Trp, MeTrp or Nal,
X is Met, MeMet, MetO, Ahx, MeAhx, Leu, MeLeu, Ile, MeIle, Pro, or Lys,
J is Asp, DAsp, MeAsp, or Asn,
F is (S)—NH, (S)—$R^4$N, or (R)-$R^4$N,
$F^2$ is H, Cl, I, Br, F, NO2, NH2, $R^5$, or $OR^6$,
Z is NH2, NHR7or NR7R8,
$R^1$ and $R^2$ are independently H or lower alkyl,
$R^3$, $R^4$, and $R^5$, are lower alkyl,
$R^6$ is H or lower alkyl, and
$R^7$ and $R^8$ are lower alkyl,
and pharmaceutically acceptable salts thereof, provided that
(1) $F^2$ is not H if, in the same peptide, Q is H-Asp, M and X are Ile, G is Gly, W is Trp, J is Asp, F is (S)—NH and Z is NH2.

69. A peptide of claim 64 that is
H-Asp-DTyr(SO3H)-Ile-Gly-Trp-Ile-Asp-MePhe-NH2.

70. A peptide of claim 68 that is
H-Asp-DTyr(SO3H)-Met-Gly-Trp-Met-Asp-Phe-NH2.

71. A peptide of claim 68 that is
H-βAsp-DTyr(SO3H)-Met-Gly-Trp-Met-Asp-Phe-NH2.

72. A peptide of claim 68 that is
H-DAsp-DTyr(SO3H)-Met-Gly-Trp-Met-Asp-Phe-NH2

73. A peptide of claim 68 that is
Suc-DTyr(SO3H)-Met-Gly-Trp-Met-Asp-Phe-NH2.

74. A peptide of claim 68 that is
H-Asp-DTyr(SO3H)-Met-Gly-Trp-Met-Asp-MePhe-NH2.

* * * * *

UNITED STATES PATENT AND TRADEMARK OFFICE
CERTIFICATE OF CORRECTION

PATENT NO. : 5,086,042
DATED : February 4, 1992
INVENTOR(S) : James D. Rosamond It is certified that error appears in the above-identified patent and that said Letters Patent is hereby corrected as shown below:

Column 48, line 10, change "NO" to --$NO_2$--; Column 49, lines 6, 36 & 47, and Column 50, line 54, change "$SO_3$° H" to --$SO_3H$--; Column 49, lines 9 & 51, and Column 52, line 17, change "$SO_3sH$" to --$SO_3H$--; Column 50, line 15, delete 2nd occurrence of "$NH_2$"; Column 50, lines 39 & 51, and Column 51, line 56, change "(S)-RN" to --(S)-$R^4N$--; Column 50, line 52, after "Z is" insert --$NH_2$--; Column 51, line 34, change "58. 2A" to --58. A--; Column 51, line 57, change "NOhd 2" to --$NO_2$--; Column 52, line 4, delete the period (".") after "in".

Signed and Sealed this

Twenty-second Day of June, 1993

Attest:

MICHAEL K. KIRK

*Attesting Officer*      *Acting Commissioner of Patents and Trademarks*

UNITED STATES PATENT AND TRADEMARK OFFICE
CERTIFICATE OF CORRECTION

PATENT NO. : 5,086,042
DATED : February 4, 1992
INVENTOR(S) : James D. Rosamond

It is certified that error appears in the above-indentified patent and that said Letters Patent is hereby corrected as shown below:

Column 50, line 4, after H-DAsp," insert --H-MeAsp --.

Column 50, line 30, delete "Asp" and replace with --H,H-βAsp --.

Signed and Sealed this

Fifth Day of July, 1994

BRUCE LEHMAN

Attest:

Attesting Officer        Commissioner of Patents and Trademarks